US012797113B2

United States Patent
McCarthy et al.

(12) United States Patent
(10) Patent No.: US 12,797,113 B2
(45) Date of Patent: Nov. 17, 2026

(54) METHODS AND APPARATUS FOR GUIDED SPINAL GROWTH

(71) Applicant: OrthoPediatrics Corp., Warsaw, IN (US)

(72) Inventors: Richard McCarthy, Little Rock, AR (US); Brian Snyder, Westwood, MA (US); Scott Luhmann, Ladue, MO (US); James Sanders, Chapel Hill, NC (US); David Bumpass, Little Rock, AR (US); Richard M. Schwend, Kansas City, MO (US); Richard Detlefsen, Warsaw, IN (US); Matthew Prygoski, North Liberty, IN (US); Chris M. Powers, Warsaw, IN (US); Collin Gibbs, Columbia City, IN (US); Rebecca Lengyel, Fort Wayne, IN (US); Darren Fugett, Larwill, IN (US); David W. Daniels, Winona Lake, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 0 days.

(21) Appl. No.: 17/995,814

(22) PCT Filed: Apr. 9, 2021

(86) PCT No.: PCT/US2021/026681
§ 371 (c)(1),
(2) Date: Oct. 7, 2022

(87) PCT Pub. No.: WO2021/207674
PCT Pub. Date: Oct. 14, 2021

(65) Prior Publication Data

US 2023/0149047 A1 May 18, 2023

Related U.S. Application Data

(60) Provisional application No. 63/106,564, filed on Oct. 28, 2020, provisional application No. 63/007,597, filed on Apr. 9, 2020.

(51) Int. Cl.
*A61B 17/70* (2006.01)

(52) U.S. Cl.
CPC ............ *A61B 17/702* (2013.01); *A61B 17/70* (2013.01); *A61B 17/7004* (2013.01)

(58) Field of Classification Search
CPC ............ A61B 17/7005; A61B 17/7004; A61B 17/702; A61B 17/704
See application file for complete search history.

(56) References Cited

U.S. PATENT DOCUMENTS

| | | | |
|---|---|---|---|
| 5,672,175 | A | 9/1997 | Martin |
| 6,059,830 | A | 5/2000 | Lippincotte et al. |

(Continued)

FOREIGN PATENT DOCUMENTS

| | | |
|---|---|---|
| CA | 2740496 | 4/2010 |
| CA | 2758590 | 10/2010 |

(Continued)

OTHER PUBLICATIONS

PCT/US2019065043, International Search Report and Written Opinion, ISA, 11 pgs. Feb. 25, 2020.

(Continued)

*Primary Examiner* — Julianna N Harvey

(74) *Attorney, Agent, or Firm* — Gerald W. Roberts; John V. Daniluck; Dentons Bingham Greenebaum LLP

(57) ABSTRACT

Various methods and apparatus for dynamic stabilization of bones, and especially of vertebra. Disclosed herein are bushings that permit axial movement of a rod, tether, or similar interconnection device relative to an anchoring head (Continued)

that is coupled to a bone. Some bushings further allow lateral relative movement or rotational relative movement, such additional relative movement being limited by the size and shape of the bushing, the size and shape of the interconnection device, the size and shape of the bushing container, the manner of attaching the anchoring head to the bone, or other considerations.

8 Claims, 62 Drawing Sheets

(56) References Cited

U.S. PATENT DOCUMENTS

| | | | | |
|---|---|---|---|---|
| 6,485,494 | B1 | 11/2002 | Haider | |
| 6,554,831 | B1 | 4/2003 | Rivard et al. | |
| 6,558,390 | B2 | 5/2003 | Cragg | |
| 7,461,618 | B2 | 12/2008 | Pors et al. | |
| 7,635,380 | B2 | 12/2009 | Zucherman et al. | |
| 7,658,739 | B2 | 2/2010 | Shluzas | |
| 7,658,753 | B2 | 2/2010 | Carl et al. | |
| 7,708,762 | B2 | 5/2010 | McCarthy et al. | |
| 7,731,749 | B2 | 6/2010 | Biedermann et al. | |
| 7,753,958 | B2 | 7/2010 | Gordon et al. | |
| 7,799,055 | B2 | 9/2010 | Lim | |
| 7,806,913 | B2 | 10/2010 | Fanger et al. | |
| 7,854,752 | B2 | 12/2010 | Colleran et al. | |
| 7,942,905 | B2 | 5/2011 | Lim et al. | |
| 7,942,907 | B2 | 5/2011 | Richelsoph | |
| 8,029,547 | B2 | 10/2011 | Veldman et al. | |
| 8,057,518 | B2 | 11/2011 | Fraisier et al. | |
| 8,088,149 | B2 | 1/2012 | White | |
| 8,096,996 | B2 | 1/2012 | Gutierrez et al. | |
| 8,105,364 | B2 | 1/2012 | McCarthy et al. | |
| 8,109,975 | B2 | 2/2012 | Veldman et al. | |
| 8,114,133 | B2 | 2/2012 | Logan | |
| 8,137,384 | B2 | 3/2012 | Heiges et al. | |
| 8,142,437 | B2 | 3/2012 | McLean et al. | |
| 8,157,843 | B2 | 4/2012 | Biedermann et al. | |
| 8,197,516 | B2 | 6/2012 | Biyani | |
| 8,202,301 | B2 | 6/2012 | Prevost et al. | |
| 8,221,467 | B2 | 7/2012 | Butler et al. | |
| 8,277,494 | B2 | 10/2012 | Biedermann et al. | |
| 8,282,671 | B2 | 10/2012 | Connor | |
| 8,308,770 | B2 | 11/2012 | Moumene et al. | |
| 8,313,515 | B2 | 11/2012 | Brennan et al. | |
| 8,357,183 | B2 | 1/2013 | Seme et al. | |
| 8,394,133 | B2 | 3/2013 | Jackson | |
| 8,430,916 | B1 | 4/2013 | Winslow et al. | |
| 8,449,578 | B2 | 5/2013 | Keiser et al. | |
| 8,454,664 | B2 | 6/2013 | McLean | |
| 8,491,641 | B2 | 7/2013 | Nihalani | |
| 8,523,906 | B2 | 9/2013 | McLean | |
| 8,523,922 | B2 | 9/2013 | May et al. | |
| 8,568,458 | B2 | 10/2013 | Matthis et al. | |
| 8,740,945 | B2 | 6/2014 | Hestad et al. | |
| 8,790,374 | B2 | 7/2014 | Iott et al. | |
| 8,795,336 | B2 | 8/2014 | Biedermann et al. | |
| 8,808,379 | B2 | 8/2014 | Abdou et al. | |
| 8,852,239 | B2 | 10/2014 | Jackson et al. | |
| 8,920,472 | B2 | 12/2014 | Seme et al. | |
| 8,974,497 | B2 | 3/2015 | Cho et al. | |
| 8,992,576 | B2 | 3/2015 | Keyer et al. | |
| 9,017,387 | B2 | 4/2015 | Aldridge | |
| 9,101,400 | B2 | 8/2015 | Trieu et al. | |
| 9,144,506 | B2 | 9/2015 | Phelps | |
| 9,168,071 | B2 | 10/2015 | Seme et al. | |
| 9,179,940 | B2 | 11/2015 | Laskowitz et al. | |
| 9,211,143 | B2 | 12/2015 | Barry | |
| 9,271,759 | B2 | 3/2016 | Bailey | |
| 9,277,950 | B2 | 3/2016 | Buttermann | |
| 9,295,500 | B2 | 3/2016 | Marigowda | |
| 9,320,543 | B2 | 4/2016 | Fanger et al. | |
| 9,339,316 | B2 | 5/2016 | Hulliger | |
| 9,414,862 | B2 | 8/2016 | Miller | |
| 9,451,988 | B2 | 9/2016 | Biedermann et al. | |
| 9,451,993 | B2 | 9/2016 | Jackson et al. | |
| 9,486,252 | B2 | 11/2016 | McCarthy et al. | |
| 9,510,865 | B2 | 12/2016 | Elsebaie et al. | |
| 9,517,089 | B1 | 12/2016 | Casey et al. | |
| 9,566,092 | B2 | 2/2017 | Jackson et al. | |
| 9,597,124 | B2 | 3/2017 | McCarthy et al. | |
| 9,636,149 | B2 | 5/2017 | Puttlitz et al. | |
| 9,713,488 | B2 | 7/2017 | Hutchinson | |
| 9,724,145 | B2 | 8/2017 | Spratt et al. | |
| 9,782,204 | B2 | 10/2017 | Spratt et al. | |
| 9,888,944 | B2 | 2/2018 | Zylber et al. | |
| 9,907,578 | B2 | 3/2018 | Biedermann et al. | |
| 9,936,978 | B2 | 4/2018 | Biedermann et al. | |
| 9,968,378 | B1 | 5/2018 | Johnson et al. | |
| 9,974,571 | B2 | 5/2018 | Mueller | |
| 9,999,446 | B2 | 6/2018 | Laskowitz et al. | |
| 10,004,544 | B2 | 6/2018 | Arnold et al. | |
| 10,039,578 | B2 | 8/2018 | Anderson et al. | |
| 10,064,658 | B2 | 9/2018 | Jackson et al. | |
| 10,154,859 | B2 | 12/2018 | Keyer et al. | |
| 10,307,185 | B2 | 6/2019 | Murray | |
| 10,349,983 | B2 | 7/2019 | Purcell et al. | |
| 10,405,892 | B2 | 9/2019 | Harvey et al. | |
| 10,499,968 | B2 | 12/2019 | Wiederkehr et al. | |
| 10,595,908 | B2 | 3/2020 | Strausbaugh | |
| 10,687,860 | B2 | 6/2020 | Seex | |
| 10,736,665 | B2 | 8/2020 | Bobbitt | |
| 10,736,666 | B2 | 8/2020 | Prevost | |
| 10,758,274 | B1 | 9/2020 | Bess et al. | |
| 2003/0100896 | A1 | 5/2003 | Biedermann et al. | |
| 2004/0133202 | A1 | 7/2004 | Suzuki et al. | |
| 2006/0036244 | A1* | 2/2006 | Spitler | A61B 17/3417 606/328 |
| 2006/0116687 | A1 | 6/2006 | Miller et al. | |
| 2006/0276789 | A1* | 12/2006 | Jackson | A61B 17/70 606/301 |
| 2008/0051787 | A1 | 2/2008 | Remington et al. | |
| 2008/0108716 | A1 | 5/2008 | Ayasse et al. | |
| 2008/0195153 | A1 | 8/2008 | Thompson | |
| 2008/0306513 | A1 | 12/2008 | Winslow et al. | |
| 2009/0056222 | A1 | 3/2009 | Gutsol et al. | |
| 2009/0093843 | A1 | 4/2009 | Lemoine et al. | |
| 2009/0097441 | A1 | 4/2009 | Lee et al. | |
| 2009/0198290 | A1 | 8/2009 | Armstrong et al. | |
| 2009/0264931 | A1* | 10/2009 | Miller | A61B 17/704 606/250 |
| 2009/0264933 | A1 | 10/2009 | Carls et al. | |
| 2009/0326584 | A1 | 12/2009 | Slivka et al. | |
| 2010/0063545 | A1 | 3/2010 | Richelsoph | |
| 2010/0063547 | A1 | 3/2010 | Morin et al. | |
| 2010/0087865 | A1* | 4/2010 | Biedermann | A61B 17/7046 606/279 |
| 2010/0096594 | A1 | 4/2010 | Dahlin et al. | |
| 2010/0106193 | A1 | 4/2010 | Barry | |
| 2010/0114165 | A1 | 5/2010 | Ely | |
| 2010/0152776 | A1 | 6/2010 | Keyer et al. | |
| 2010/0211105 | A1 | 8/2010 | Moumene et al. | |
| 2010/0262190 | A1 | 10/2010 | Ballard et al. | |
| 2010/0331887 | A1* | 12/2010 | Jackson | A61B 17/702 606/279 |
| 2011/0029018 | A1 | 2/2011 | Carlos | |
| 2011/0029022 | A1 | 2/2011 | Zehnder et al. | |
| 2011/0144694 | A1 | 6/2011 | Laeng et al. | |
| 2011/0175032 | A1 | 7/2011 | Gunther | |
| 2011/0184463 | A1 | 7/2011 | Schwend | |
| 2011/0251643 | A1 | 10/2011 | Maladi | |
| 2011/0307015 | A1 | 12/2011 | Zucherman | |
| 2012/0290015 | A1 | 11/2012 | Iott | |
| 2013/0172937 | A1 | 7/2013 | Davenport | |
| 2014/0142634 | A1 | 5/2014 | Schlaepfer et al. | |
| 2014/0172023 | A1 | 6/2014 | Garamszegi | |
| 2014/0236235 | A1* | 8/2014 | Jackson | A61B 17/7038 606/267 |
| 2014/0277147 | A1 | 9/2014 | Alexander et al. | |
| 2014/0343609 | A1* | 11/2014 | Friedrich | A61B 17/702 606/255 |
| 2014/0379031 | A1 | 12/2014 | Biedermann et al. | |
| 2015/0025579 | A1 | 1/2015 | Biedermann et al. | |

(56) References Cited

U.S. PATENT DOCUMENTS

| | | | | |
|---|---|---|---|---|
| 2015/0225749 | A1 | 8/2015 | Hickey | |
| 2015/0335358 | A1 | 11/2015 | Luhmann | |
| 2015/0351807 | A1* | 12/2015 | Jackson | A61B 17/7035 606/277 |
| 2016/0130513 | A1 | 5/2016 | Galloway | |
| 2016/0186070 | A1 | 6/2016 | Bashir et al. | |
| 2016/0199104 | A1 | 7/2016 | Ewer et al. | |
| 2016/0262801 | A1 | 9/2016 | Rezach et al. | |
| 2016/0287291 | A1 | 10/2016 | Smith | |
| 2016/0338737 | A1 | 11/2016 | Sicvol et al. | |
| 2016/0344051 | A1 | 11/2016 | Hotto | |
| 2016/0354118 | A1* | 12/2016 | Belliard | A61B 17/7002 |
| 2016/0361097 | A1 | 12/2016 | Richelsoph | |
| 2017/0265900 | A1 | 9/2017 | Lai et al. | |
| 2021/0186571 | A1 | 6/2021 | Jackson | |

FOREIGN PATENT DOCUMENTS

| | | |
|---|---|---|
| CN | 113180809 | 7/2021 |
| DE | 102010028423 | 11/2011 |
| EP | 1795134 | 6/2007 |
| EP | 3103406 | 12/2016 |
| EP | 3225203 | 4/2017 |
| EP | 3406212 | 11/2018 |
| FR | 2799949 | 4/2001 |
| KR | 101870794 | 6/2018 |
| WO | 1999055618 | 11/1999 |
| WO | 2006110463 | 10/2006 |
| WO | 2008061802 | 5/2008 |
| WO | 2010030906 | 3/2010 |
| WO | 2010037098 | 4/2010 |
| WO | 2010046571 | 4/2010 |
| WO | 2012064360 | 5/2012 |
| WO | 2012076005 | 6/2012 |
| WO | 2012167105 | 12/2012 |
| WO | 2016077621 | 5/2016 |
| WO | 2018022679 | 2/2018 |
| WO | 2020123857 | 6/2020 |

OTHER PUBLICATIONS

PCT/US2019065043, International Preliminary Report on Patentability, IB, 9 pgs. Feb. 6, 2018.

El-Hawary R, Akbarnia BA, "Early Onset Scoliosis, Time for Consensus," Spine Deform. Mar. 4, 2015, pp. 105-106.

Williams BA, Matsumoto H, McCalla DJ, Akbarnia BA, Blakemore LC, Betz RR, Flynn JM, Johnston CE, McCarthy RE, Roye DP Jr, Skaggs DL, Smith JT, Snyder BD, Sponseller PD, Sturm PF, Thompson GH, Yazici M, Vitale MG., "Development and initial validation of the Classification of Early-Onset Scoliosis (C-EOS)," J Bone Joint Surg Am., pp. 1359-1367, Aug. 20, 2014.

Yang S, Andras LM, Redding GJ, Skaggs DL, "Early-Onset Scoliosis: A Review of History, Current Treatment, and Future Directions," Pediatrics., 14 pgs., Dec. 7, 2015.

Shekelle p. Woolf SH, Eccles M, Grimshaw J, "Clinical guidelines: developing guidelines," BMJ, vol. 318, pp. 593-496, Feb. 27, 1999.

Zhang YB, Zhang JG, "Treatment of early-onset scoliosis: techniques, indications, and complications," Chin Med J, pp. 351-357, Feb. 5, 2020.

Sponseller PD, Betz R, Newton PO, Lenke, LG, Lowe T, Crawford, A, Sucato D, Lonner B, Marks M, Bastrom T, Harms Study Group, "Differences in curve behavior after fusion in adolescent idiopathic scoliosis patients with open triradiate cartilages," Spine, vol. 34, No. 8, pp. 827-831, Apr. 4, 2009.

Gussous YM, Tarima S, Zhao S, Khan S, Caudill A, Sturm p. Hammergerg KW, "Serial Derotational Casting in Idiopathic and Non-Idiopathic Progressive Early-Onset Scoliosis," Spine Deform., pp. 233-238, Apr. 23, 2015.

Fedorak GT, Stasikelis PJ, Carpenter AM, Nielson AN, D'Astous JL, "Optimization of Casting in Early-onset Scoliosis," J Pediatr Orthop., pp. 303-307, Apr. 2019.

Canavese F, Samba A, Dimeglio A, Mansour M, Rousset M, "Serial elongation-derotation-exion casting for children with early-onset scoliosis," World J Orthop., vol. 6, issue 11, pp. 935-942, Dec. 18, 2015.

Moreau S, Lonjon G, Mazda K, Ilharreborde B, "Detorsion night-time bracing for the treatment of early onset idiopathic scoliosis," Orthop Traumatol Surg Res, pp. 935-939, May 24, 2014.

Hardesty CK, Huang RP, El-Hawary R, Samdani A, Hermida PB, Bas T, Balioğlu MB, Gurd D, Pawelek J, McCarthy R, Zhu F, Luhmann S; Growing Spine Committee of the Scoliosis Research Society, "Early-Onset Scoliosis: Updated Treatment Techniques and Results," Spine Deform. Jul.-Aug. 2018 6(4), pp. 467-472.

Liang J, Li S, Xu D, Zhuang Q, Ren Z, Chen X, Gao N, "Risk factors for predicting complications associated with growing rod surgery for early-onset scoliosis," Clin Neurol Neurosurg. 136, pp. 15-19, May 28, 2015.

Sun ZJ, Qiu GX, Zhao Y, Guo S, Zhang J, Shen J, Wang Y, Zhao, H, Li S, "Dual growing rod treatment in early onset scoliosis: the effect of repeated lengthening surgeries on thoracic growth and dimensions," Eur Spine J., pp. 1434-1440, Jul. 2015.

Bess S, Akbarnia BA, Thompson GH, Sponseller PD, Shah, SA, Sebaie HE, Boachie-Adjei B, Karlin LI, Canale S, Poe-Kochert C, Skaggs DL, "Complications of growing-rod treatment for early-onset scoliosis: analysis of one hundred and forty patients," J Bone Joint Surg Am., pp. 2534-2543, Nov. 3, 2010.

McCarthy RE, Luhmann S, Lenke L, McCullough FL, "The Shilla growth guidance technique for early-onset spinal deformities at 2-year follow-up: a preliminary report," J Pediatr Orthop., pp. 1-7, Jan. 2014.

Wang Wenjun, Xue Jingbo, Yan Yiguo, et al. Preliminary report on the treatment of children's scoliosis with a new type of internal xation system with growth rod of the chute screw [J]. Chinese Journal of Orthopedics, 2013, 2:147-151 Jan.

Zhu, Feng & Song, Xiangjian & Wang, Qinglei, "Treatment of early-onset scoliosis with Co—Cr—Mo multidirectional sliding growth rod technique," 15 pgs., Jan. 24, 2024.

Du Y, Bian Y, Zhao Y, Yang Y, Lin G, Han B, Zhang H, Li C, Ye X, Li Z, Zhang J, "A Novel Growth Guidance System for early onset scoliosis: a preliminary in vitro study," 16 pgs., Feb. 23, 2024.

Akbarnia BA, Marks DS, Boachie-Adjei O, Thompson AG, Asher MA, "Dual growing rod technique for the treatment of progressive early-onset scoliosis: a multicenter study," Spine, vol. 30, No. 17S, pp. S46-S57, 2005.

Flynn JM, Tomlinson LA, Pawelek J, Thompson GH, McCarthy R, Akbarnia BA, and Growing Spine Study Group, "Growing-rod graduates: lessons learned from ninety-nine patients who completed lengthening," J Bone Joint Surg Am, pp. 1745-1750, Oct. 2, 2013.

Wang S, Zhang J, Qiu G, Wang Y, Li S, Zhao Y, Shen J, Weng X, "Dual growing rods technique for congenital scoliosis: more than 2 years outcomes: preliminary results of a single center," Spine, vol. 37, No. 26, pp. E1639-E1644, Dec. 2012.

Kim G, Sammak SE, Michalopoulos GD, Mualem W, Pinter ZW, Freedman BA, Bydon M, "Comparison of surgical interventions for the treatment of early-onset scoliosis: a systematic review and meta-analysis," J Neurosurg Pediatr, vol. 31, pp. 342-357, Apr. 2023.

McCarthy RE, Sucato D, Turner JL, Zhang H, Henson MA, McCarthy K, "Shilla growing rods in a caprine animal model: a pilot study," Clin Orthop Relat Res, 705-710, Mar. 2010.

McCarthy RE, McCullough FL. Shilla Growth Guidance for Early-Onset Scoliosis: Results After a Minimum of Five Years of Follow-up, J Bone Joint Surg Am., pp. 1578-1584, Oct. 7, 2015.

Andras LM, Joiner ER, McCarthy RE, McCullough L, Luhmann SJ, Sponseller PD, Emans JB, Barrett KK, Skaggs DL; Growing Spine Study Group, Growing Rods Versus Shilla Growth Guidance: Better Cobb Angle Correction and T1-S1 Length Increase But More Surgeries, Spine Deform, pp. 246-252, May 2015.

Nazareth A, Skaggs DL, Illingworth KD, Parent S, Shah SA, Sanders JO, Andras LM, Growing Spine Study Group, "Growth guidance constructs with apical fusion and sliding pedicle screws (SHILLA) results in approximately ⅓rd of normal T1-S1 growth," Spine Deform. pp. 531-535, Feb. 24, 2020.

(56) References Cited

OTHER PUBLICATIONS

Toth JM, Ankomah F, Kawakami N, Uno K. A comparison of the inflammatory host response to particulate debris adjacent to unlocked and locked screws of a growth guidance system for early onset scoliosis. Eur Spine J. 2022;31(9):2301-10.

Lukina E, Laka A, Kollerov M, Sampiev M, Mason p. Wagstaff p. Noordeen H, Yoon W, Blunn G, "Metal concentrations in the blood and tissues after implantation of titanium growth guidance sliding instrumentation," Spine J., pp. 1-27, 2016.

Mardjetko SM, Hammerberg KW, Lubicky JP, Fister JS. The Luque trolley revisited. Review of nine cases requiring revision. Spine (Phila Pa 1976). 1992;17(5):582-9.

Luhmann SJ, McCarthy RE, "A Comparison of Shilla Growth Guidance System and Growing Rods in the Treatment of Spinal Deformity in Children Less Than 10 Years of Age," J Pediatr Orthop, pp. E567-E574, Dec. 2017.

Luhmann SJ, Smith JC, McClung A, Mccullough FL, McCarthy RE, Thompson GH, Growing Spine Study Group, "Radiographic Outcomes of Shilla Growth Guidance System and Traditional Growing Rods Through Definitive Treatment," Spine Deform, pp. 277-282, Jul. 2017.

Luhmann SJ, McAughey EM, Ackerman SJ, Bumpass DB, McCarthy RE, "Cost analysis of a growth guidance system compared with traditional and magnetically controlled growing rods for early-onset scoliosis: a US-based integrated health care delivery system perspective," Clinicoecon Outcomes Res, pp. 179-187, Mar. 2018.

Sucato DJ, "Guiding Growth Is Promising But Can It Compare with Growth Promotion?" Commentary on an article by Richard E. McCarthy, MD, and Frances L. McCullough, "Shilla Growth Guidance for Early-Onset Scoliosis. Results After a Minimum of Five Years of Follow-up". J Bone Joint Surg Am. Oct. 7, 2015, 2 pgs.

Morell SM, McCarthy RE, "New developments in the treatment of early-onset spinal deformity: role of the Shilla growth guidance system," Medical Devices: Evidence and Research, pp. 241-246, Jul. 20, 2016.

Bogie R, Voss L, Arts JJ, Lataster A, Willems PC, Brans B, Van Rhijn LW, Welting Tjm, "UHMWPE Sublaminar Wires in Posterior Spinal Instrumentation: Stability and Biocompatibility Assessment in an Ovine Pilot Study," Clin Spine Surg. 19 pgs., 2016.

Agarwal A, Aker L, Ahmad AA, "Active Apex Correction With Guided Growth Technique for Controlling Spinal Deformity in Growing Children: A Modi ed SHILLA Technique," Global Spine J, vol. 10(4) pp. 438-442, 2020.

Ahmad AA, Agarwal A, "Active Apex Correction: An overview of the modi ed SHILLA technique and its clinical efficacy," J Clin Orthop Trauma, pp. 848-852, Jul. 13, 2020.

Agarwal A, Aker L, Ahmad AA, "Active Apex Correction (Modi ed SHILLA Technique) Versus Distraction-Based Growth Rod Fixation: What Do the Correction Parameters Say?" Spine Surg Relat Res, pp. 31-36, Aug. 16, 2019.

Skov ST, Li H, Hansen ES, Hoy K, Helmig p. Rolfing JD, Bunger C, "New growth rod concept provides three dimensional correction, spinal growth, and preserved pulmonary function in early-onset scoliosis," Int Orthop, pp. 1773-1783, 2020.

Wijdicks SPJ, Skov ST, Li H, Castelein RM, Kruyt MC, Bunger C, 3-Year follow-up of a single magnetically controlled growing rod with contralateral gliding system and apical control for early onset scoliosis. Spine Deform. pp. 751-761, 2020.

Peng, "Titanium vs Stainless Steel, What is the Difference?" Jan. 6, 2021; https://www.dekmake.com/titanium-vs-stainless-steel/.

Dwinuria, "Comparison of friction coefficient and surface roughness on stainless steel, nickel titanium, and nickel-titanium copper wires to standard edgewise brackets: An experimental in vitro study" 71-75. Journal of International Oral Health. Jan. 28, 2021.

Canadian Intellectual Property Office, First Office Action, Serial No. 3178868, 4pgs., Apr. 24, 2024.

PCT/US2022/075524, International Search Report and Written Opinion, ISA/US, Feb. 1, 2023, 6 pgs.

PCT/US2022/077379, International Search Report and Written Opinion, ISA/US, Feb. 14, 2023, 12 pgs.

Barend Grove, "Examination report No. 1 for your standard patent application," AU Patent Application No. 2021253951, Oct. 13, 2025, pp. 1-4, IP Australia, Australia.

Ouellet JA, Ferland CE, Klein K, Racloz G, Klein K, Richter H, Steffen T, Von Rechenberg B, "Evaluation of the Modern Luque Trolley Construct for the Treatment of Early-onset Scoliosis Using a Gliding Implant in an Immature Animal Model," Clin Spine Surg, vol. 30, No. 4, pp. E460-E465, May 2017.

Victoria J. Dempster, Patent Examiner, Examiner's Report for Canadian Patent Application No. 3178868, dated Mar. 5, 2026, 4 pages, Canadian Intellectual Property Office ("CIPO").

* cited by examiner 6
1
10
4
10

6
10

10
58c 10
4
58b
60c

1

12.5 mm x 13.9 mm

METHODS AND APPARATUS FOR GUIDED SPINAL GROWTH

CROSS REFERENCE TO RELATED APPLICATIONS

This application claims the benefit of priority to U.S. Provisional Patent Application Ser. No. 63/007,597, filed Apr. 9, 2020, and U.S. Provisional Patent Application Ser. No. 63/106,564, filed Oct. 28, 2020, both of which are incorporated herein by reference.

FIELD OF THE INVENTION

Various embodiments described herein pertain to methods and apparatus that facilitate positional readjustment of vertebra relative to one another, such as in a surgical procedure using rods that are slidably received by a bone attachment device, and including those attachment devices using a separate low friction bushing that permits sliding but limits translational movement of the rod in lateral and vertical orientations.

SUMMARY OF THE INVENTION

Various embodiments shown herein pertain to bone anchors that place boundaries on the movement of a spinal rod, while simultaneously permitting the rod to move axially.

In some embodiments the rod is able to rotate within a bushing and relative to the bone anchor assembly in roll (about the rod axis) and pitch and yaw (both perpendicular to the rod axis). In yet other embodiments the bushing and rod are able to rotate relative to the bone anchor assembly in roll (about the anchor attachment to the bone) and pitch and yaw (both perpendicular to the anchor attachment to the bone). Still further embodiments contemplate combinations of any of the aforementioned rod relative motions and any of the aforementioned bushing and rod relative motions.

Various embodiments include a tulip-type anchoring head that includes within it a low-friction bushing that comes into contact with a spinal rod. It has been found in some patients that the use of a metallic bushing can result in metal particles deposited in the patient as a result of the relative motion of a metal rod against a metal head. These of a polymeric bushing can assist in resolving this problem, and also the use of a bushing of any material that is fabricated from a hard, low-friction, biologically acceptable material, such as a ceramic or metal. One examples of such a metal contains cobalt and chromium.

In some embodiments the polymeric bushings are fabricated from a high density polyethylene material, polyetheretherketone (PEEK), or other biologically acceptable, non-metallic material. In some embodiments the polymeric bushing is a separate component that is inserted into the head of the device. In yet other embodiments, the polymeric bushing is contained within a container, such that the separable container is attached to the head. In still further embodiments the polymeric bushing is a coating of polymeric material that can be applied to a surface of the head or to the surface of a separable container.

In some embodiments, the bushing (polymeric, metallic, or ceramic) is a closed pathway having two opened ends, through which the rod is inserted. In still other embodiments the bushing can be in multiple pieces, preferably with one of the bushing pieces defining an open pathway having two opposing ends. In such multi-piece bushings the rod can be inserted into the bushing in a direction orthogonal to the direction of the pathway.

In some embodiments, the bushing whether separable or integral with the head, is restrained by the head in a single static position, such that movement of the rod does not result in movement of the bushing. In still other embodiments the exterior of the bushing has a shape that coacts with the interior shape of a pocket (either of the head or a container) such that the rod pathway through the bushing can pivot in one or two directions (such as pitch or yaw) relative the head of the guiding retainer assembly.

In some embodiments, the bushing aperture through which the rod is placed has a shape that is substantially the same as the exterior shape of the rod, although with provisions (such as clearance around the perimeter) to permit relative sliding motion of the rod. In still further embodiments the interior shape of the bushing pathway has an interior width that is greater than the width of the rod, such that side to side motion of the rod relative to the bushing is permitted.

Various embodiments include means for retaining a bushing within a head. Such retaining means can include a set screw having external threads that is received within an internally threaded pocket of the head. In still further embodiments the set screw can have internal heads that are received onto exterior threads of the head or other device. In some embodiments the means for retaining can be a set screw that is oriented generally perpendicular to the rod pathway, and in some embodiments being centered across the width of the bushing and in yet other embodiments offset to one side of the bushing. In still further embodiments the means for retaining the bushing can be a c-clip that is received within a groove of the head, and capturing the bushing between the c-clip and the internal pocket of the head.

Preferably, the full tightening of the set screw or locking of other retaining device does not compress the bushing against the surface of the rod so much as to prevent sliding of the rod, especially for sliding that results from the motion of one vertebra relative to another vertebra, or from the actions of the surgeon. Preferably, those embodiments utilizing set screws include a travel-stop feature that limits the full travel of the set screw from compressing the bushing against the surface of the rod when fully the set screw is fully tightened.

Still other means for retaining the bushing contemplate bushings within separable containers (the bushings either separately installed or molded within the container), with the container and a head being adapted and configured to securely locate the container on the head. As one example, the container can include a separable bushing, in some embodiments the ends of the bushing extending outwardly from the edges of the container, and in other embodiments remaining flush with the container edges. The container includes one or more head retention features that coact with a corresponding bushing retention feature on the head to securely locate the container and bushing relative to the head. As one example, the head retention features can include one or more projections, preferably on opposite sides of the container exterior that coact with hinged members located on the head, such that the placement of the container within the head causes the bushing retention features to deflect outward (being retained on the head by live hinges), and then snap back into a retaining position once the head retention features are lower than the bushing cantilever arms.

In yet another embodiment the bushing container includes one or more flexible arms (by way of live hinges), such that the container can be compressed onto the head with the arms springing outward to pass over locking features on the head during insertion, and then snapping back into place in a locking manner after the bushing container is fully received on the head.

In still further embodiments of the present invention the means for retaining the bushing includes heads that are pre-loaded with a bushing (either separable or molded-in), in which can be retained as a single unit on the bone supporting device. As one example, the head includes a head having a receiving pocket that can be popped onto the head of a supporting device, such as by use of a compression tool.

Preferably, either the head of the supporting device or the interior of the head pocket is lined with a polymer, metal, or ceramic to act as a bearing and permit one or two axes of relative motion. In yet another embodiment the head is adapted and configured proximate to the device receiving pocket to receive a lockable sliding member. When the sliding member is in an opened position, the assembly of the head, bushing, and sliding member can be placed readily on top of the supporting device. After placement, the sliding device can be pushed into locking engagement with the head, and further capturing the supporting device to the head.

In still further embodiments the head of the guiding retainer can be attached by a flexible connector to the vertebra, with some embodiments including a spiked bone interface on the bottom of the head. In such embodiments the flexible connector can be wrapped around the vertebra and captured within the head.

Still further embodiments contemplate the use of a flexible connector to attach the bushing to the head, such as a head having a groove or channel in which to locate the bearing, with attachment slots located on either side of the groove. The flexible connector can be wrapped around the exterior of the bushing, with the ends of the connector being attached to the head slots. In yet another variation, the flexible connector is wrapped around the rod directly, such that the wrapping of the flexible connector provides the polymeric pathway for the rod. The ends of the wrapped connector can be attached to the head with any degree of looseness as desired by the surgeon, thus permitting axial movement of the rod, as well as polyaxial pivoting of the rod relative to the head.

Still further embodiments of the present invention contemplate a bushing that is supported within a separable container, the container including a support arm, the support arm being coupled to the head and locked to the head. In such embodiments, the pathway for the rod can be laterally offset from the head.

Various embodiments of the present invention contemplate various means for supporting the head from a vertebra. In some embodiments, the head is fixed to a supporting device such as a bone screw. In still further embodiments, the head is coupled to a bone screw by means of a joint that permits a single axis of pivotal movement of the head relative to the supporting device. In still further embodiments, the interface between the supporting device and the head permits polyaxial movement of the head relative to the supporting device (along either two axes or three axes).

BRIEF DESCRIPTION OF THE DRAWINGS

Some of the figures shown herein may include dimensions. Further, the figures shown herein have been created from scaled drawings, scaled models, or from photographs that are scalable. It is understood that such dimensions, or the relative scaling within a figure, are by way of example, and not to be construed as limiting unless so stated in a claim. Persons of ordinary skill will also recognize that CAD renderings may include lines that pertain to changes in the geometry of the computer model, and not necessarily to component features.

FIGS. 5A1-5D4 show various embodiments with various arrangements of bushings and heads. FIGS. 5A1-5A6 show six different arrangements of top loaded bushings, each captured within the head with different methods and apparatus; FIGS. 5B1-5B3 show three configurations of heads, in which the bushings are loaded by laterally sliding the bushings into the cavity; FIGS. 5C1-5C2 show two configurations, in which the heads receive the bushings with a tip of the bushing being inserted at an angle into the head; and FIGS. 5D1-5D4 show four arrangements of heads, in which the bushings are integral with the head).

FIGS. 6A-6D show an anchor in which the bushing is in multiple segments. FIG. 6A shows the anchor assembled with a rod from a top perspective view; FIG. 6B shows an exploded end view of the apparatus of the FIG. 6A; FIG. 6C shows a further exploded view of a portion of the apparatus of FIG. 6B; and FIG. 6D shows a cross sectional end view of the apparatus of FIG. 6A with the cross section being taken through the centerline of the screw and perpendicular to the axis of the rod. These devices include bushing-rod interfaces on multiple different components. In some embodiments these components are assembled together at the time of surgery.

FIGS. 7A-7E show an anchor in which the bushing and bushing container are loaded separately from the top. FIG. 7A shows a top, perspective view of a partly assembled anchor head; FIG. 7B shows an assembled view of the apparatus of FIG. 7A; FIG. 7C is a cross sectional, side view of the apparatus of FIG. 7B, as exploded from a view of another bushing container; FIG. 7D shows the assembly of FIG. 7C; FIG. 7E is a perspective, top, side view of the apparatus of FIG. 7D with a bushing inserted; and FIG. 7F is a perspective, cross sectional cutaway of the apparatus of FIG. 7E. These devices provide an alternative construction to a press- fit sleeve or bushing, and are useful in many different embodiments shown herein. Further, these devices can also be used with integral bushings.

FIGS. 9A1-9E compare the spatial envelopes of two different anchors. FIG. 9A1 shows an exploded anchor with a fixed head, an oblong cross section, slide-loaded bushing; FIG. 9A2 depicts the assembly of the anchor of FIG. 9A1; FIG. 9B shows a different anchor with a polyaxial attachment and a circular rod cross section; FIG. 9C shows the anchor of FIG. 9A1, with various external dimensions compared to the anchor of FIG. 9B; FIG. 9D shows the rod maximum articulation envelope (Range of Movement, or ROM) of the anchor of FIG. 9B; and FIG. 9E provides a side-by-side comparison with FIG. 9D. Preferably, these embodiments include a cross linked organic material with the bushing. In some embodiments a fixed screw is used with a slide-loaded oblong bushing, the bushing providing mobility. Preferably, some of these embodiments include a low profile after implantation so as to reduce internal irritation within the patient. FIG. 9D illustrates the rod ROM (range of movement). FIG. 9E shows that a fixed screw in some embodiments achieves additional protection of the patent tissue from encroachment by the head of the screw.

FIG. 10A shows a bushing with an oblong interior and oblong exterior; FIG. 10B shows a bushing in a similar anchor with a cylindrical internal cross section and oblong exterior; FIG. 10C shows the bushing of FIG. 10B with the rod pathway offset from the fastener centerline; FIG. 10D shows an opposite-hand version of the anchor of FIG. 10C; FIG. 10E shows the anchor of FIG. 10A with an installed rod (in cross-section) having width that is greater than the height of the busing, so as to limit rotation of the rod. Some of these devices permit an oblong aperture to be converted to a fixed or offset-fixed rod retention envelope. It is thought that the restricted motion may improve the correction of the patient's spine. In some embodiments the same screw base can be utilized, such that one screw can provide four different rod placement options.

FIGS. 11A-11E show various views of an anchor with a spherical bushing. FIG. 11A is an assembled, top and side perspective view, partly transparent, of an assembled anchor supporting a bushing with a spherical bushing permitting two dimensional rotation of the bushing; FIG. 11B is an exploded view of the anchor of FIG. 11A; FIG. 11C is a side elevational cross sectional representation of the anchor of FIG. 11B containing a rod; FIG. 11D is a side elevational view of the anchor of FIG. 11B; and FIG. 11E shows an anchor similar to that of FIG. 11D, except using a polyaxial junction between the head and the support device, and a bushing with a cylindrical outer surface not rotatable within the head. In some of the devices shown herein the bushing is adapted and configured so as to minimize binding of the rod by placement of the point of rotation on the rod axis. In yet other embodiments, a spherical bushing eliminates the screw head to rod moment arm illustrated in FIG. 11E.

FIGS. 12A-12G show various views of an anchor. FIG. 12A is a top, side perspective exploded view of an anchor; FIG. 12B is an end elevational view of the partly assembled apparatus of FIG. 12A; FIG. 12C is a side elevational cutaway view of the assembled anchor of FIG. 12B; FIG. 12D shows a portion of the anchor of FIG. 12A showing the busing and busing container and a means of interlocking; FIG. 12E is an external, top, side perspective view of the apparatus of FIG. 12C with the bushing of FIG. 12D locked in place; FIG. 12F is a side cross sectional view, similar to FIG. 12C but taken parallel to the rod axis, and showing the convex internal shape of the rod pathway; and FIG. 12G is a perspective view from above of the partially assembly anchor of FIG. 12F. Various of these embodiments include a metal-lined bushing that is reduced into the head of the tulip device, and preferably providing a low profile implantation with less than about fifteen millimeters from the top of the implanted device to the bone surface. Various devices used an unlocked, low-friction junction. Some devices include a metal shell having a taper-lock 56*a* and snap-teeth 26*b* that can be used in place of a set screw. In some embodiments, these devices function with a traditional driver and reducer. The embodiment shown in FIGS. 12A-12G includes an integral polymer bushing that is contoured and metal lined, in one embodiment. It is supported by a traditional tulip with a polyaxial, polymer-lined junction. The bushing is retained with taper locks and/or snap teeth and live hinges. Still further variations include bushing designs that are oblong, modular oblong, and spherical. Still further, wrap-around saddles are contemplated, and further the use of concentric set screws for bushing retention, as non-limiting examples of variations. Further contemplated are bushings or bushing portions of the head that are adapted and configured for loose, low friction support of the rod, and fabricated or coated with polymeric, metallic, or ceramic materials.

FIGS. 13A1-13D3 show various means for supporting a bushing container from the head. FIGS. 13A1-13A6 show six different attachment heads, including tulip, slide load, and integral attachment heads; FIGS. 13B1-13B2 show attachment heads and supporting devices that are modular, including FIG. 13B1 for slide-lock coupling and FIG. 13B2 for push and snap on coupling; FIGS. 13C1-13C3 show bushing support devices that are modular outriggers; and FIGS. 13D1-13D3 show an anchor (in FIG. 13D1, perspective cross section; in FIG. 13D2, perspective assembly; and in FIG. 13D3, perspective exploded) with a modular outrigger and related screw. In the device shown as FIG. 13C2, it can be seen that the spinal attachment device is shown with slots adapted and configured for a band (such as with BandLoc™). it is understood that this device would also work with a pedicle screw having a tulip head.

FIG. 14A shows a partial assembly of an anchor in a top, side, perspective orientation; FIG. 14B shows an exploded view of the anchor; FIG. 14C shows the assembled view of the anchor of FIG. 14B; FIG. 14D shows a cross sectional representation of a fully assembled anchor, from a top, side perspective orientation; and FIG. 14E shows the external view of the apparatus of FIG. 14D. Various embodiments shown herein include an "inline" outrigger device that preferably moves the polymer bushing (or bushing with polymeric, metallic, or ceramic surfaces for contact with the rod) outside the profile of the device tulip head. As shown in FIG. 14D the rod outer diameter after insertion is clear of the inside 24*b* of the tulip because the rod is supported by the pair of bushing bearing surfaces that roughly match the rod O.D, whereas the inside 24*b* of the tulip is a larger, clearance diameter relative to the rod O.D.

FIGS. 15A-15D show various views of an anchor according to another embodiment of the present invention. FIG. 15A shows a top, side, perspective view of an assembled anchor coupled to a rod; FIG. 15B is a side, top, perspective representation of a portion of the apparatus of FIG. 15A; FIG. 15C is a side elevational cross sectional view of the apparatus of FIG. 15B; and FIG. 15D is a side, top perspective enlargement of the apparatus of FIG. 15B. Devices according to some embodiments of the present invention include a band that is loosely wrapped around the rod. In this manner, the rod is retained to the anchor, but the rod can move. Preferably, the band in some embodiments directly wraps around the rod. Still further embodiments, such as that shown in FIG. 15D, utilize a fixe anchor with a buckle-style attachment to the band.

FIGS 16A-16B show an alternative anchor to the anchor of FIGS. 15A-15D. FIG. 16A is an end view of a cutaway of an anchor according to another embodiment of the present invention; and FIG. 16B is a top, side, perspective representation of a portion of the apparatus of FIG. 16A. Various embodiments disclosed herein pertain to implantable devices having a band that wraps around the polymer bushing. In some embodiments a polyester band wraps around a UHMWPE bushing, the band having a metal retaining clip on one end, and being pulled tight through a sliding lock mechanism 44*c* in order to reduce and retain the bushing.

FIGS. 17A-17D show various views of an anchor according to another embodiment of the present invention. FIG. 17A is a side, top, perspective view of an assembled anchor according to another embodiment of the present invention; FIG. 17B is an exploded view of the anchor of FIG. 17A; FIG. 17C is a side elevational cross sectional view of the apparatus of FIG. 17A; and FIG. 17D is a view of the apparatus of FIG. 17C with exemplar dimensions. Various embodiments disclosed herein pertain to a device open from the top, with the bushing being reduced into place within the tulip. Preferably, there is a locking polymer junction that results in a minimization of any excess debris at the interface, and in some embodiments less range of motion. A wrap around middle saddle transfers a compression load past the polymer bushing. Preferably, the devices of FIGS. 17A-17D can be pivotal in either a polyaxial or uniaxial configuration. Further, a similar concept can be used with a cylindrical or contoured bushing.

FIGS. 18A1-18F provide comparisons of alternative anchors according to different embodiments of the present invention. FIG. 18A1 illustrates that the anchor of FIG. 18A2 permits rotation of the head relative to the bone screw in 3 orthogonal axes; FIG. 18A2 shows an exploded view of a slide loaded bushing on a polyaxial support device; FIG. 18B shows a device similar to that of FIGS. 18A1-18A2, except using a top loaded bushing; FIG. 18C shows an anchor similar to that of FIGS. 18A1-18A2, except with a closed head; FIG. 18D shows an exploded view of an anchor similar to that of FIGS. 18A1-18A2, except with uniaxial attachment to a support device; FIG. 18E shows a device similar to that of FIG. 18B, except with a uniaxial support device; and FIG. 18F shows a device similar to that of FIG. 18C, except with a uniaxial support device. It can be seen that the assembled implant shown in FIGS. 18A1-18A2 in some embodiments permits rotational movement about two or more axes. In contrast, the device of FIG. 18D shows a single axis of rotation in the medial-lateral direction.

FIGS. 19A-19D show various views of an anchor according to another embodiment of the present invention. FIG. 19A is an exploded view of the anchor from a top, side, perspective orientation; FIG. 19B is a partly assembled view of the apparatus of FIG. 19A; FIG. 19C is a side elevational view of the apparatus of FIG. 19B; and FIG. 19D shows the apparatus of FIG. 19C fully locked into place. FIG. 19A shows that the tulip head can be reduced onto the screw head and have a profile from the top surface of the implant to the bone surface of under seventeen millimeters for those assemblies that are not preassembled, although in some devices that are preassembled such as for upper thoracic use a pre-assembled device has a profile of under fifteen millimeters. In some embodiments, the locking metal junction results in minimization of excess debris, and in some embodiments less range of movement. It is understood that various configurations shown on FIGS. 19A-19D can be configured as an unlocked implant by eliminating the taper lock interface.

FIGS 20A-20E show various views of an anchor according to another embodiment of the present invention. FIG. 20A shows an exploded view of the anchor from a top, side perspective orientation; FIG. 20B shows the anchor of FIG. 20A partly assembled; FIG. 20C shows the anchor of FIG. 20A fully assembled in a side perspective view; FIG. 20D is a side elevational cross sectional representation of the apparatus of FIG. 20C, and FIG. 20E is a close up view of a portion of FIG. 20D. The embodiments of FIGS. 20A-20E are preferably implanted by first inserting the screw shank into the bone, then placing the tulip attachment device onto the rod, and then reducing the tulip device and rod onto the screw head. In some embodiments the assembled profile from top of the implant to the bone surface is under seventeen millimeters, and in those embodiments that are preassembled such as for upper thoracic use, the profile is less than fifteen millimeters. Various of these devices include a "pop on" feature for coupling the tulip head the attachment device. The embodiment shown in FIGS. 20A-20E includes an integral bushing with a contoured exterior, used on a modular tulip with pop-in junctions and polymer lined junctions. It is understood that yet various other embodiments pertain to bushing designs that are oblong, modular oblong, and spherical, as a non-limiting list of options.

FIGS. 21A-21B show anchors according to various embodiments of the present invention. FIG. 21A (top view) shows a cross sectional view of a portion of an assembled anchor according to another embodiment of the present invention; and FIG. 21B (lower) shows the external view of the top view.

FIGS. 22A-22E show various views of an anchor according to another embodiment of the present invention. FIG. 22A shows an exploded view of a portion of the anchor in a side, cross sectional representation; FIG. 22B illustrates the partial assembly of the components of FIG. 22A; FIG. 22C shows the seated assembly of the apparatus of FIG. 22B; FIG. 22D shows a top, side, perspective external view of a portion of the anchor, and also a cross sectional, side elevational view of the bushing and bushing container similar to that of FIG. 12D; and FIG. 22E shows an enlarged cross sectional view of a portion of the apparatus of FIG. 22C. As best seen in FIGS. 22A and 22B, this implanted device is a thread-in assembly.

FIGS. 23A1-23B show views of anchors according to various embodiments of the present invention. FIG. 23A1 shows an exploded view of an anchor incorporating a tapered, locking, bushing container; FIG. 23A2 shows a side elevational, perspective view of an assembled anchor of FIG. 23A1; FIG. 23B shows a side elevational, perspective view of an assembled anchor according to another embodiment of the present invention, and using a set screw concentric with the axis of the bone anchor.

FIGS. 23 and 24 shows various means for locking a separable bushing onto a device, including by use of taper locks (FIG. 23A), concentric set screws (FIG. 234B), and non-concentric set screws (FIG. 24).

FIGS. 25A1-25A3 and FIGS. 26B1-26D show anchors according to various embodiments of the present invention. FIGS. 25A1-25A3 show one anchor assembled in a side elevational view (FIG. 25A1), a cross sectional view partly disassembled (FIG. 25A2) and a cross sectional exploded view (FIG. 25A3), FIGS. 26B1-26B2 show a different anchor in side-by-side side elevational views, external and assembled (FIG. 26B1) and cross sectional (FIG. 26B2), FIG. 26C shows an exploded side elevational view of a portion of the assembly; and FIG. 26D shows a cross sectional, exploded, partly assembled view of the anchor. In various embodiments the set screw can be external, such as shown in FIGS. 25A1-25A3, or can include a C-clip as shown in FIG. 26D.

FIG. 27A shows a top, side perspective view of the anchor attached to a spine; FIG. 28B shows an exploded, side perspective view of the apparatus of FIG. 27A; FIG. 28C is a cross sectional view of the assembled anchor of FIG. 27A; and FIG. 28D is a side, top, perspective exploded representation of the apparatus of FIG. 27A. Various embodiments include a lower bushing (fabricated from or coated with a polymer, metal, or ceramic) that is built into or inserted into a BandLoc-type of tool head, with an external cap that captures a top bushing element, and compresses the band upon assembly.

FIG. 29A shows a top, side perspective representation of the assembled anchor; FIG. 29B shows a top plan view of the apparatus of FIG. 29A; and FIG. 29C is an orthogonal, side elevational view of the apparatus of FIG. 29B. Various embodiments, one of which is depicted in FIGS. 29A-29C include cross linked polymer bushings with spherical features, although yet further embodiment contemplate bushing with hard surfaces, such as comprising metal or ceramics. The attachment or supporting device can include spikes to prevent rotation after implantation. The angle and height of the rod aperture can be adjusted by rotation of the bushing container 56.

FIG. 30 is a side, top, perspective view of the assembled anchor; and FIG. 31 is a top, side, exploded view of a portion of the apparatus of FIG. 30. In some embodiments, the flexible band can be aligned with the axis of the rod. Still further, yet other embodiments contemplate that a polymer bushing within a metal sleeve is used to transmit a compressive load onto the band. Some embodiments include that the banded anchor allows the rod to slide without the rod sliding against the band. Still further embodiments include a band and anchor that contains a polymer bushing or any other low friction interface (as one example, polished CoCr or biologically acceptable ceramics). In some embodiments the surgeons can wrap wires/tapes/bands around the bone and rod to create a sliding construct. Some of these embodiments us a dedicated sliding interface for the rod.

FIG. 32E is a side, bottom perspective, exploded representation of a portion of the apparatus of FIGS. 19A-19D; FIG. 32F is a bottom plan view of the assembled apparatus of FIG. 32E; FIG. 32G is a front, bottom perspective, exploded view of the apparatus of FIG. 32E.

FIG. 33E is a side elevational, cross sectional representation of the apparatus of FIGS. 20A-20E, with an alternative second bushing; FIG. 33F is a side elevational, cross sectional representation of the apparatus of the FIG. 33E, and orthogonal to FIG. 33E. FIG. 33G shows an enlargement of the apparatus of FIG. 33F after the head 82c of the attachment device has been popped-in to bushing **74*a*, with the assembled bushing being pushed into pocket 28*d***.

FIG. 34A is a side, top, elevational exploded view of the anchor; FIG. 34B is an assembled view of the apparatus of FIG. 34A; FIGS. 34C1-34C2 show end and side elevational views, respectively, of the apparatus of FIG. 34B; and FIG. 34D is a side elevational, cross sectional representation of the apparatus of FIG. 34A. Some embodiments pertain to an implant using a split bushing in an open configuration. As shown in FIGS. 34A-34D, this embodiment can utilize small polymer half-rings that can be sufficiently constrained and supported within a metal head. Still further embodiments contemplate the use of hard, rod-bearing surfaces comprising metal or ceramic. In some embodiments the profile height of the implanted device is about fifteen millimeters.

FIG. 35A is a side elevational, top perspective, cross sectional view of the assembled anchor; FIG. 35B is an external view of the anchor of FIG. 35A and a first instrumentation device; FIG. 35C is a cross sectional representation of the apparatus of FIG. 35B; and FIG. 35D is a cross sectional representation of the apparatus of FIG. 35C and including a second instrument. Various embodiments shown herein pertain to implantable devices that include options for removal, such as by includes "wings" in the pop-in retaining rings. These rings can be grasped by an instrument that will expand the ring for removal. As shown in FIG. 35A, wings are added to the pop ring, and cut outs are added to the tulip so as to minimize reaching underneath the tulip. As shown in FIG. 35B the inner sleeve includes flex tabs. As shown in FIG. 35C, there are teeth on the flex tabs that engage the wings on the pop ring. As shown in FIG. 35D, the instruments outer sleeve is placed over the inner sleeve so as to lock the teeth, and the instrument can be pulled up to release the pop ring, and pull the tulip from the screw shank.

FIG. 36A is a top, side, perspective view of the assembled anchor; FIG. 36B is a partial exploded view of the apparatus of FIG. 36A; FIG. 36C is a top, front perspective view of the apparatus of FIG. 36A; FIG. 36D is a cross sectional view of the apparatus of FIG. 36A; and FIG. 36E is an enlargement of a cross sectional view of an alternative construction for the anchor. Various embodiments shown herein include the use of a "non-rounded surface" for a polyaxial junction construction, including a protrusion on the bushing that assists in clocking the C-clip. The polymer bushing can be reduced onto the tulip head, and then secured with the C-clip for an overall profile relative to the bone surface of about sixteen millimeters.

FIG. 37A is a top, front, perspective view of the assembled anchor; FIG. 37B is a top planar view of the apparatus of FIG. 37A; FIG. 37C is a side, front, top perspective partially exploded view of the apparatus of FIG. 37A; and FIG. 37D is a side elevational cross sectional representation of the apparatus of FIG. 37A. Still further embodiments shown herein pertain to a closed anchor, having a slide-loading, self-retaining polymer bushing that is retained by live-hinged tabs. In some embodiments the implanted device has a profile of less than sixteen millimeters.

ELEMENT NUMBERING

Figure 1:
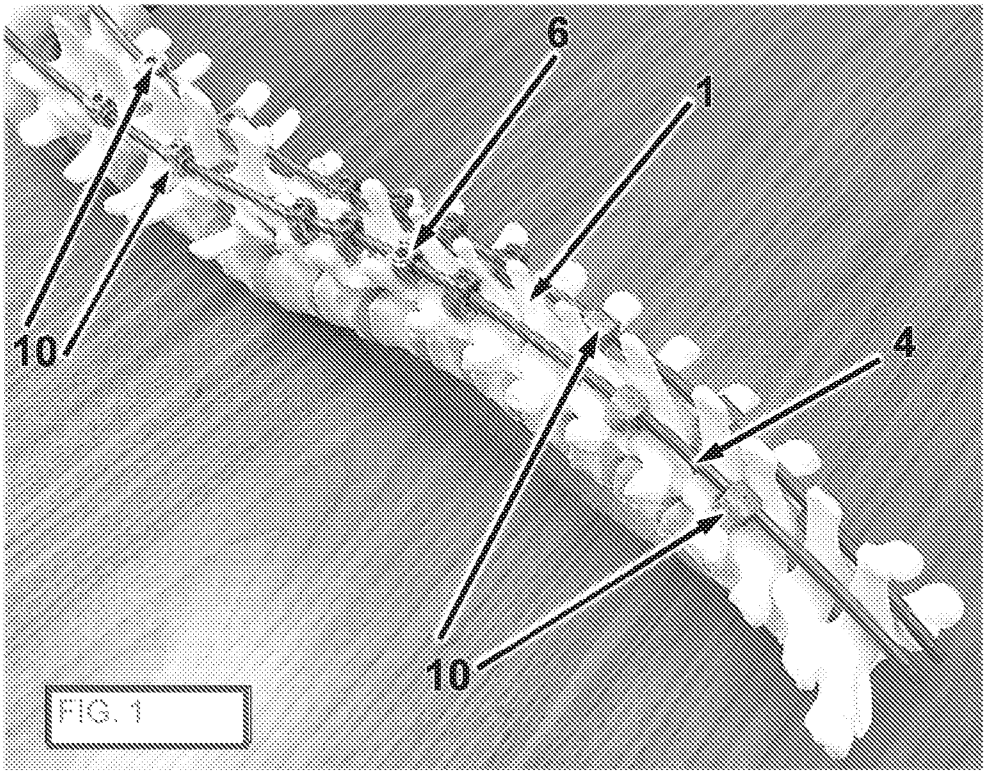
FIG. 1 is a top, side perspective view of a model of a spine having a pair of rods attached to the spine according to one embodiment of the present invention.

The following is a list of element numbers used with all of the embodiments, and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 1 | spine model |
| 2 | vertebra |
| a | spinous process |
| 4 | rod; rigid or flexible; also tether |
| a | circular |
| b | non-circular |
| b1 | height |
| b2 | width |
| c | axis |
| 6 | restraining anchor; fixating |
| 10 | guiding anchor |
| 20 | head |
| a | 1st end, device placement |
| b | 2nd end, bushing placement |
| 22a | threads for set screw |
| b | groove, |
| c | threaded post |
| d | unthreaded aperture |
| 24 | cavity |
| b | internal |
| c | external (platform) |
| d | annular; circumferential |
| e | non-cylindrical; oblong; oval |
| 26 | bushing or bushing container retention feature |
| a | groove, abutment; recess |
| b | locking cantilever spring; live hinge |
| c | opposing arms of head; tulip |
| d | bushing container interface |
| e | side opening |
| f | top opening |
| 27a | ring retention groove |
| b | insertion slit, aperture |
| 28 | supporting device junction pocket |
| a | internal shape |
| b | cylindrical, circular |
| c | spherical |
| d | pop-in, upper pocket |
| e | threaded aperture |
| f | tapered |
| g | cutouts for retainer access |
| h | guiding features for sliding member |
| i | notches or ledges for sliding member |
| j | slots for sliding member |
| k | distal underneath extension |
| 30 | slidable member |
| a | projection |
| b | one-way latch |
| c | cantilever arm |
| d | device support latch |
| 32 | head to support device interface member |
| a | retention; pivotal |
| b | bearing support |
| c | retention; lockable |
| d | passage for locking wire |
| e | wings |
| d | distal aperture |
| 34 | $1^{st}$ bushing interface |
| a | cylindrical |
| b | spherical |
| c | non-cyl oval oblong |
| d | groove or apertures |
| e | lip or ledge |
| f | lateral opposing slots or grooves (external) |
| g | internal groove or slot |
| k | tapered; conical |
| 35 | insertion direction |
| a | rod relative to head |
| b | bushing relative to head |
| c | head relative to device |
| 36 | bushing container retention feature |
| 38 | bushing retainer |
| 39 | $2^{nd}$ bushing interface |
| 42 | set screw; bushing retainer |
| a | set screw external threads |

-continued

| | |
|---|---|
| b | set screw internal threads |
| c | c-clip |
| d | gap; slot |
| d | set nut |
| 43 | slot |
| 44 | flexible connector |
| a | rod loop |
| b | vertebra loop |
| c | connector retention device |
| 45 | threaded cap, compress flex conn. |
| 50 | bushing fabricated from or including a surface comprising a polymer, metal, or ceramic |
| a | separable matl. body |
| b | matl. formed, molded or coated |
| 51 | split bushing; bushing segment |
| b | button |
| p | proximal |
| d | distal |
| 52 | rod pathway |
| a | closed channel |
| b | opened channel |
| c | groove |
| d | intermediate point of smallest width of height |
| e | entrance or exit to pathway |
| 53 | bushing extensions outside of cavity |
| 54 | bushing insertion direction into head |
| a | top |
| b | side |
| 55 | tab |
| 56 | bushing container; bushing support; rod-bearing surface of head |
| a | head retention feature; projection |
| b | opened support arms or saddle |
| c | tapered locking arm |
| d | extension member (overhanging) |
| e | ring; sleeve |
| f | interface with supporting device |
| g | central passage |
| h | cavity extensions |
| i | outrigger aperture |
| j | thickened or strengthened portion of bushing |
| 57 | bushing container interface with set screw |
| 58 | bushing interface with bushing container; pocket; bushing external shape |
| a | cylindrical |
| b | spherical |
| c | non-cyl oval oblong |
| d | center |
| e | retention feature, ledge, pins |
| f | ring inner surface |
| g | bushing container to head interface |
| 59 | bushing container to supporting device interface |
| a | pocket |
| b | fissure |
| c | retaining ring |
| d | aperture |
| 60 | rod to bushing interface; internal shape |
| a | cylindrical |
| b | semi-spherical; curved |
| c | non-cyl; oval; oblong |
| c1 | height |
| c2 | width |
| d | center |
| 62 | int. - ext. relationship |
| a | centered |
| b | offset |
| 67 | set screw interface with bushing |
| 70 | support arm |
| a | first ring or enclosure |
| b | second ring |
| c | first ring axis |
| d | second ring axis |
| e | enlarged end |
| f | arm axis |
| g | rigid arm |
| 74 | 2nd bushing, |
| a | device to head |
| b | device to lock ring |
| c | support arm to head |
| d | split; fissure |

-continued

| | |
|---|---|
| e | socket for device junction |
| 80 | supporting device |
| 82 | device junction |
| a | external shape |
| b | circular, uniaxial |
| c | spherical, polyaxial |
| d | pop-in |
| e | fixed junction w/head |
| f | necked-down region for sliding restraint |
| 84 | bone screw |
| a | tip |
| b | threaded section |
| c | cannula |
| 86 | spikes, projections |
| 90 | instrument |
| a | inner sleeve |
| b | outer sleeve |
| c | teeth; projection |
| d | slits; flexible portion |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The Shilla concept involves placing traditional pedicle screws at the apex of the spinal curve and fusing that short portion of the spine. Guiding (sliding) anchors (pedicle screws with bushings or coatings that permit sliding of a rod) are placed at the top and bottom of the construct. The sliding anchors force the spine to grow along the "rails" established by the rods. The various designs shown and described herein include low-friction bushings, low-friction coatings, unique geometry, the use of screw, bands, and spikes to secure the tulip head to the vertebra, and modular component design.

In various embodiments shown herein, it is understood that some, but not all, of the following features will be shown in certain particular embodiments. However, it is understood that the present invention contemplates combinations that comprise any collection of the following features and their equivalents. These features and their equivalents are shown and described with respect to any of the figures shown herein.

With regards to the bushing assembly, this bushing can be attached onto a supporting device 80 with any of the following loading configurations: top load; tip load; two piece; slide load; integral; and/or multi-piece assemblies for integral bushings, as examples. Still further examples contemplated herein include rod-bearing surfaces comprising polymeric, metallic, or ceramic materials, and also such surfaces that are fabricated directly onto the cavity of head 20 and not necessarily part of a separable, installable bushing component.

With regards to the internal or external features of the bushing 50, the bushing can be contoured; oblong; modular oblong with options shown herein; spherical; and/or metal lined, as examples.

With regards to the design of the anchor head 20, various embodiments include: a traditional tulip; a modular tulip; a modular outrigger for traditional tulips (both medial/lateral and inline); modular outriggers for custom screws; and/or banded/pedicle hybrid options, as examples.

With regards to the support of the bushing 50 onto the supporting device 80, various embodiments include: a wrap-around saddle; side-locked junctions; pop-in junctions; polymer lined junctions; junctions lined with hard metallic coatings or ceramic coatings; threaded-through assemblies; and/or tapered junctions (esp. those that are not spherical), as examples.

With regards to the manner of retaining the bushing, various embodiments shown herein include tapered locks; concentric set screws; non-concentric set screws; snap teeth and live hinges; external set screws; and/or C-clips, as examples.

Figure 5:
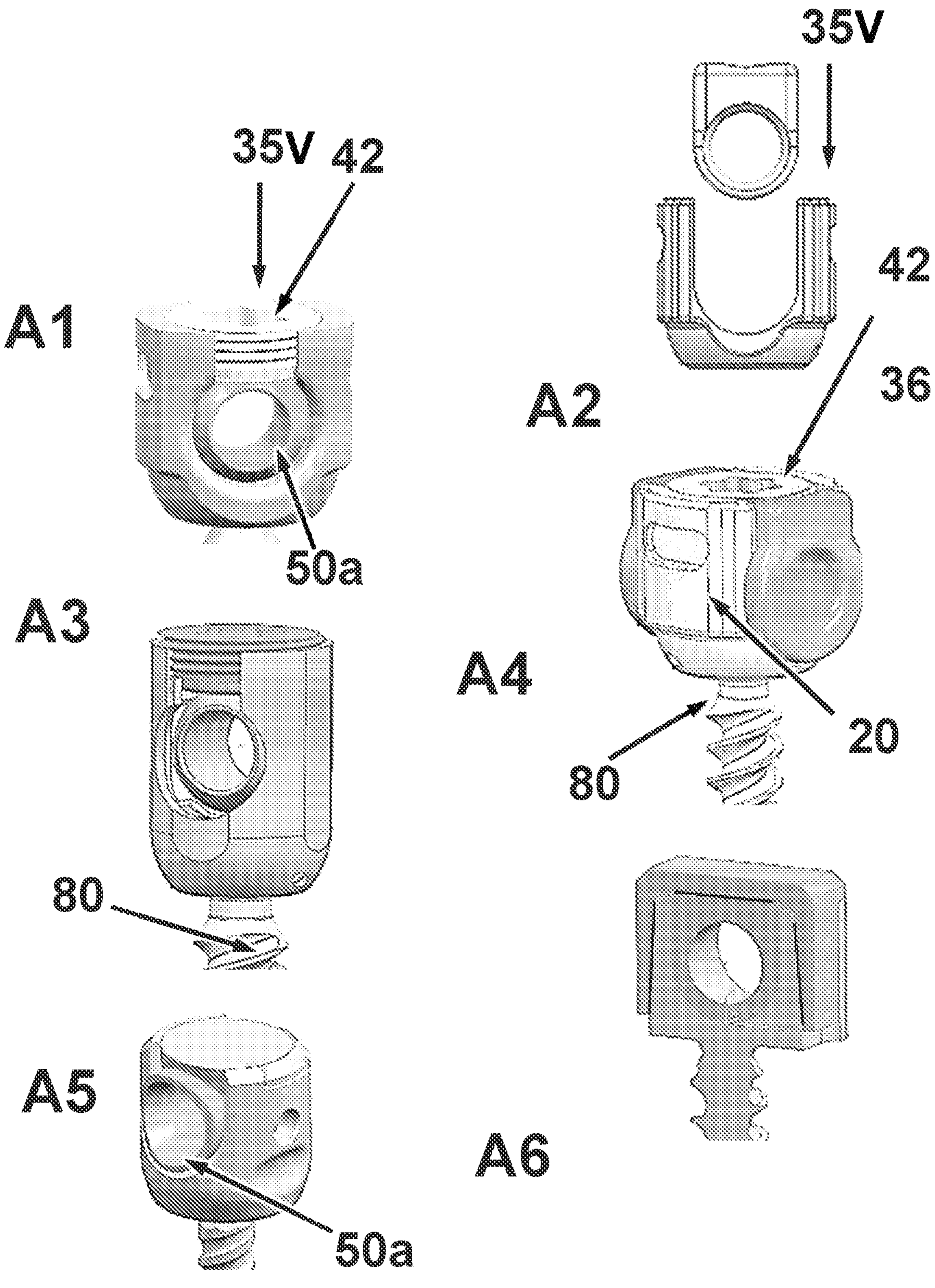
Figure 5:
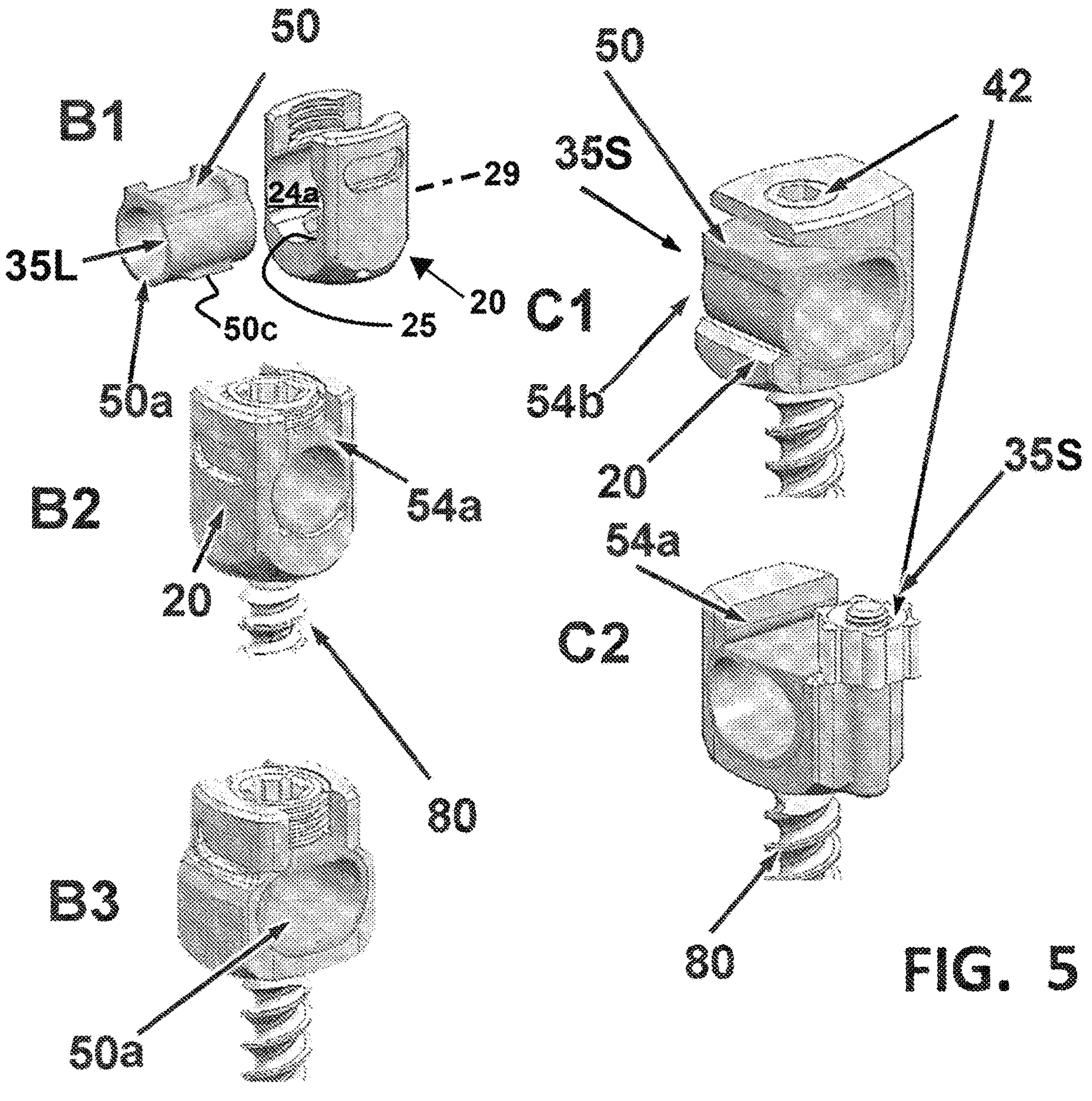
Figure 5:
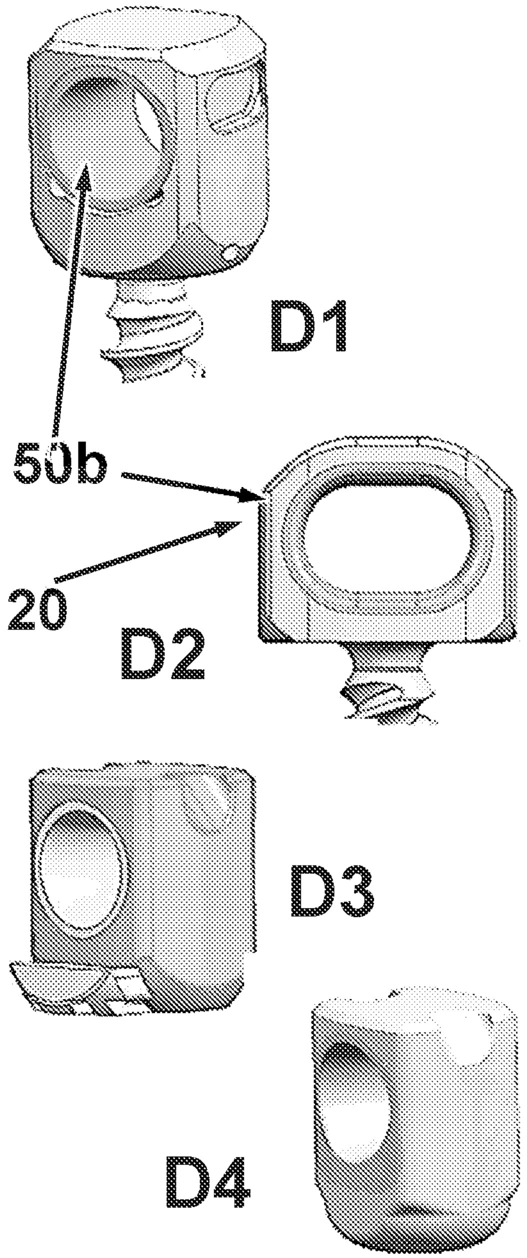

FIG. 5 presents a plurality of embodiments of guiding anchors 10, wherein the various heads 20 and bushings 50 are presented with regards to respective directions 35V, 35L, 35S from which the bushing 50 is inserted into the head 20. In FIGS. A1 to A6, the direction of insertion of the bushing is from a topmost end 20*b* of the head in a direction 35V toward the device end 20*a* (i.e., the end of the head to which the supporting device 80 is coupled). FIGS. B1, B2, and B3 shows various embodiments of heads 20 in which the bushing 50 is inserted in a lateral direction 35L relative to the end of the head that couples to the supporting device 80. In FIGS. B1 and B2, the bottom of the cavity 24*a* formed by the head 20 includes a slot 25 parallel to the rod axis 29, and the bushing 50 includes a surface 50*c* having a shape complementary to a cross-sectional shape of the slot 25, such that the bushing surface 50*c* and the cross-sectional shape of the slot 25 are adapted and configured to cooperate to limit rotation of the bushing within the cavity 24*a* about the axis 29. FIGS. C1 and C2 shows a pair of embodiments in which the bushing is inserted along an insertion path 35S that is neither parallel nor perpendicular to the orientation of the head 20. FIGS. D1 to D4 present various embodiments in which the bushing is molded integrally with the head, or molded integrally into the container, with the container being slid into the head.

Figure 6:
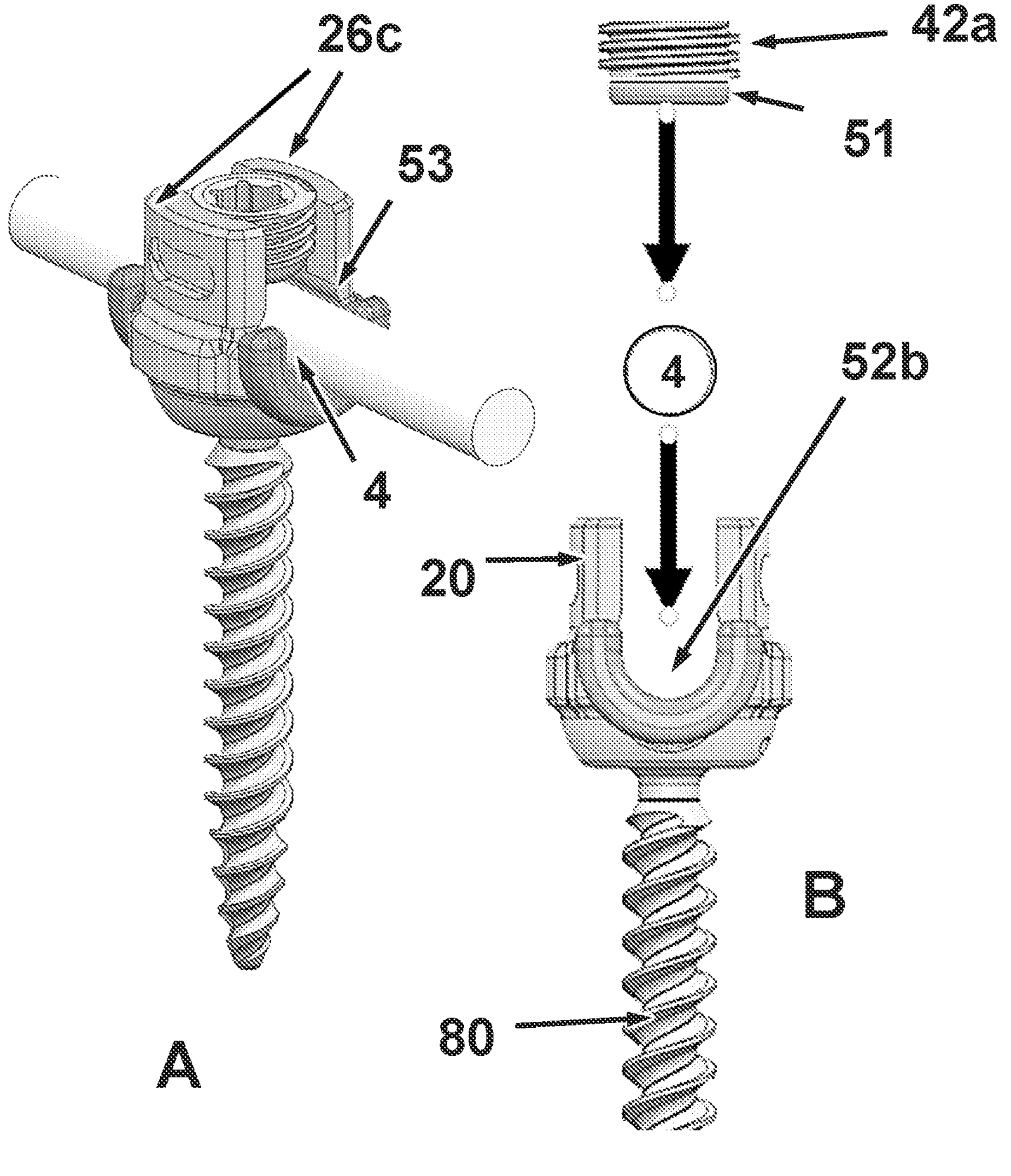
Figure 6:
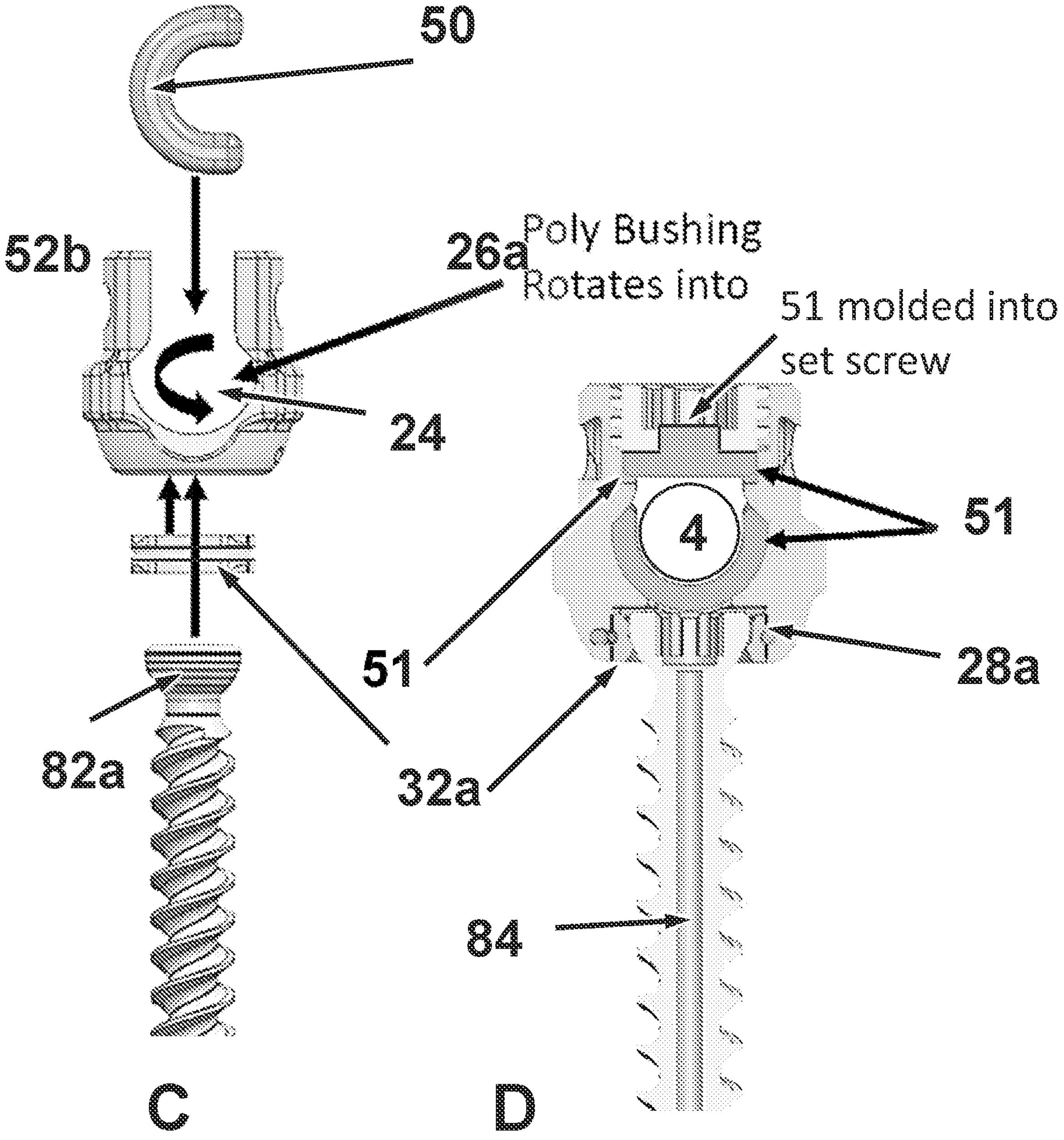

FIG. 6 shows a guiding anchor 10 that includes a bushing assembly 50 that includes a rod pathway 52*b* that is an open channel. A bushing segment 51 is coupled to the bottom of a set screw 42, creating surfaces surrounding the rod that are fabricated from a polymer material, although ceramic and metallic materials are also contemplated for the bushing segment.

FIG. 6A shows an assembled anchor 10 supporting a circular spinal rod 4. FIGS. 6B, 6C, and 6D show partly assembled, exploded, and cross sectional views of the anchor 10 of FIG. 6A.

Referring to FIG. 6C, it can be seen that anchor 10 in one embodiment includes a supporting device 80 preferably comprising a threaded bone screw having a rounded external shape that is adapted and configured to coact with a retention device 32*a*, such that the assembly of junction 82*a*, retention member 32*a*, and the device junction pocket 28*b* results in an attachment of head 20 to supporting device 80 that permits relative pivoting. In some embodiments, a portion of a wire (not shown) is inserted into the annular channel that surrounds pocket 28*a* and device 32*a*, preventing removal of supporting device 80.

Referring to FIG. 6C, it can be seen that head 20 includes a pair of proximally extending opposed, threaded arms 26*c* that define between the arms a cavity 24. Referring to FIG. 6C, it can be seen that cavity 24 includes one or more bushing retainer features 26*a* that assist in retaining bushing 50 within cavity 24. In the embodiment shown in FIG. 6, it can be seen that the retention feature 26*a* includes a pocket that is wider than the distance between opposing faces of arms 26*c*. In some embodiments, bushing 50 has a C-shape, and is inserted into cavity 24 sideways. Once the bushing is placed at the bottom of cavity 24, the bushing is then rotated so that the open portion of the C-shape faces in a proximal direction and forms the rod pathway 52*b*.

Referring to FIGS. 6B and 6D, it can be seen that anchor 10 includes an externally threaded set screw 42*a*, the bottom of which includes a bushing segment 51. Referring to FIG. 6D, it can be seen that once set screw 42*a* is tightened into arms 26*c*, that bushing segment 51 places an upper limit on the rod pathway 52*b*. In some embodiments, tightening of set screw 42*a* results in compression of this underneath bushing against the top of rod 4. In yet other embodiments, the set screw bottoms out mechanically, such that there is little or no contact between bushing 51 and the top of rod 4.

Figure 7:
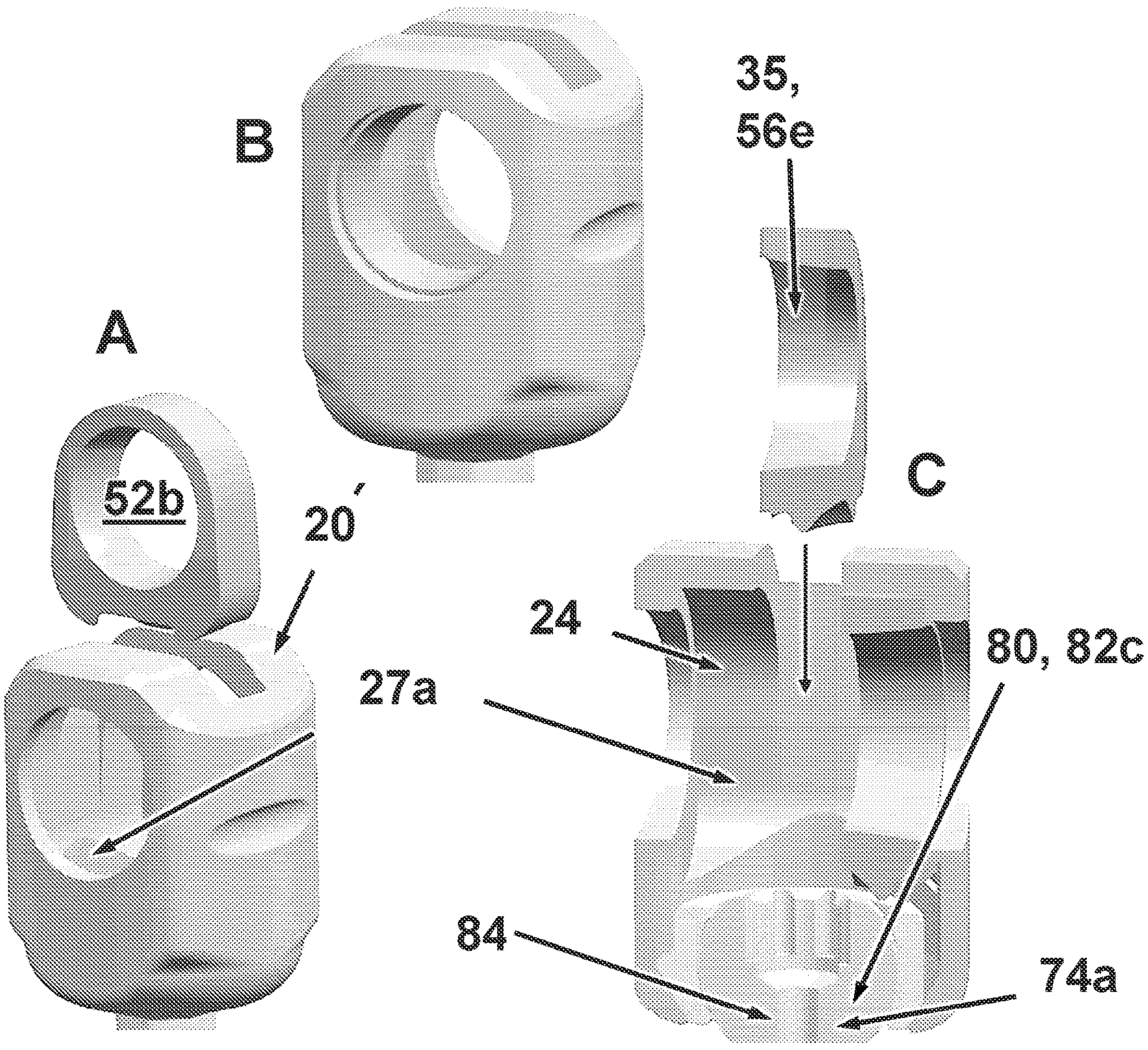
Figure 7:
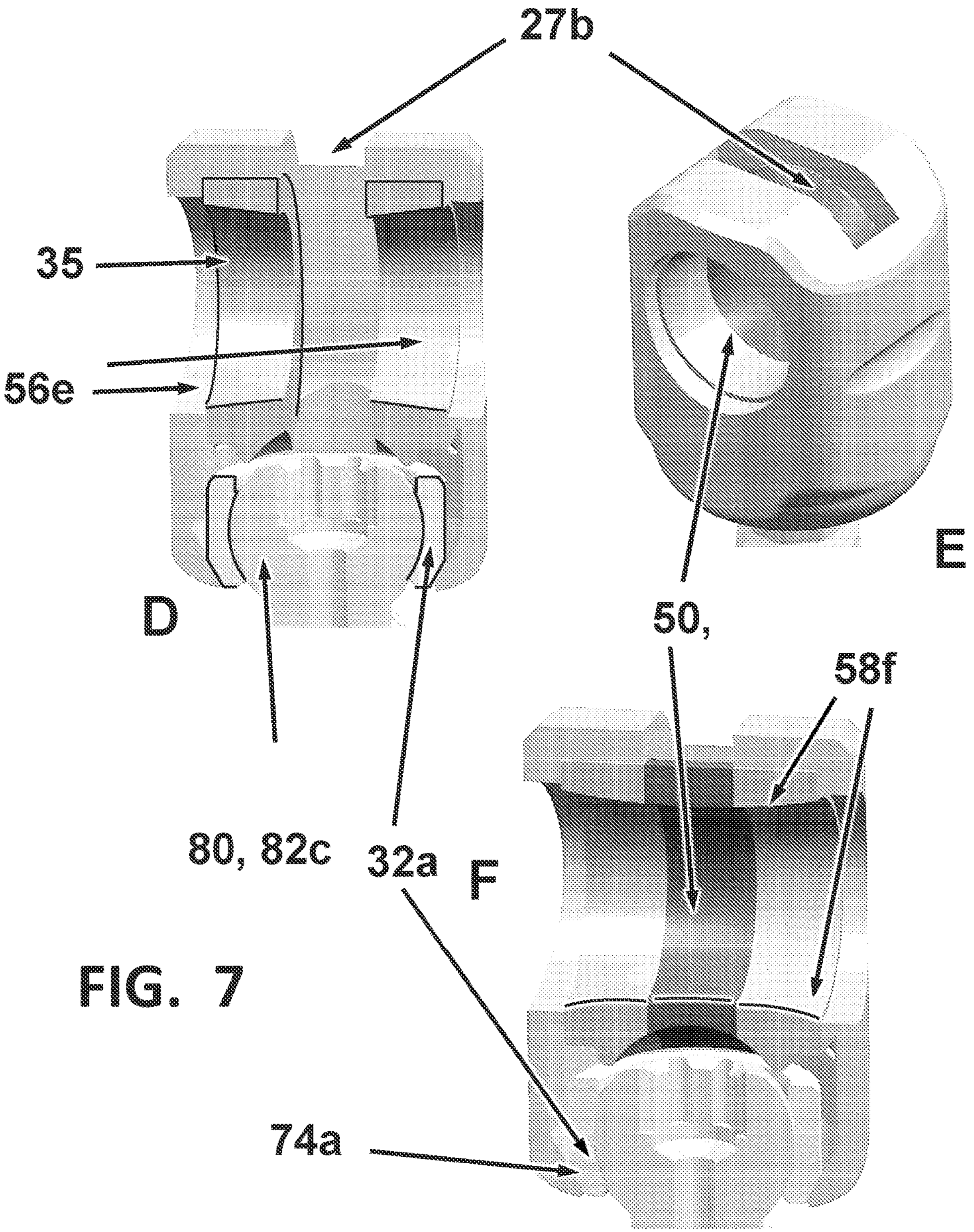

FIG. 7 shows various aspects of a guiding anchor 10 according to another embodiment of the present invention. FIG. 7 show various views of an anchor 10 in which the head 20 incorporates a bushing maintained in location by one or more bushing container rings 56*e*.

FIGS. 7A, 7B and 7C show the installation of bushing container rings 56*e* within head 20. FIG. 7A shows such a container ring that includes a central aperture that defines within it an opened channel 52*b* for clearance passage of a rod (not shown). In the embodiment shown, ring 56*e* is a complete ring-shape that includes a circular internal aperture 52*b*. However, it is understood that this central aperture can be of other shapes consistent with the primary placement of the rod being dependent upon the internal diameter of bushing 50, with the inner surfaces of rings 56*e* providing harder, more controlled limits on the internal movement of the rod within head 20. Referring to FIG. 7F, bushing container 56*f* in one embodiment includes an internal shape 58*f* that smoothly converges from a larger inner diameter to a smaller inner diameter in a direction from outside of head 20 toward the central bushing 50. The inner surface of bushing 50 is preferably circular or rounded (in cross sectional shape), and defines the closest fit to the rod within the pathway 52*b*.

Referring again to FIG. 7A, it can be seen that ring 56*e* includes one or more head retention features that coact with one or more ring retention features 27*a* to maintain ring 56*e* fixed in location. However, various other embodiments of the present invention include rings 56*e* that are placed within head 20, but are retained loosely and able to slightly move within the head after assembly.

FIG. 7C shows a cross section of a head 20 in which a first ring 56*e* has been inserted through a preferably central aperture 27*b*, and then moved sideways into the retention groove 27*a*. In some embodiments, there is a single retainer ring within a head 20. However, in the embodiment shown and as can be seen in FIG. 7D, there are a pair of rings 56*e* that have been inserted through slot 27*b*, and then laterally shifted into place on opposite sides of a central volume. FIG. 7F shows a bushing 50 that has been inserted through aperture 27*b* into the volume between rings 56*e*.

Figure 8:
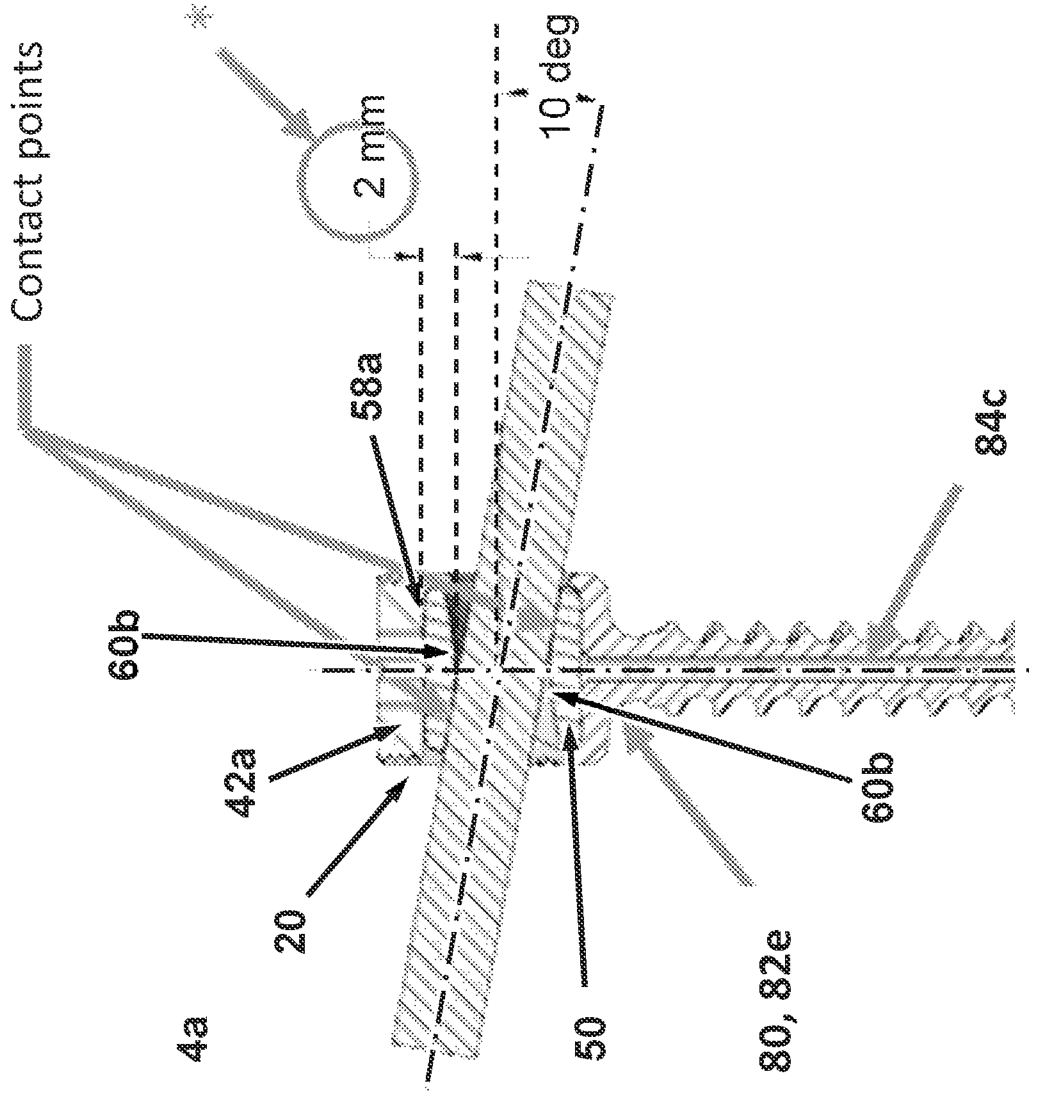
FIG. 8 is a side elevational cross sectional representation of an anchor 10 having a bushing with an internal spherical surface, and illustrating the articulation of the inserted rod. This device allows for angulation of the rod with preferably no moving parts except for the rod itself.

FIG. 8 presents a cutaway of a guiding anchor 10 in which a cylindrical rod 4*a* is received within a bushing 50 that has an internal shape 60*b* to the rod interface that is semi-spherical, and permitting angular movement of the rod of about +/−10 degrees relative to the centerline of the bushing pathway. In the embodiment shown, anchor 10 includes a head 20 that is in fixed relationship to device 80 by a fixed junction 82*e*. It is understood that head 20 shown in FIG. 8 could also be attached to a supporting device having a junction that permits uniaxial or polyaxial movement, although in the embodiment as shown, the additional rod pivotal movement that would be permitted by uniaxial or polyaxial attachments are instead provided by the internal shape 60*b* of bushing 50. In this manner, the overall height of anchor 20 from the bone contacting surface can be reduced by the fixed nature of junction 82*a*.

As shown, bushing 50 in one embodiment includes a generally cylindrical outer surface 58*a* that is received within the cavity 24 of head 20. Such a bushing can be inserted into head 20 in a direction generally along the axis of the rod, or in some embodiments can be inserted in a proximal to distal direction through a threaded aperture of head 20 that is later filled with a set screw 42*a*.

FIG. 8 shows that the internal rounded surface 60*b* (shown as semi-spherical) permits rod 4 to be generally located along the centerline of supporting device 80 due to the positioning of the narrow point of the bushing aperture at that centerline. In such embodiments and as shown, this internal close fit between the rod and the center of bushing 50 allows for pivoting motion, with one end of the rod contacting the upper internal surfaces of bushing 50, and the other end of the rod contacting the lower internal surface of bushing 50.

Figure 9:
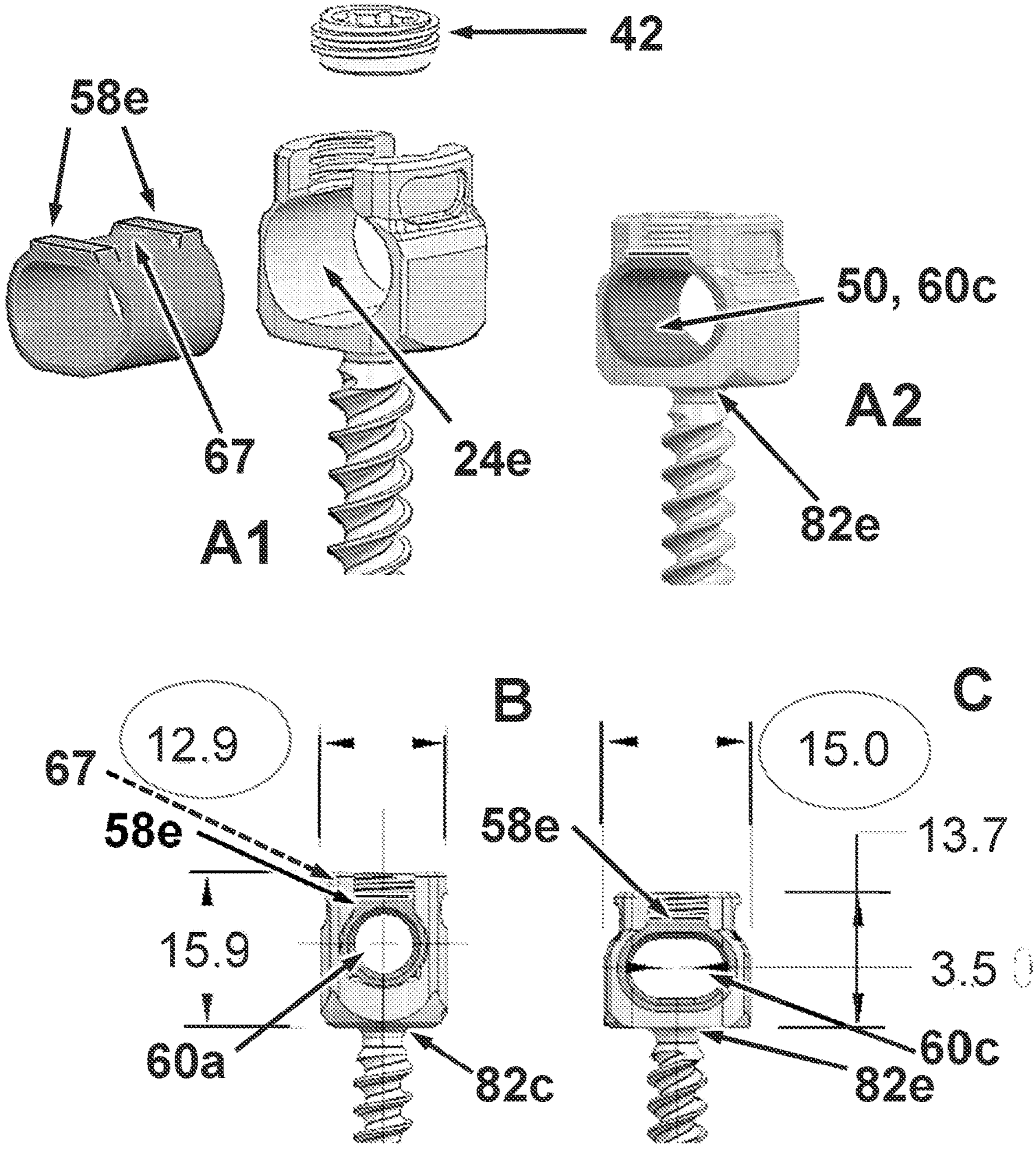
Figure 9:
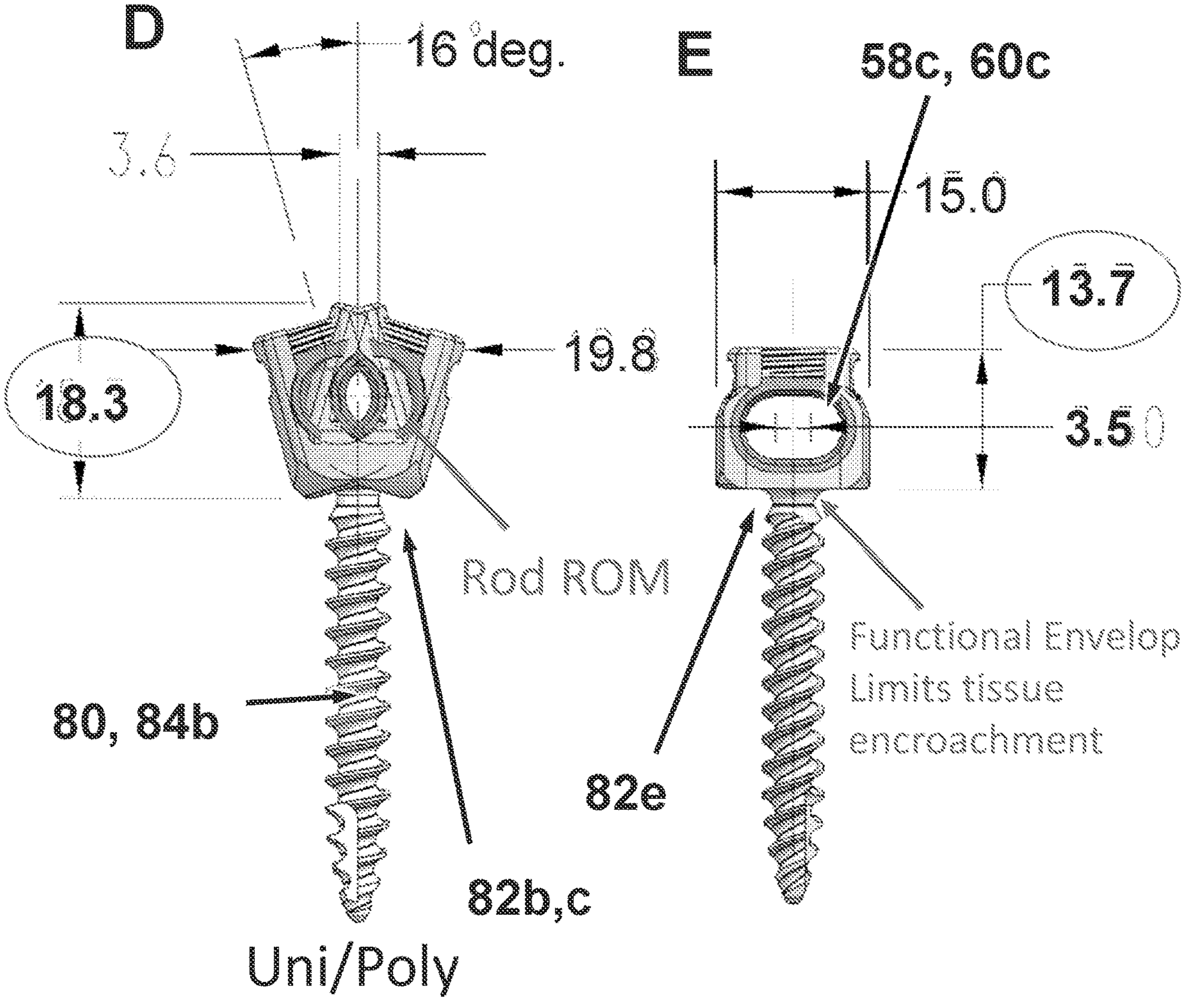

FIG. 9 present various views of a guiding anchor 10 that includes a bushing having a non-cylindrical internal shape for the rod interface. It can be seen on the right side E of FIG. 9 that the oblong or non-spherical shape 58*c*, 60*c* for the busing permits lateral and angular movement of a rod, while avoiding the encroachment into tissue of a uniaxial or polyaxial device attachment.

FIGS. 9A1 and A2 show a head 20 of an anchor 10 that is adapted and configured to receive within an elongated or oblong cavity 24 a bushing 50 having at least one retention feature 58*e* (and preferably two) located on the topmost (proximal) surface. Bushing 50 can be inserted through a lateral side of head 20, and as shown can be loaded in the same direction as the axis of the rod (not shown). In some embodiments, bushing 50 includes an interface 67 that is adapted and configured to receive therein the bottom face of a set screw 42 or similar device. Preferably, after insertion of bushing 50 into head 20 the pair of opposing ledges 58*e* extend above the central set screw interface 67, such that bushing 50 is trapped within cavity 24 by set screw 42. In the embodiment shown, supporting device 80 is coupled to head 20 by a fixed junction 82*e*. Although the fixed junction (of some embodiments, but not others) does not permit relative motion of head 20 relative to support device 80, the oblong or elongated rod interface 60*c* is adapted and configured to provide lateral motion of the rod (for example pure lateral motion, laterally pivotal motion, or a combination thereof).

Referring to FIGS. 9B and 9C, it can be seen that in some embodiments the anchor 10 shown in FIG. 9A (and reproduced in FIG. 9C) provides a lower overall height of the top of anchor 10 relative to the bone surface (i.e., about sixteen millimeters for the polyaxial screw of FIG. 9B; and about thirteen millimeters for the fixed screw of FIG. 9C).

Yet another trade-off between polyaxial and fixed support devices is shown in FIGS. 9D and 9E. FIG. 9D shows the pivotal head 20 of FIG. 9B, which can be in different embodiments uniaxial or polyaxial). It can be seen that the side to side pivotal motion results in a distal corner of head 20 moving downward toward the surrounding tissue. In contrast, the fixed nature of head 20 as shown in FIGS. 9E and 9C provides a fixed interface that minimizes tissue encroachment.

In further comparison of FIGS. 9D and 9E, it can be seen that FIG. 9D permits, in some embodiments, a pivotal motion laterally pivotal of about sixteen degrees, with one of the topmost corners of head 20 pivoting upward (in a manner analogous to the downward pivoting of the lower corner). In yet another comparison, the lateral (side to side) envelope of the anchor of FIG. 9D is about twenty millimeters, whereas the fixed lateral envelope of the anchor of FIG. 9E is about fifteen millimeters.

Figure 10:
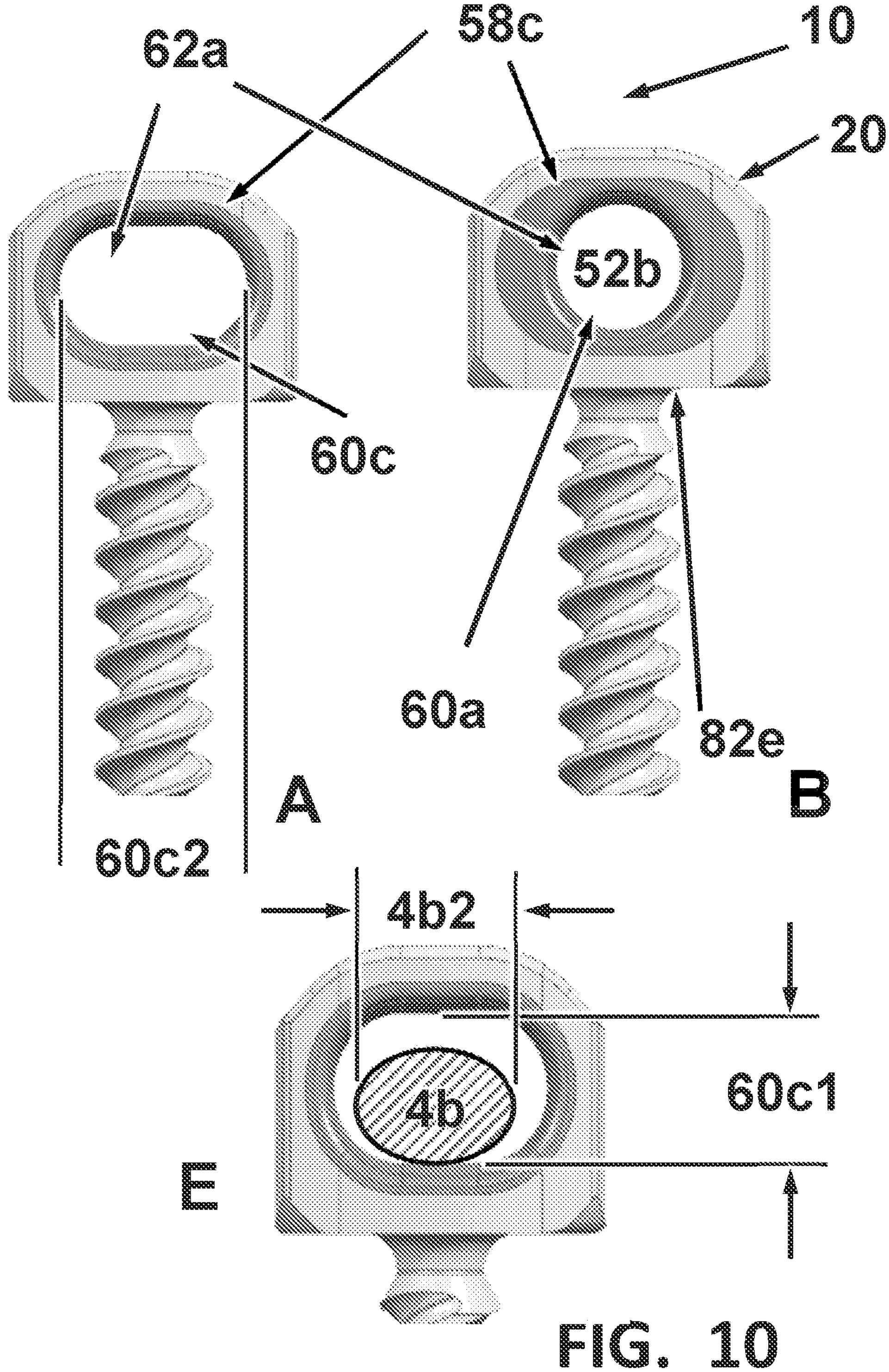
FIG. 10 show various anchors 10 with integral bushings.
Figure 10:
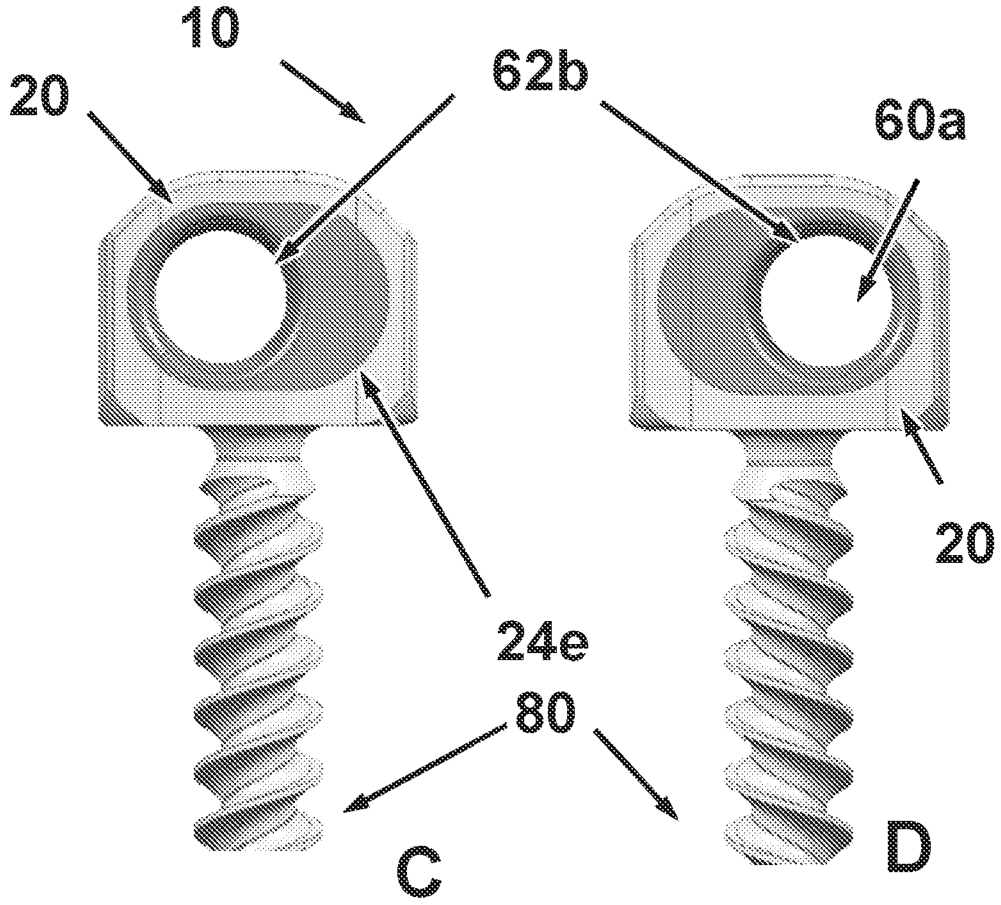

FIG. 10 show a plurality of guiding anchors 10 that include a bushing with a non-circular external shape that is preferably molded into the head 20. FIG. 10A anchor 10 includes a non-cylindrical rod internal interface 60*c* that permits lateral motion and angular motion of a rod (as well as the axial, guided motion). The other three anchors B, C, and D each include smaller rod interfaces (shown as cylindrical interfaces, by way of example only), with some of the internal rod interfaces being offset from the external head interface, and with two anchors in which the internal and external bushing shapes are generally centered. In some embodiments of the present invention, the anchors 10 of FIG. 10 illustrate a kit of anchors.

In each of the four embodiments shown, the head 20 and support device 80 are the same, each incorporating a device junction 82*e* that is fixed. However, the kit is further preferably provided with a plurality of different bushings 50. As can be seen in FIG. 10A, one bushing 50 incorporates a non-cylindrical rod interface 60*c*, such an oval or oblong interface, which permits lateral movement of a rod (lateral translation, lateral pivoting, or a combination of both). The bushing 50 of the anchor of FIG. 10B incorporates a generally cylindrical rod interface 60*a* that is generally centered within the oblong cavity 24*e*. In contrast, the bushings 50 of the anchors of FIGS. 10C and 10D include a generally cylindrical rod interface 60*a* that is shown with an offset 62*b* relative to the centerline of the supporting device. In some embodiments, the bushings of FIGS. 10C and 10D are identical, and simply inserted in a different direction to change the offset.

FIG. 10E depicts the embodiment of FIG. 10A shown supporting an oblong rod 4*b* having a width 4*b*2. Rod 4*b* is located within a non-circular bushing interface 60*c* having a height 60*c*1 that is less than the rod width 4*b*2. Therefore, bushing 60*c* within head 20 will limit any rotation of the rod within the rod pathway 2*b*. This limit is reached when the longest cross sectional distance of the rod touches the inner surface of the bushing.

Figure 11:
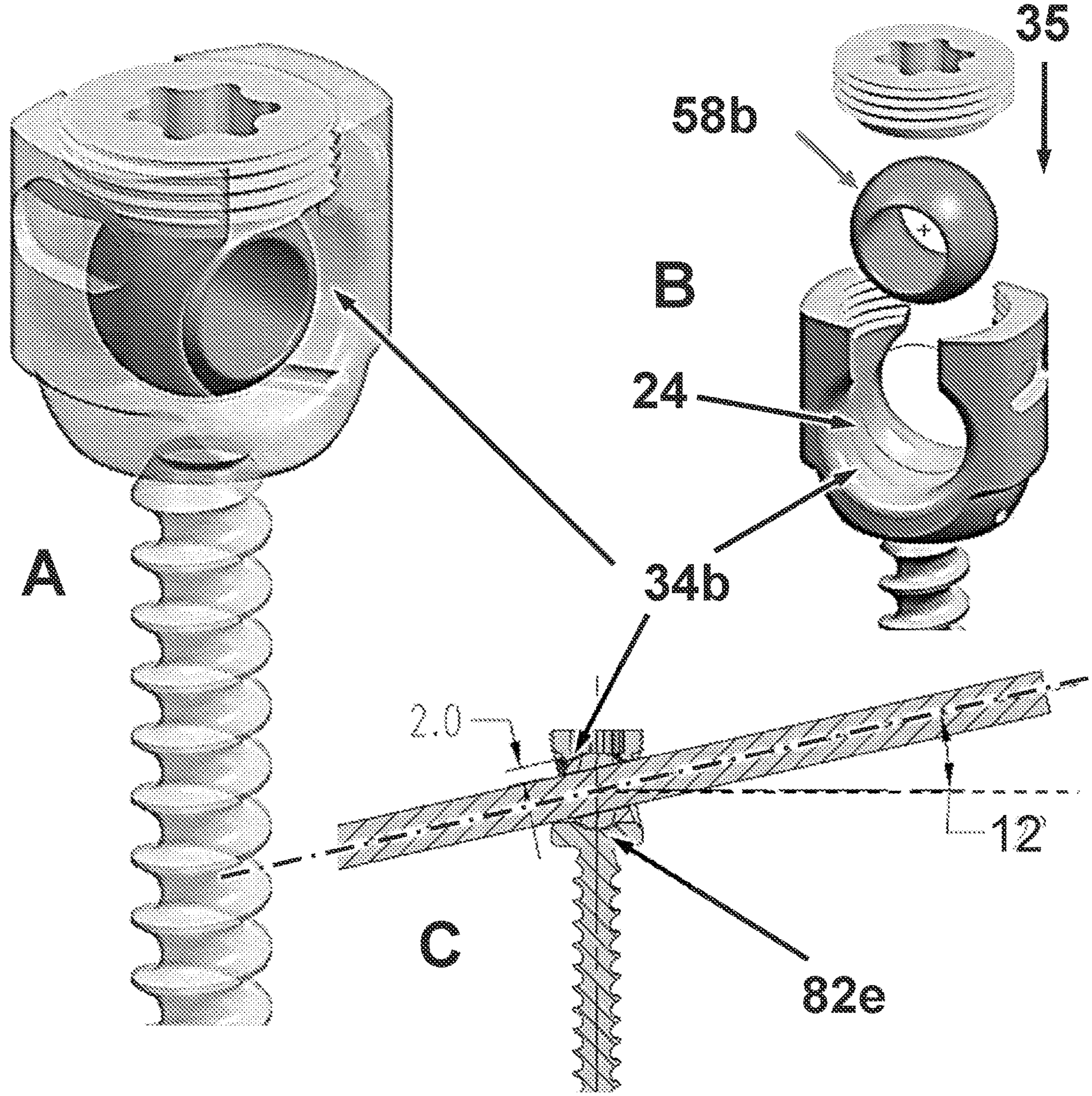
Figure 11:
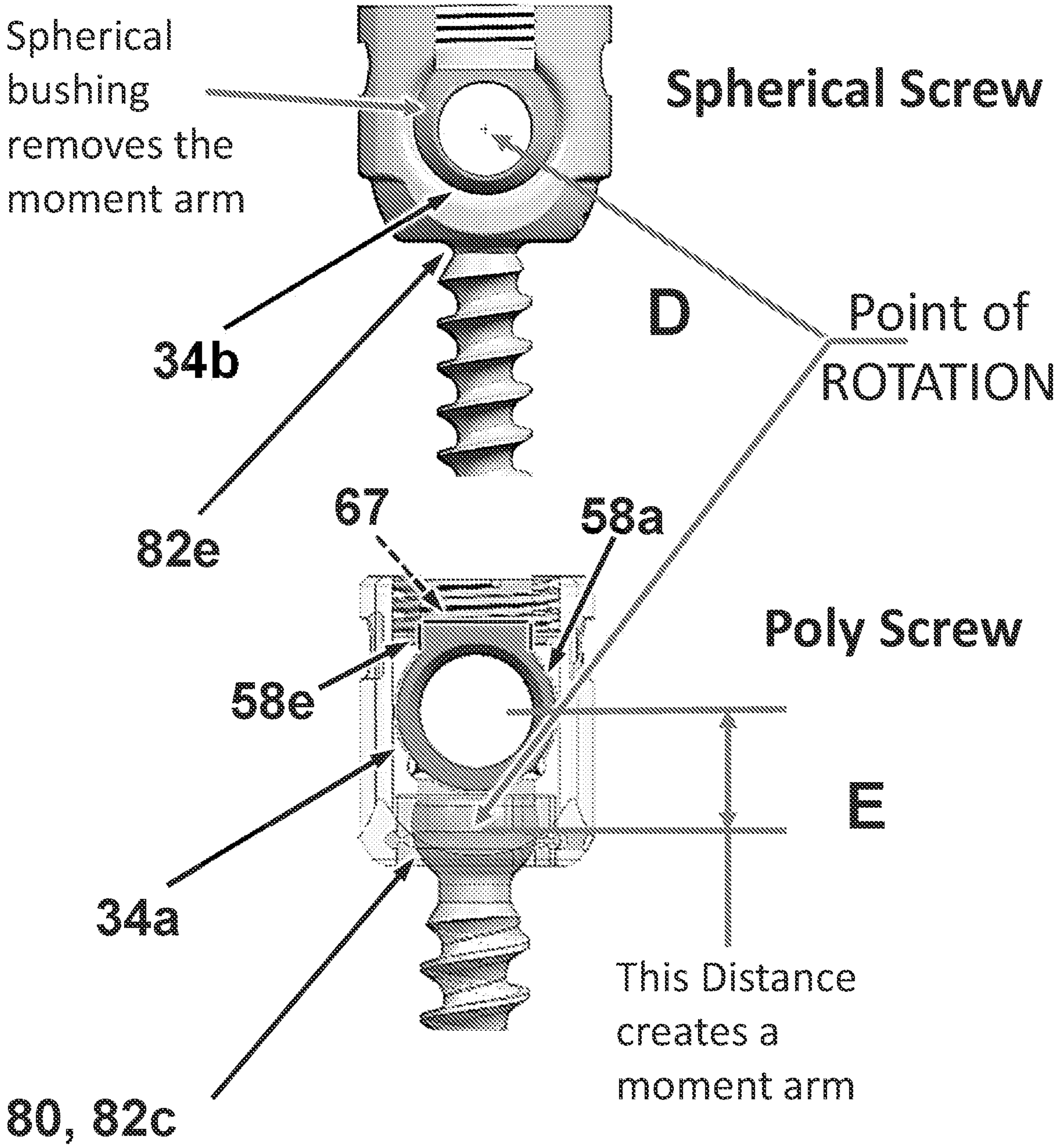

FIG. 11 shows a guiding anchor 10 that includes a bushing 50 having a spherical external shape 58*b* that is received within a spherical bushing interface 34*b* of the head 20. The right side of FIG. 11 compares head 20 in view D on top that is fixed to the device 80, and a head 20 at the bottom in view E that interfaces with the device by way of a spherical junction 82*c*. In the top device, the bushing is spherical relative to the head, whereas in the bottom device the bushing is fixed relative to head 20. It can be seen that the rotation point for the rod is different for the two different devices.

FIG. 11 show various views of a first anchor 10, and a view of an alternative anchor in FIG. 11E for comparison. FIGS. 11A and 11B show partially transparent and exploded views, respectively, of anchor 10. Anchor 10 includes a bushing 50 having a spherical head interface surface, and which is received within a spherically shaped head pocket 34*b*. In the anchor of FIG. 11C a rod can be pivoted about plus or minus twelve degrees vertically (as shown in FIG. 11C) and further pivoted laterally (i.e., in and out of the plane of the figure) plus or minus twelve degrees.

FIG. 11D shows the anchor of FIG. 11A compared to an anchor 10 of FIG. 11E that includes a cylindrical rod interface, but which includes a polyaxial junction 82*c* between head 20 and support device 80. It can be seen that the point of rotation of the rod in FIG. 11D is generally the centerline of the bushing 50. As a rod is urged to pivot, the sliding interface will occur between bushing 50 and pocket 34*b*. In contrast, in the anchor of FIG. 11E the bushing 50 is retained in fixed position by retention features 58*e* (in a manner similar to that for the anchor discussed in FIG. 9A), such that any pivotal urging of a rod located within bushing 50 of FIG. 11E would result in pivotal motion of the head assembly 20 relative to the center of the supporting device junction 82*c*.

Figure 12:
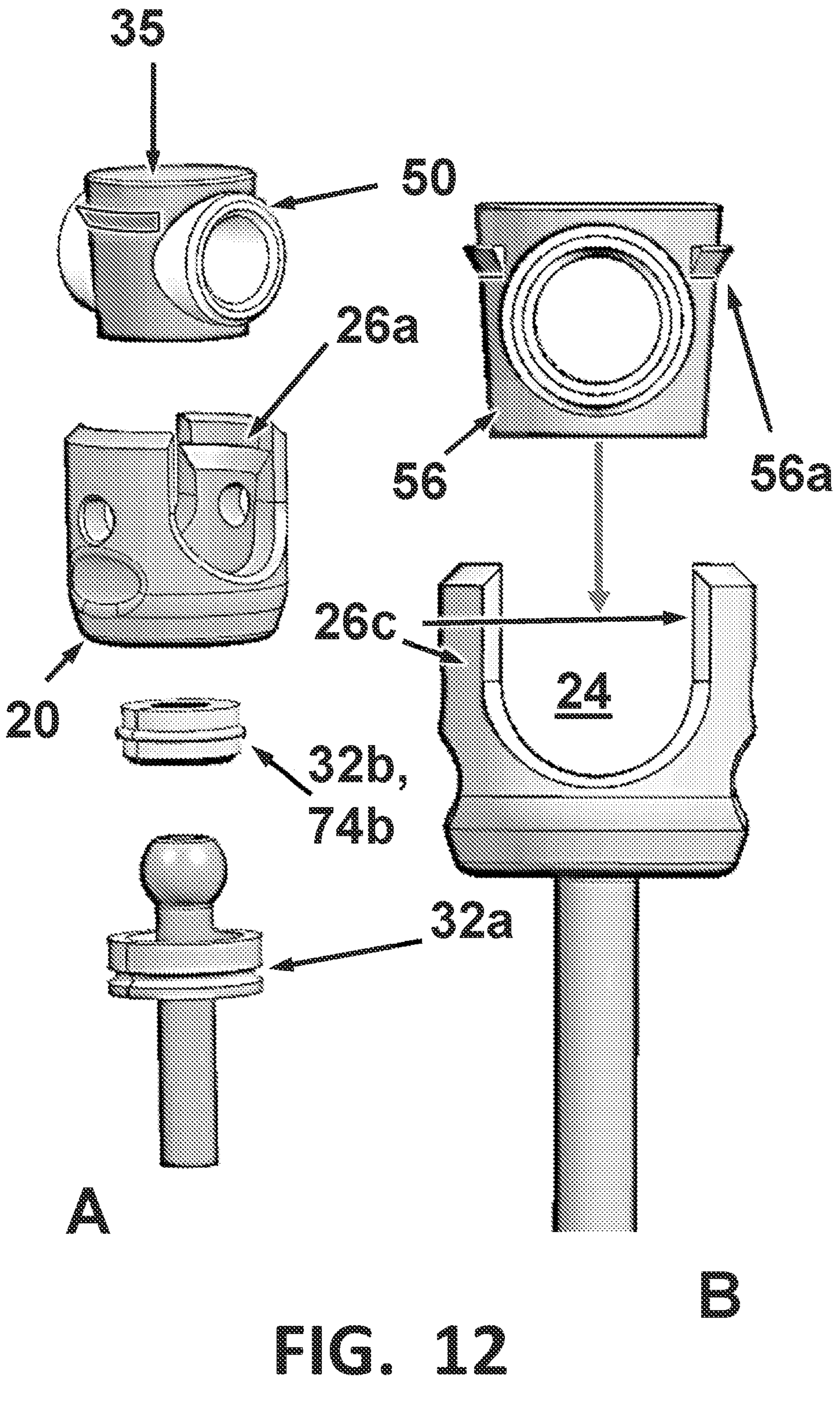
Figure 12:
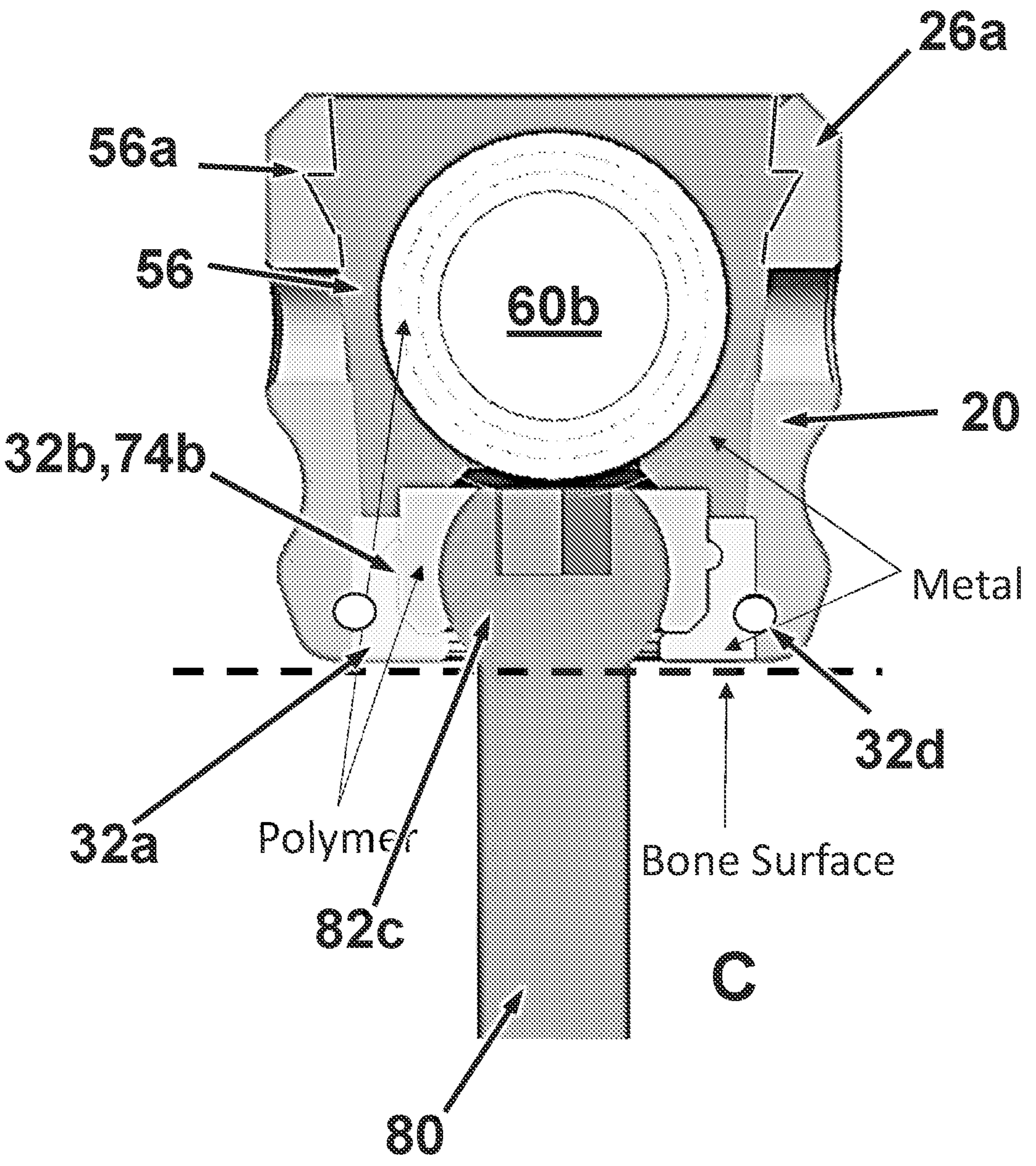
Figure 12:
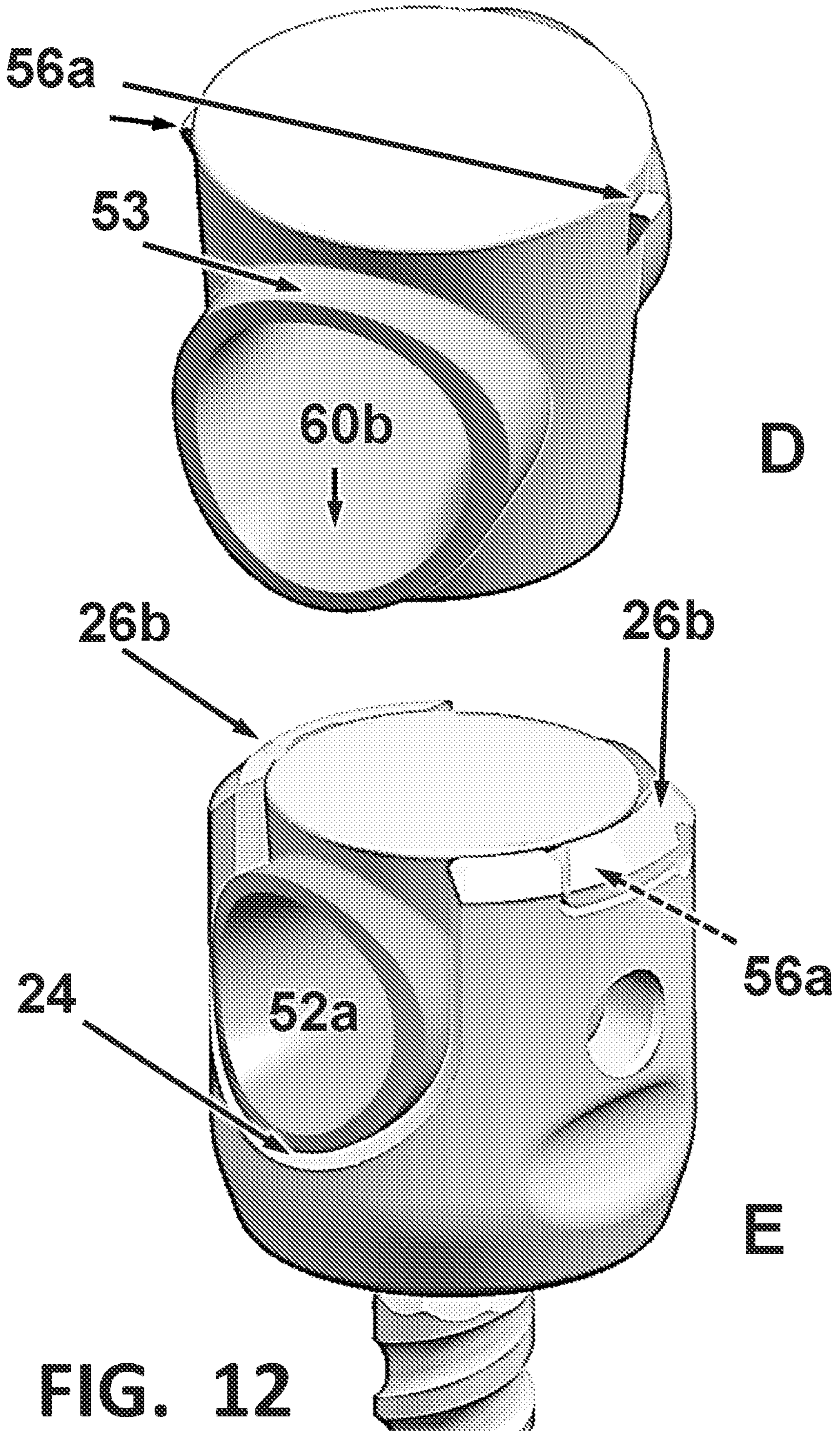
Figure 12:
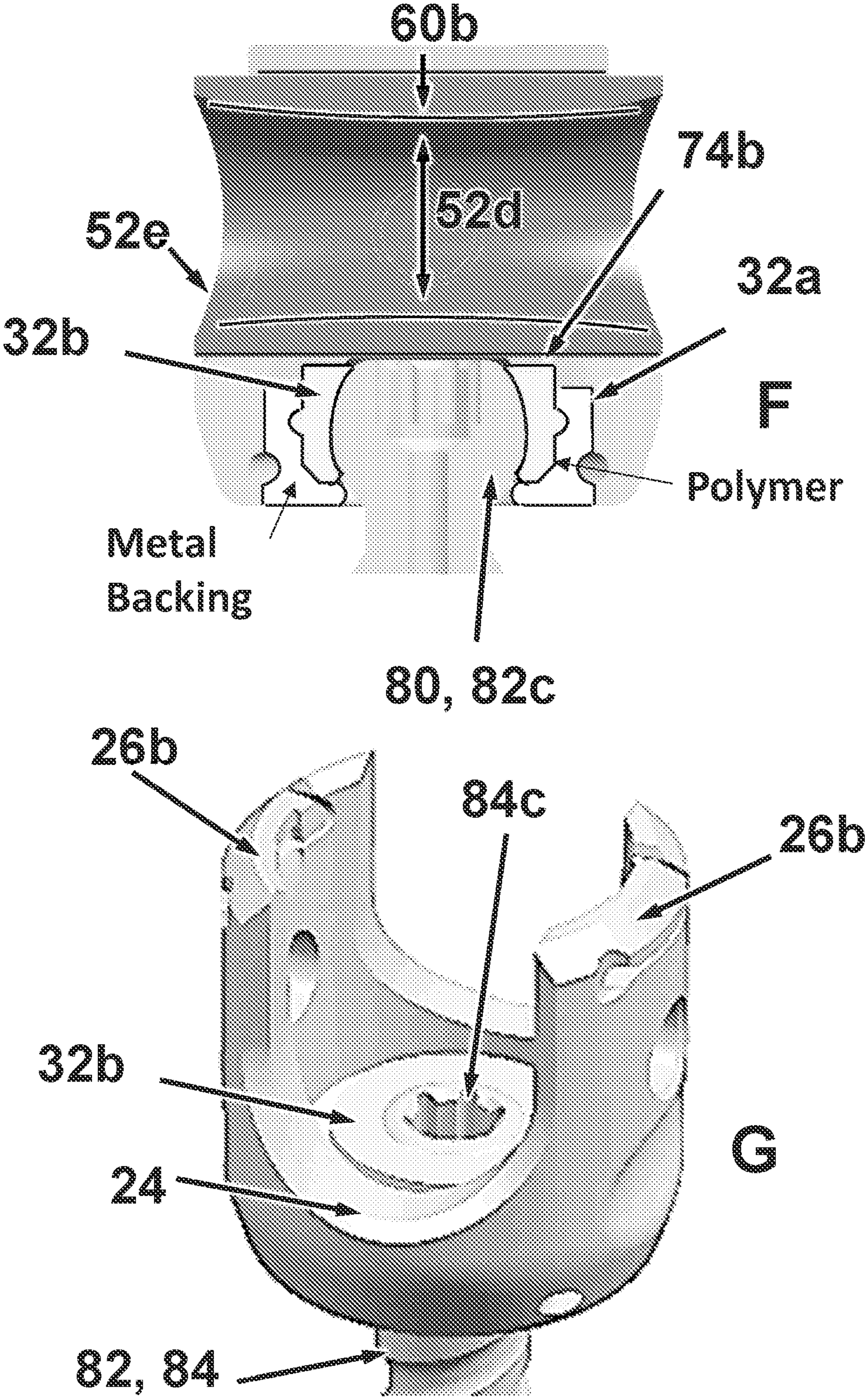

FIG. 12 shows a guiding anchor 10 according to various embodiments of the present invention. FIGS. 12D, E, F, and G shows a bushing 60 located within a container having a pair of protruding head extensions 56*a*. Referring to the bottom of the rightmost column, it can be seen that each of these features 56*a* interface with a corresponding cantilevered locking arm 26*b* of head 20. Referring now to FIGS. 12A, B, and C, it can be seen that in another embodiment one or more protruding features 56*a* can be received in corresponding grooves 26*a* of head 20, the insertion being accomplished by compressing together bushing 50 and head 20 such that the opposite arms 26*c* spread apart and then snap together, capturing the head retention features 56*a*. The cantilevered locking arm 26*b* of head 20 of FIG. 12E operates in a manner similar to that of the cantilevered locking arm shown in FIGS. 21B. and 27.

FIGS. 12A, 12B, and 12C depict various views of an anchor 10 according to another embodiment of the present invention. Comparing FIGS. 12A and 12D, it can be seen that a similar bushing container 56 and bushing 50 are used in each of the two different anchors. The bushing container 56 includes one or more retention features that are generally complementary in shape to retention features on head 20. Referring to FIG. 12A, head 20 includes a groove 26*a* that receives within it the retention features 56*a*, as shown in FIG. 12C. Whereas the anchor of FIG. 12D incorporates living hinges 26*b* into which the retaining features 56*a* are snap received, in the anchor of FIG. 12C can be located within groove 56*a* by compression of bushing container 56 into the cavity 24 of head 20, such that the retention features 56*a* are sufficiently resilient to compress inward, and then expand back outward into the groove 26*a*. As a further difference, it is further noted that the head retention features 56*a* of FIG. 12D have a generally small circumferential extent and are adapted and configured to fit into a pocket of cantilever arm 26*b* of similar size. In contrast, the retention features 56*a* best seen in FIGS. 12A and 12B have a more extensive circumferential extent, and in some embodiments extend generally from one side of the bushing aperture to the other side of the bushing aperture.

In still further embodiments, a variation of the bushing container and bushing of FIG. 12A can be coupled to a head 20 with a groove 26*a* by a bayonet-type connection. In such embodiments, the bushing 50 would not have the outward extensions 53 shown in FIGS. 12D and 12A. Instead, the ends of the rod pathway would be generally the same as the apertures of container 56. In such an embodiment, a modified bushing container 56 could be placed within cavity 24, and then rotated within the cavity such that the retention ledges 56*a* shown in FIG. 12A enter the grooves 26*a* from the open sides of cavity 24.

FIG. 12F shows a cross sectional shape 60*b* for the interface between the rod and the bushing 50, Preferably, in some embodiments the mid-section of bushing 50 has a smaller internal height and/or width 52*d* than the height and/or width of the open ends 52*e* of the bushing. Because of this shape, the intermediate section of the bushing acts as a loose fulcrum for any pivotal motion of the rod relative to the head. Still further, since the open ends are larger, there is less possibility of contact and abrasion of the rod against the bushing openings 52*e*.

FIGS. 12C and 12D further show the polyaxial coupling of head 20 to support device 80. Referring to FIG. 12C, it can be seen that head 20 includes a cylindrical pocket that is adapted and configured to receive within it a retention member 32*a*. Each of head 20 and member 32*d* include a portion of a passageway which can be aligned together and form an annular pocket 32*d* into which a locking wire (not shown) can be inserted. Retention device 32*a* includes within it a pocket having a shape that is generally complementary to the outer shape of a bearing support 32*b*. The supports 32*a* and 32*b* interlock with each other by way of this fitting of complementary shapes. Bearing 32*b* further includes an interior spherical recess that is preferably close fitting to the spherical ball junction 82*c* of support device 80. Preferably, bearing support 32*b* is either comprised of a material, or is coated with material, suitable for it to be a low friction bushing 74*b* for device junction 82*c*.

Figure 13:
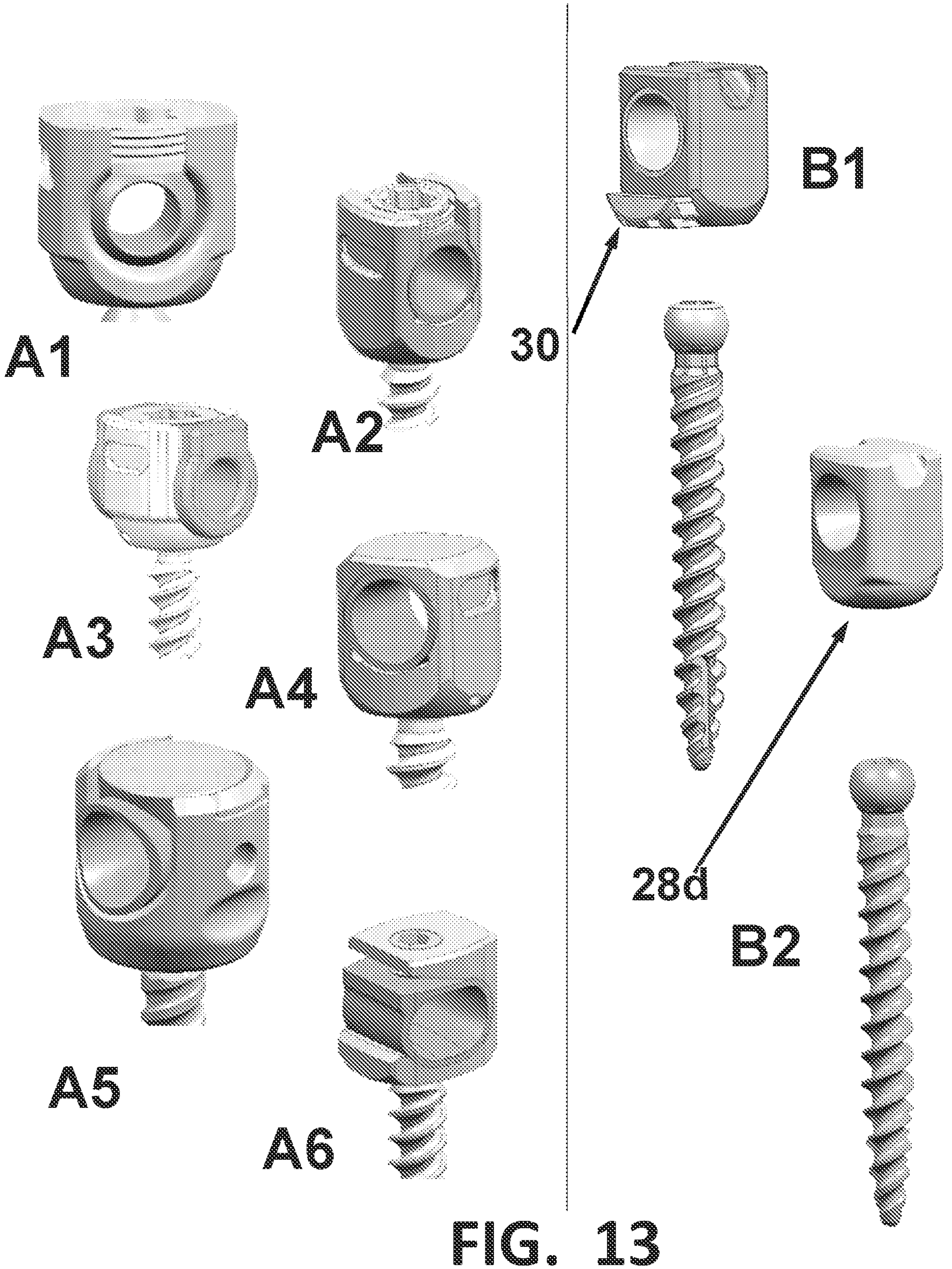
Figure 13:
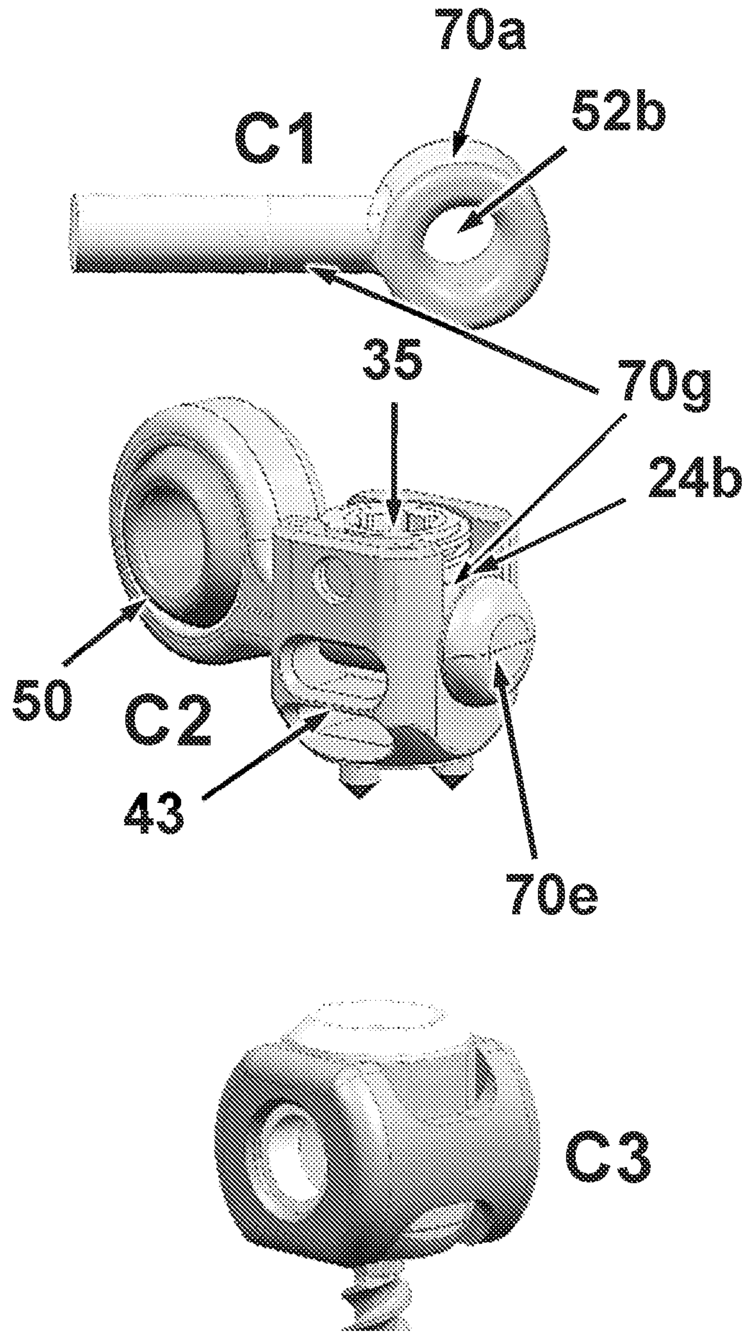
Figure 13:
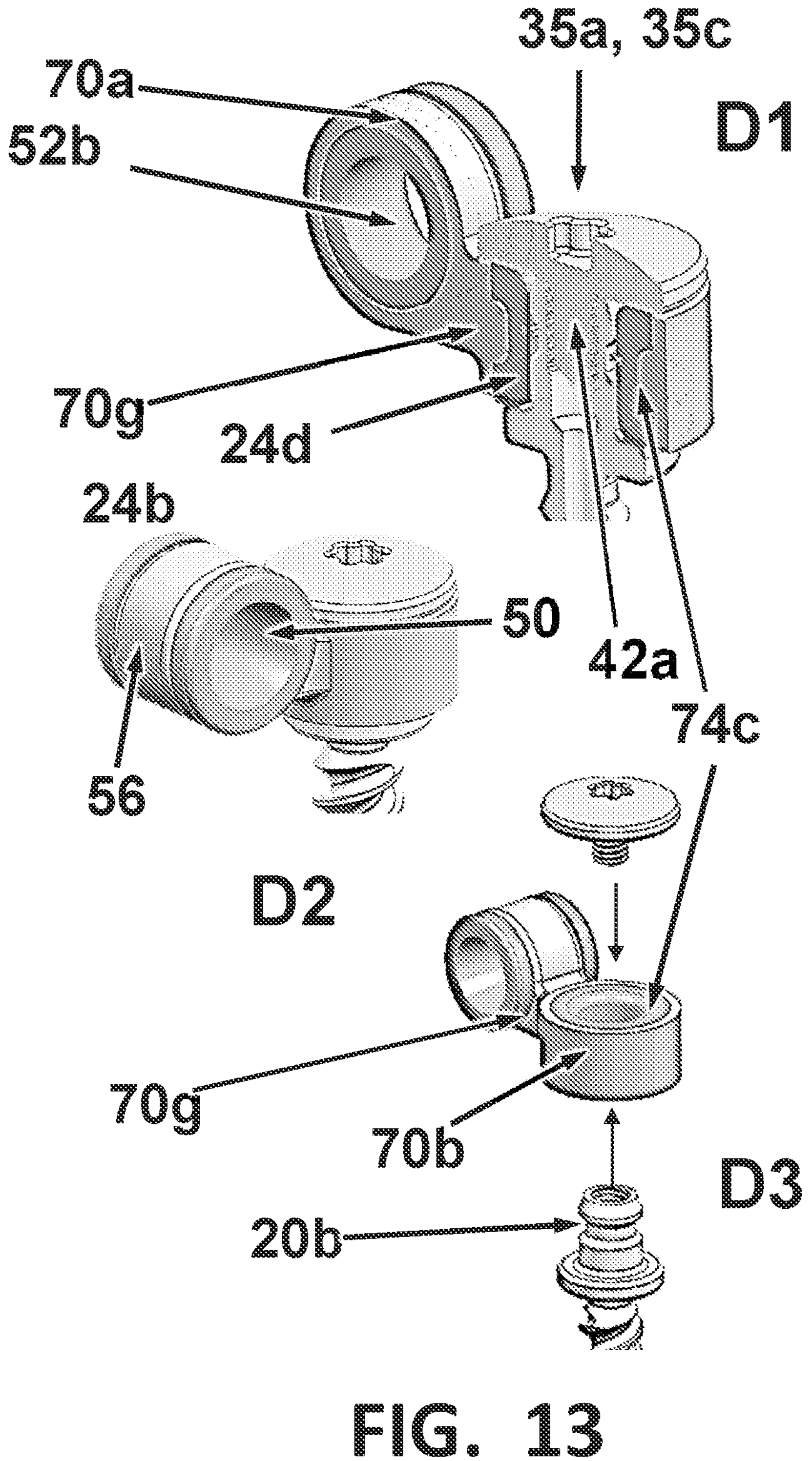

FIG. 13 shows various anchor designs according to various embodiments of the present invention. FIGS. 13B1 and B2 show a guiding anchor 10 that includes a pop-in head 28*d*. This embodiment is further discussed with regards to FIG. 20. FIGS. 13 C1, C2, C3, D1, D2, and D3 show various embodiments, some of which include bushings 50 that are supported by an arm, with the arm being connected to the head 20. In FIGS. C1, C2, and C3 it can be seen that the arm 70G is received vertically downward onto the head 20, with the outer surface of the arm being locked by a set screw within a laterally arranged cavity 24. In FIGS. D1, D2, and D3, it can be seen that the arm 70 includes a second ring 70*b* that is received vertically into a cavity 24.

FIGS. 13A1 to A6 shows embodiments 6 embodiments. Embodiment 12A1 is discussed further with regards to FIG. 11A. Embodiment 12A2 is discussed further with regards to FIG. 11E.

Embodiment 12A3 is similar to the embodiment shown in FIG. 6. Embodiment 12A4 is similar to the anchor shown in FIGS. 8 and 18. Embodiment 12A5 is further discussed with regards to FIG. 12. Embodiment 12A6 is further discussed with regards to FIG. 24B.

Figure 19:
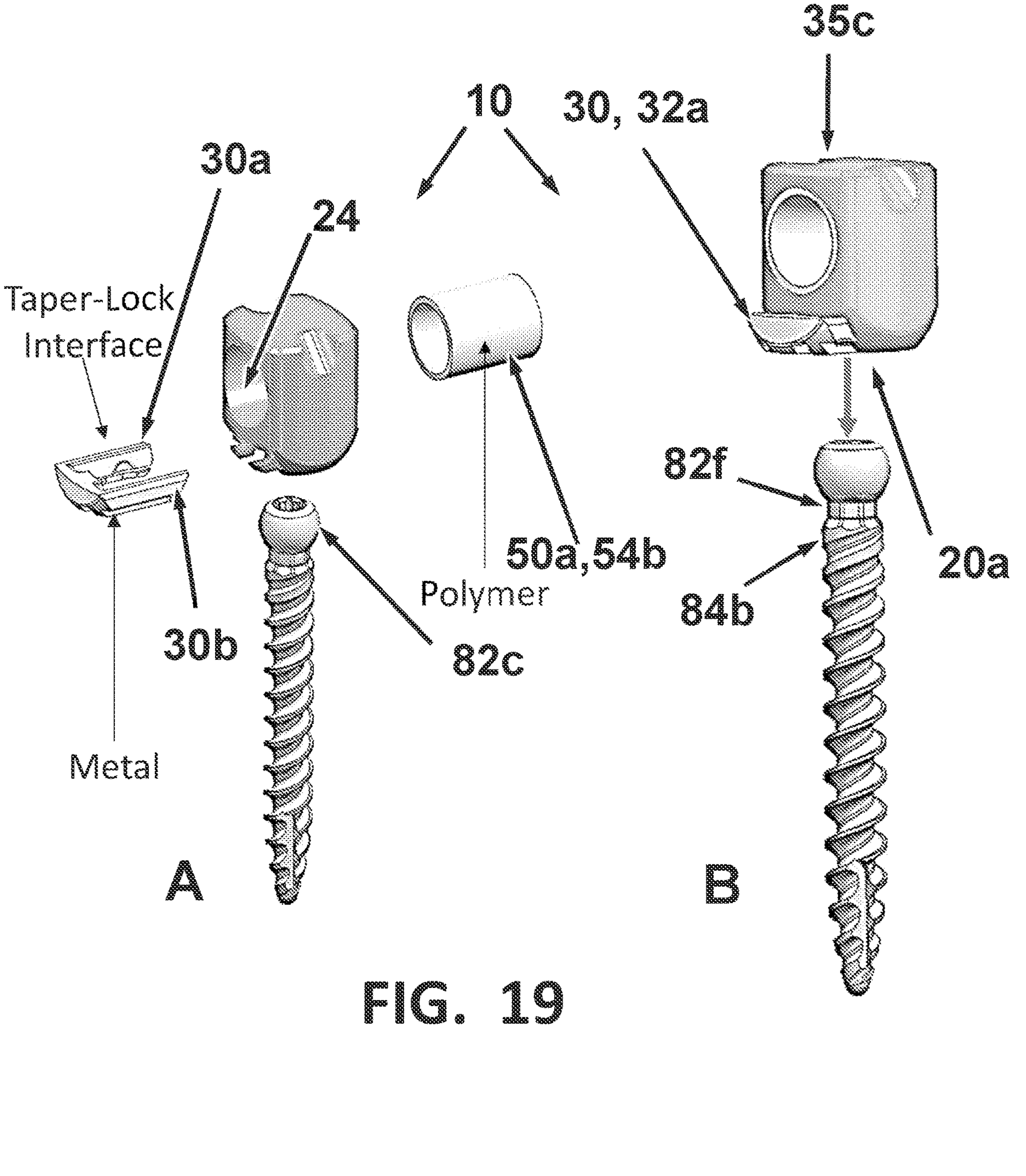
Figure 19:
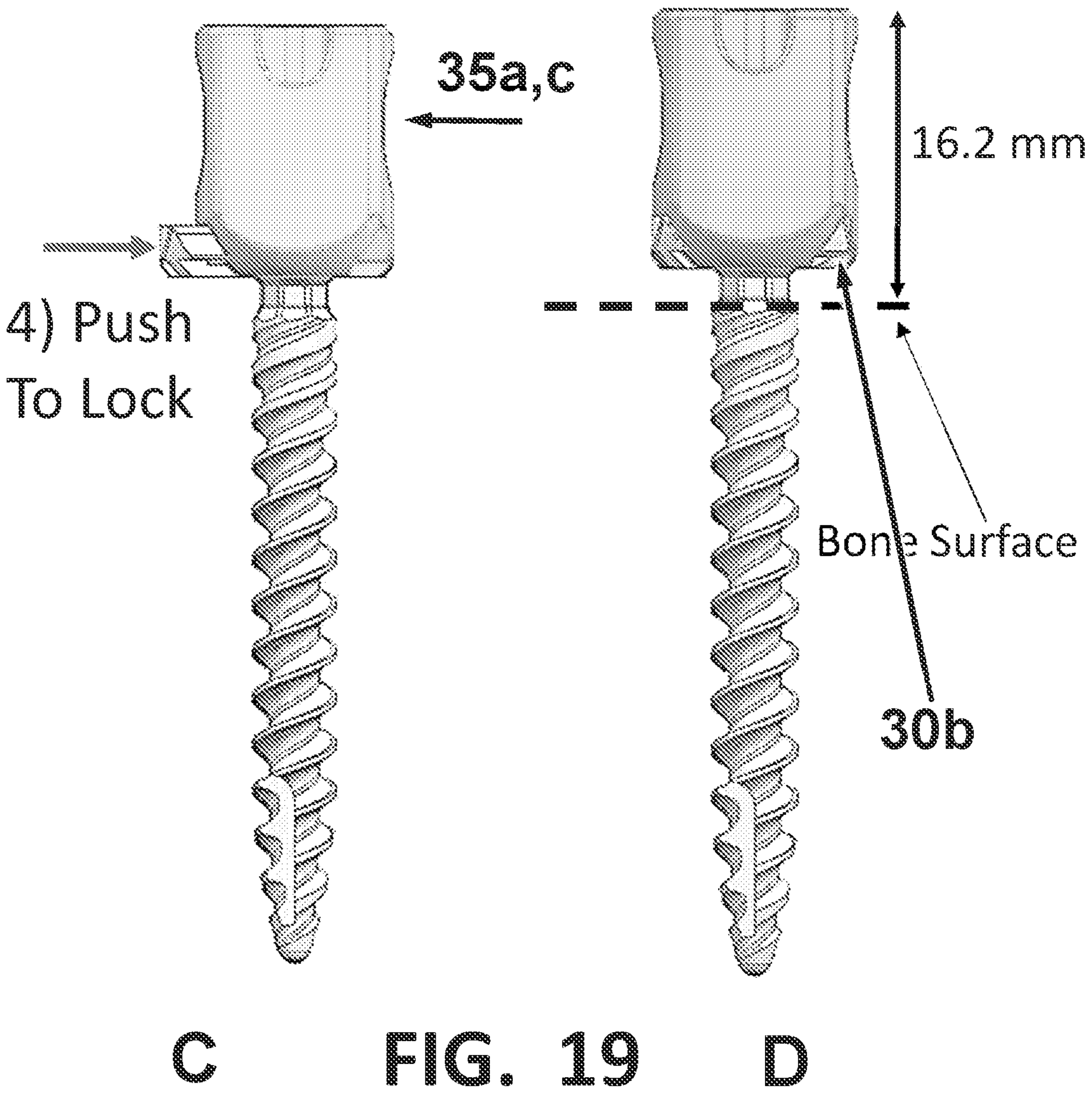

Embodiment of 13B1 is discussed further with regards to FIG. 19. Embodiment 13132 is discussed further with regards to FIG. 20. Embodiment 13C2 is discussed further with regards to FIG. 29. Embodiment 13C3 is discussed further with regards to FIG. 14.

Referring to FIG. 13C1, there is shown a portion of an anchor according to another embodiment of the present invention. Embodiment 13C1 includes a preferably rigid arm 70*g* that supports on one end a bushing 50 within a first ring 70*a*. As will be discussed in more detail later, the device of embodiment 13C1 permits the rod pathway 52*b* at a lateral distance spaced apart from the attachment of anchor 10 (not shown) to the spine. The cylindrical portion of rod 70*g* is coupled in any manner to a head 20. In that manner, the surgeon is presented with more options for the relative placements of the rod and anchors.

As shown in FIG. 13C1, the support arm includes a rigid portion extending outwardly from the ring 70*a*. This extension portion can be cylindrical (as shown), or of a faceted nature, grooved, or otherwise prepared so as to improve the security of the connection between arm 70 and the head of the anchor. In some embodiments, the cylindrical shape (as shown) is fixed to the head by friction originating from compression created by a set screw. As one example in contrast, a faceted version (as one example, with an octagonal shape) can be received between a pair of opposed arms having flat surfaces. In such embodiments, a set screw serves to maintain the arm within the head, but is not needed for purposes of preventing rotation of the arm relative to the head (such prevention being provided by the octagonal shape interfering with the internal surfaces of the opposing arms of the tulip head). Yet other embodiments of the support arm (such as those shown in embodiment 13C2 and FIG. 13D) are discussed with regards to FIGS. 29 and 14, respectively.

FIGS. 13D1, D2, and D3 show an "outrigger" configuration in which a laterally-displaced rod path 52*d* is supported on a head 20 by a bushing 74*c*. A first ring 70*a* offset by a relatively short support arm 70*g* serves as a bushing container 56 for a bushing 50 that will support a rod (not shown). The other end of the short support arm 70*g* includes a second ring 70*b* that contains within it a second bushing 74*c*. This second bushing 74*c* can be of any type, including low friction, harder organic materials (or coatings), as well as softer, more elastomeric organic materials (such as biocompatible rubbers).

Figure 3:
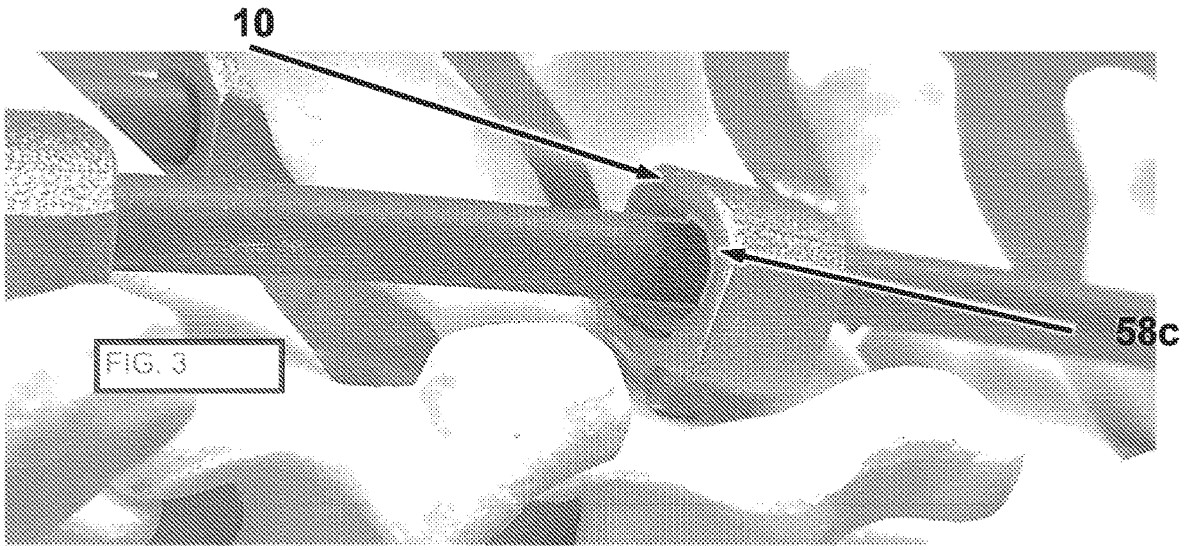
FIG. 3 is a close-up of a portion of the apparatus of FIG. 1A
Figure 4:
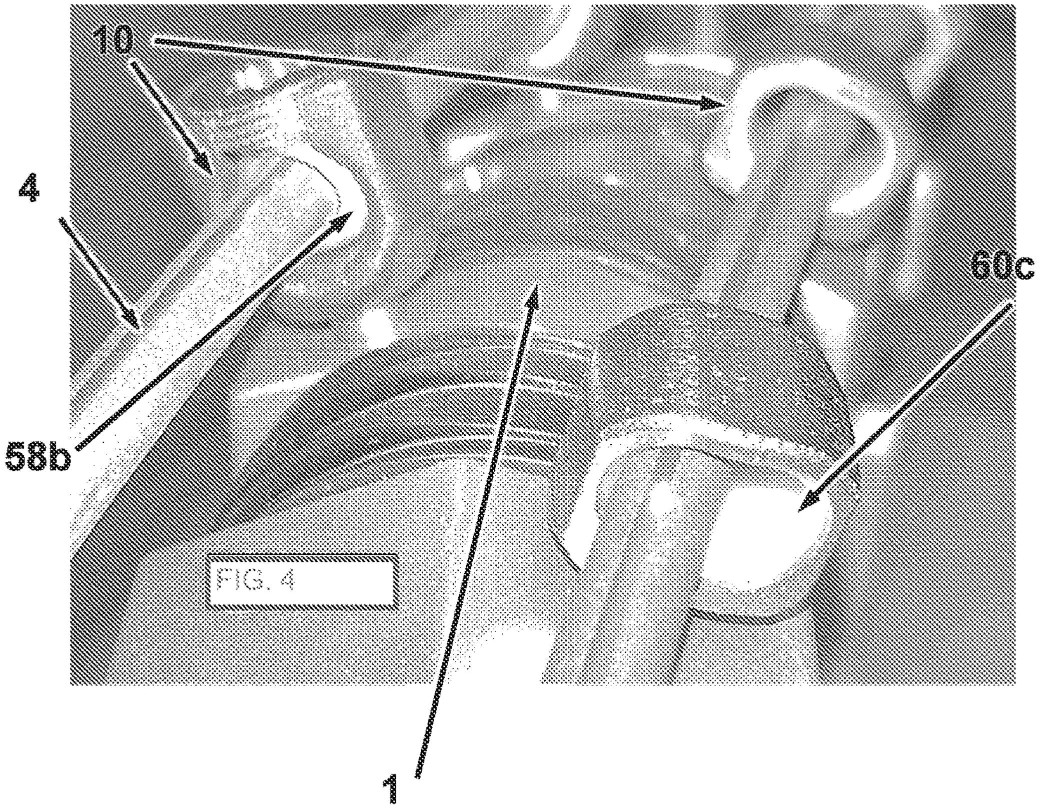
FIG. 4 is a close-up top, perspective view of a spine model with two rods attached to the model according to another embodiment of the present invention.

Referring to FIG. 13D3, it can be seen that the second ring 70*b* defines an axis (for attachment to head 20*b*) that is nonparallel with the rod axis established by bushing 50 as rod pathway 52*b*. As shown, the rod axis and head axis are perpendicular in one embodiment, although other embodiments can be of any relative angular orientation. Also shown in FIG. 13D3 is an anchor head 20*b* that is modified to accept around it the second bushing 74*c*. In one embodiment, the head is fixedly attached to a support device 80, although any manner of support is contemplated.

Referring to FIG. 13D1, it can be seen that the insertion of head 20*b* within bushing 74*c* establishes an annular (or circumferential) cavity 24*d* in cooperation with the interior of second ring 70*b*. Second bushing 74*c* is preassembled into ring 70*b*, such that the coupling of arm 70 onto head 20*b* simultaneously establishes the annular cavity 24*d* and also fills the annular cavity with bushing 74*c*.

Preferably, the proximal end of head 20*b* is internally threaded so as to receive therein a set screw 42*a*. In some embodiments, set screw 42*a* includes a head that is wide enough to extend over the top annular face of bushing 74*c*. A tightening of set screw 42*a* within head 20*b* places second bushing 74*c* in compression between the underside of the head and an internal surface of head 20*b*. In some embodiments, this head does not have sufficient extent to compress against the upper annular surface of ring 70*b*, such that the support of arm 70*g* relative to head 20*b* is accomplished only through bushing 74*c*. This isolation of the arm 70*g* from head 20*b* can also be accomplished with the proper dimensioning of the set screw, head, and ring.

Figure 14:
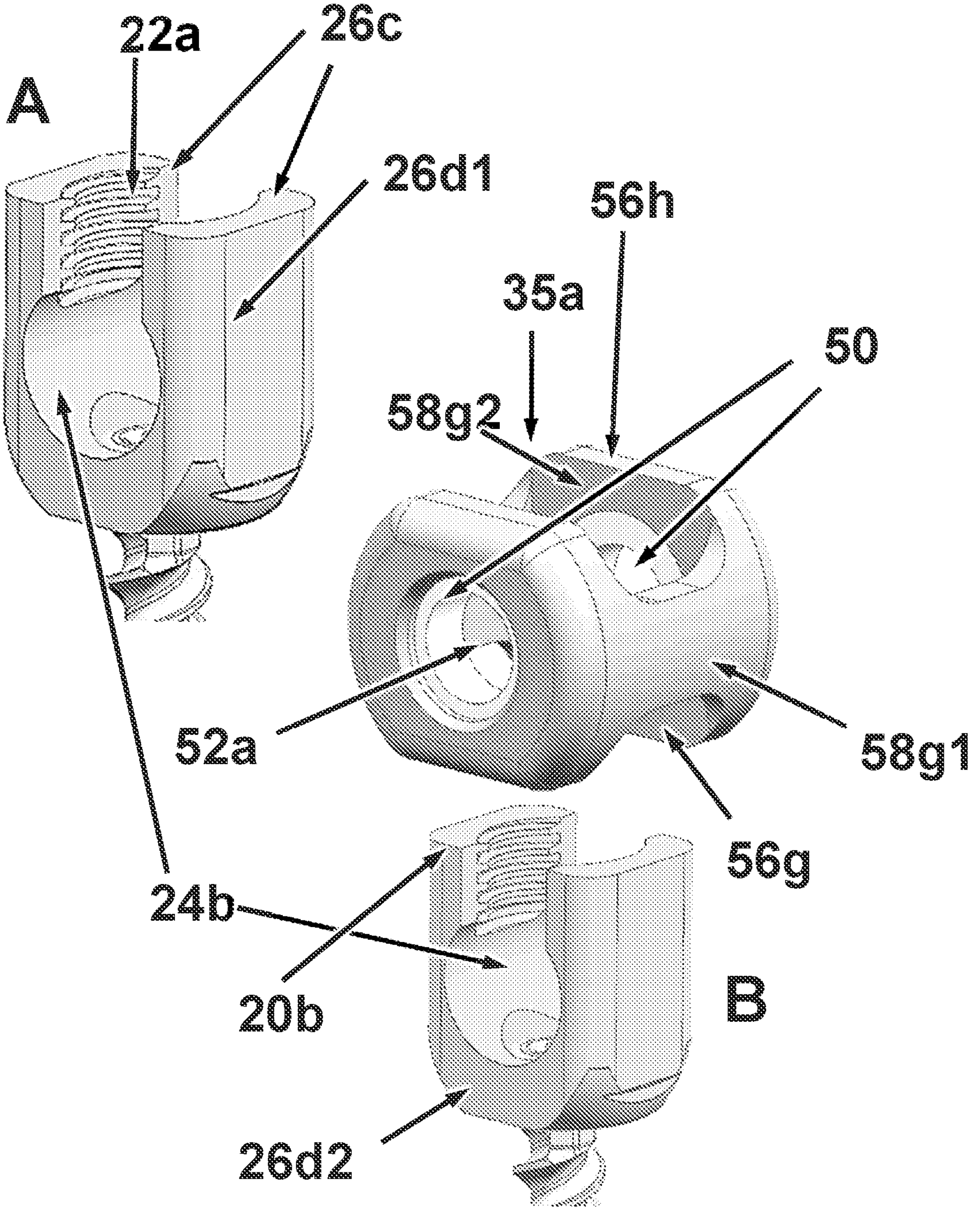
FIG. 14 show various views of the anchor of FIG. 13C3.
Figure 14:
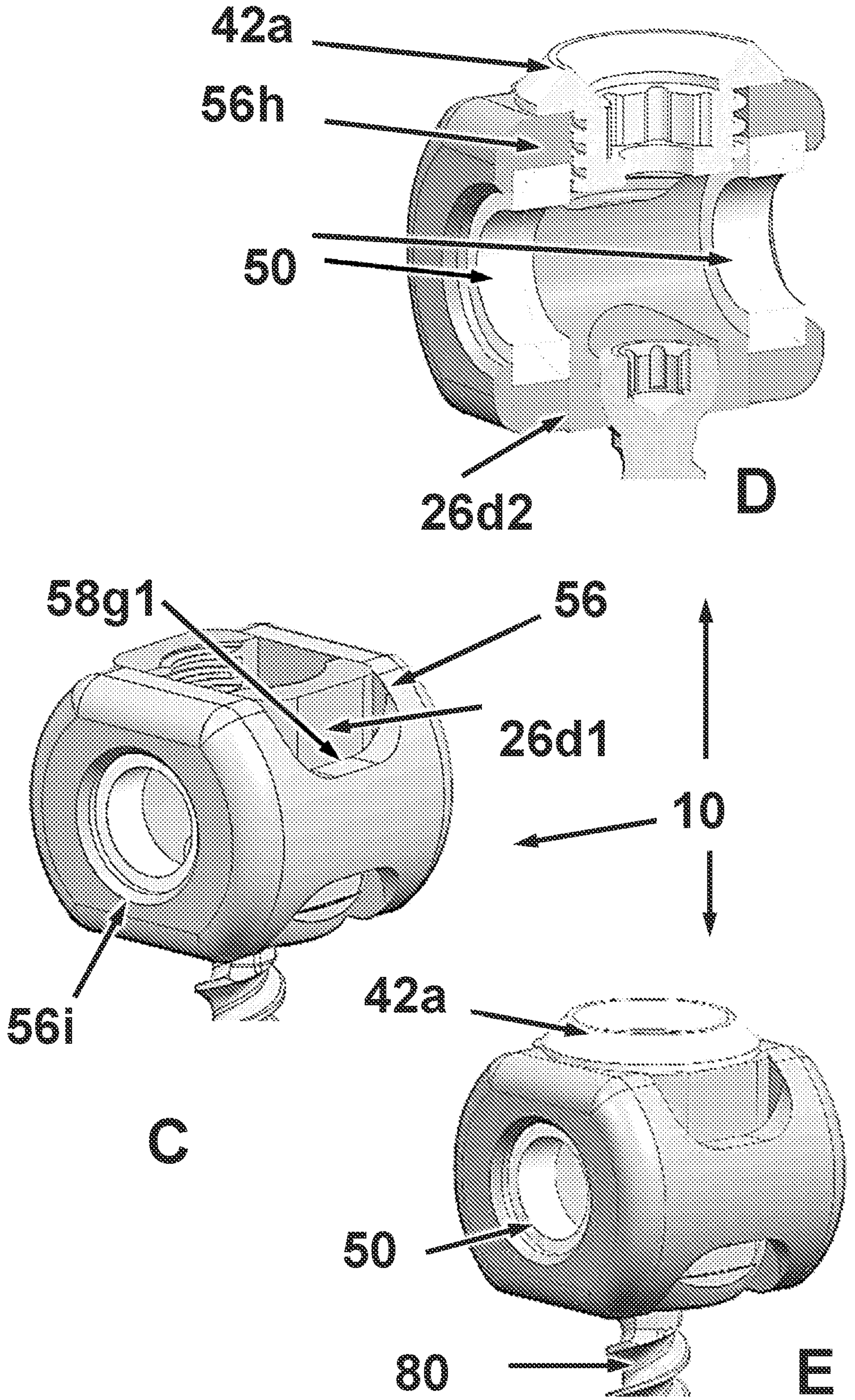

FIG. 14 shows exploded and cutaway views of a guiding anchor 10 that includes a bushing container 56 that includes a pair of bushings on either side of channel 52*a*. It can be seen that after the bushing container assembly is placed on the rod, that the assembly and rod can be placed downward onto a device 80.

FIG. 14A shows the head 20 and supporting device 80 of an anchor 10. Preferably, head 20 includes a pair of opposing arms (a tulip) that define between them an internal cavity 24*b*. Head 20 preferably includes an external bushing container interface 26*d*1 that in the embodiment shown includes a flat external surface on the outside of each arm 26*c*. Referring briefly to FIG. 14C, it can be seen that this external flat surface 26*d*1 of head 20 comes into sliding contact with a corresponding internal flat face 58*g*1 of bushing container 56. These lateral flats 26*d*1 are best seen in sliding and abutting contact with bushing container internal head interfaces 58*g*1 in FIG. 14C. Head 20 further includes an internal bushing container interface surface 26*d*2 located around the cavity opening 24*b*. These external bushing container interfaces 26*d*2 generally surround the rod pathway 52*a*, and after assembly will be located opposite of corresponding internal head interface surfaces 58*g* of bushing container 50 (as best seen in FIGS. 14B and 14D). Preferably, the upper, inner portions of arms 26*d* include a threaded portion 22*a* for threaded mating with the external threads of a set screw 42*a* (as seen in FIG. 14D).

In one embodiment, bushing container 50 preferably includes a pair of bushings 50, with each one located in an outrigger aperture 56*i*. Referring to FIG. 14B, it can be seen that the assembled head 50 includes a pair of bushings 50 each located in a corresponding aperture 56*i*, in alignment with rod pathway 42*a*, and on either sides of a central open volume that is adapted and configured to surround a portion of head 20.

FIGS. 14D and 14E show a portion of the assembled anchor 10. A sets crew 42*a* is threadably coupled to arms 26*c*, the set screw including a circumferential lip that seats against the top surface of bushing container 56. A rod (not shown) is supported internally in pathway 52*a* by the bushings 50 located on either side of the head 20. Preferably, the internal cavity 24 is adapted and configured to provide clearance around the supported rod, such that there is little or no contact between head 20 and the rod.

Figure 15A:
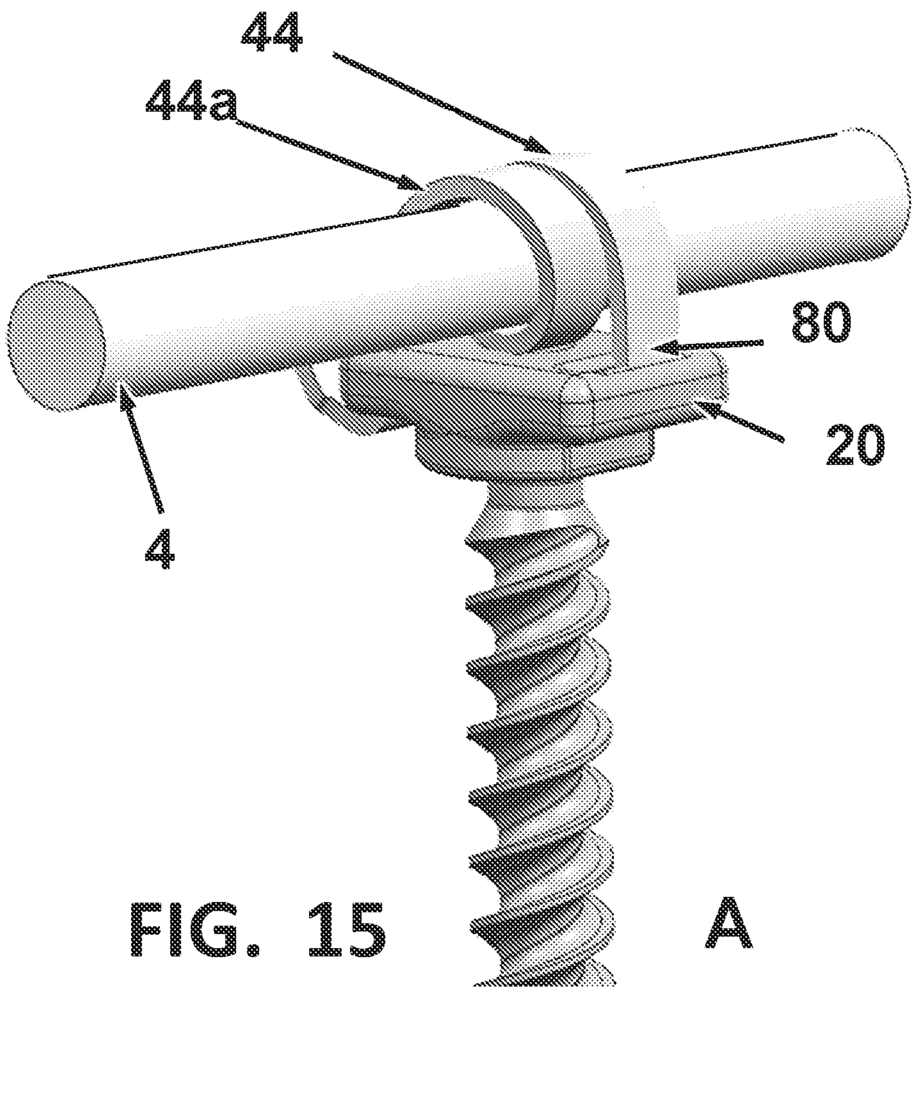
Figure 15:
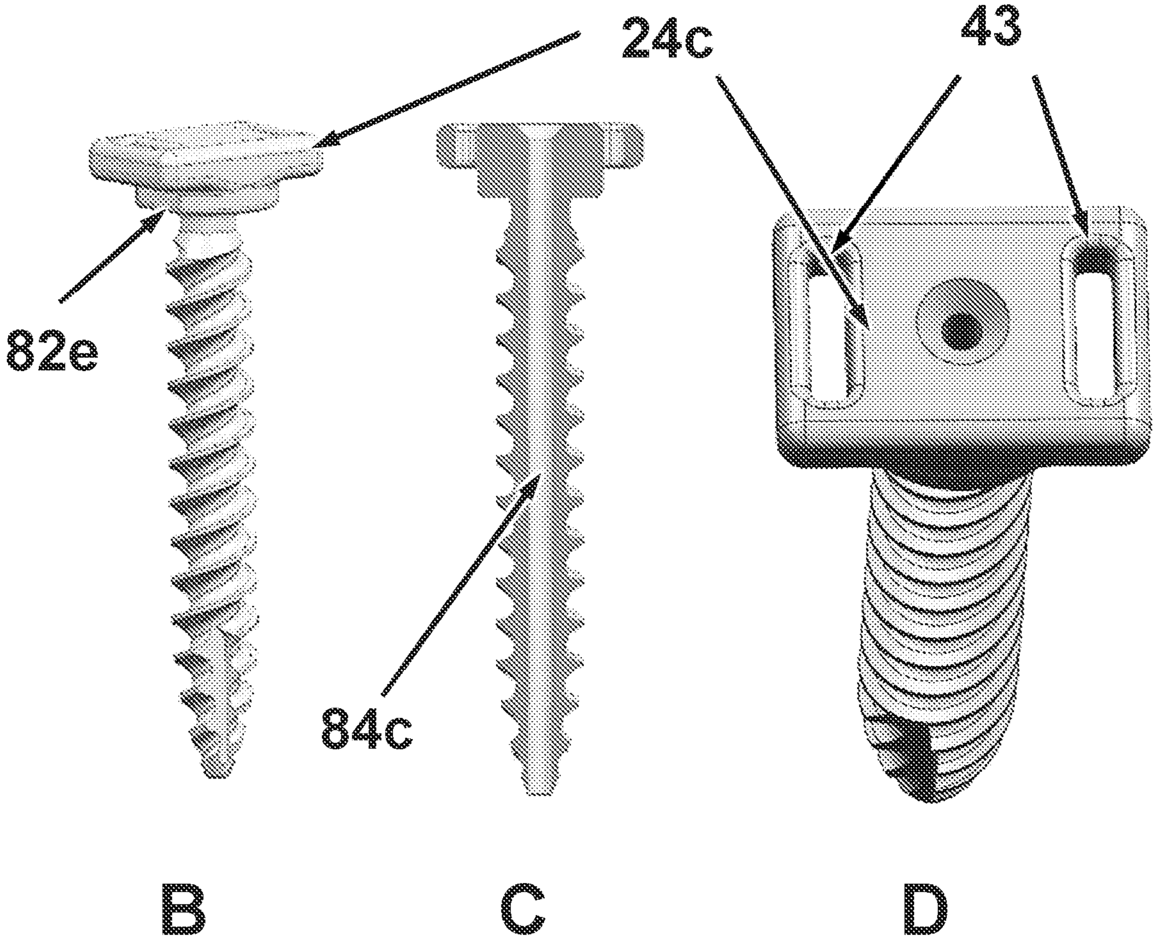

FIG. 15 shows a guiding anchor 10 in which the rod is coupled to a device 80 by way of a flexible connector 44 that is looped 44*a* around the rod. The ends of the flexible connector are attached to slots 43 of head 20.

The anchor 10 of FIG. 15 includes a flexible connector 44 that is looped 44*a* around the rod. Flexible connector 44 is attached at each end to the top surface of a platform 24*c*, with the ends of the flexible connector being attached to platform 24*c* by one or more grooves 43. Preferably, platform 24*c* is coupled to a cannulated support device 80 by way of a fixed junction 82*e*.

The anchor of FIG. 15 is adapted and configured to generally retain a rod 4 (of any shape) in a general location, yet at the same time provide limited six degree of freedom movement. Referring to FIG. 15A, it can be seen that rod 4 is unrestrained from movement along its axis. The lateral (side to side) movement of rod 4 relative to anchor 10 is generally constrained by the tightness and the flexibility of loop 44. The vertical (distal) motion of the rod is constrained by abutment against platform 24*c*. The vertical (proximal) motion of the rod is limited by the flexibility and wrapping of connector 44. The relative pivotal motions of rod 4 relative to head 20 are limited by the wrapping and flexibility of connector 44 (for yawing motion), and by wrapping and flexibility of the connector along with the abutment against the top platform surface of head 20 (for pitching motion). Note that rolling motion (i.e., rotation about the axis) is generally unconstrained by connector 44, although in some embodiments a rolling motion in one direction may tighten the interface of the connector 44 with the external surface of rod 4, and rolling motion in the opposite direction may slightly loosen the connection.

Figure 16:
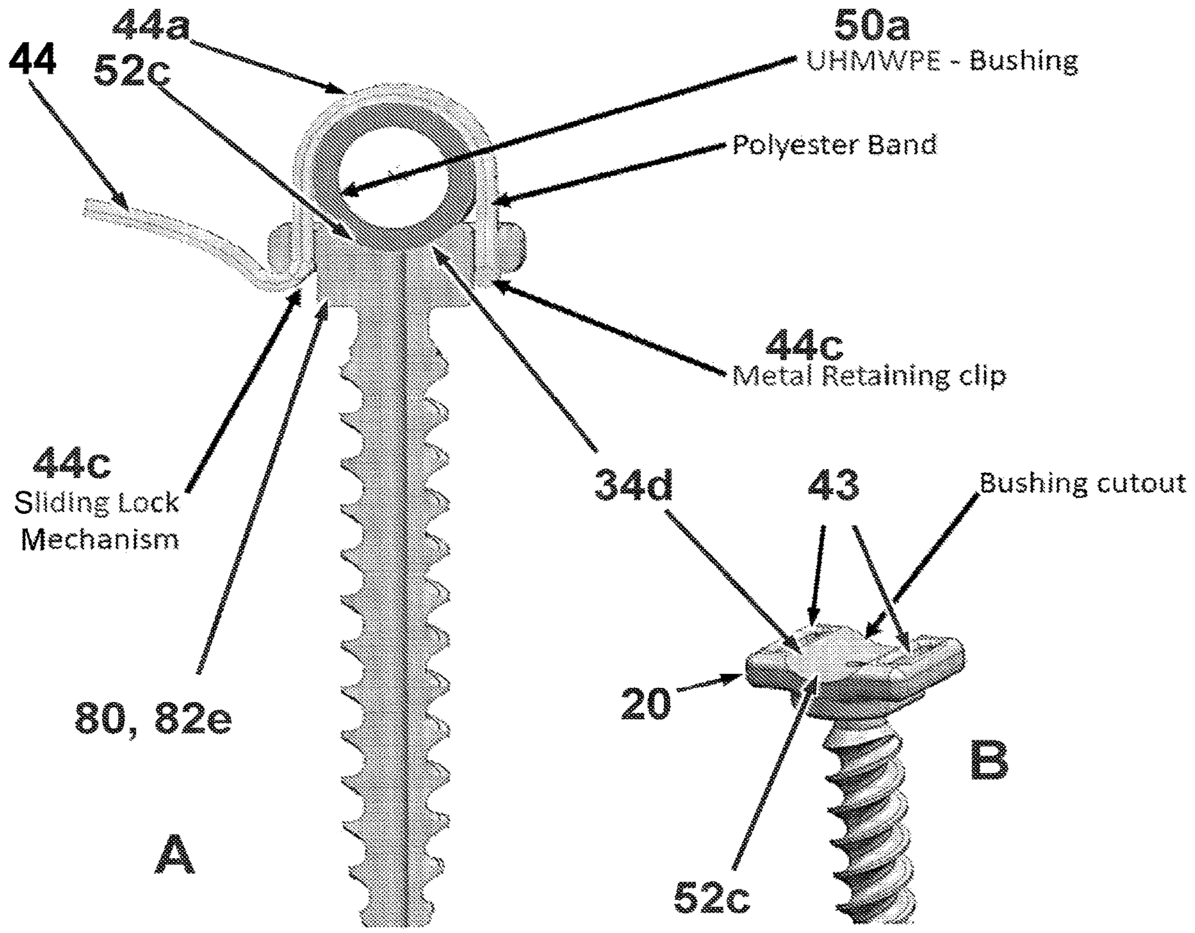

FIG. 16 shows a guiding anchor 10 similar to that of FIG. 15, except head 20 includes a groove 34*d* that receives a separable organic, polymer bushing 50*a*. A loop 44*a* of flexible connector is attached by way of slots 43 to the head 20.

The anchor 10 of FIG. 16 includes a groove 34*d* that has a shape complementary to the external shape of the bushing, and as shown as a semi-cylindrical shape that is complementary to the cylindrical shape of bushing 50*a*. The bushing is held in place in groove 34*d* by a flexible connector 44*a* that wraps around the outside of the bushing, with one end of the connector being retained in a groove 43 by a retaining clip 44*c*. As shown, the connector is wrapped around the outside of the bushing and looped through a slot 43 on the opposite side of head 20. Note that the preferably close-fitting nature of the loop 44*a* restrains many of the degrees of freedom found in the anchor of FIG. 15. For example, any yawing or pivoting motion is restrained by placement of the bushing within groove 34*d*, as well as the flexibility of connector 44*a*. Likewise, any translational movement of the rod is limited by the preferably tight fit of connector 44.

Figure 17:
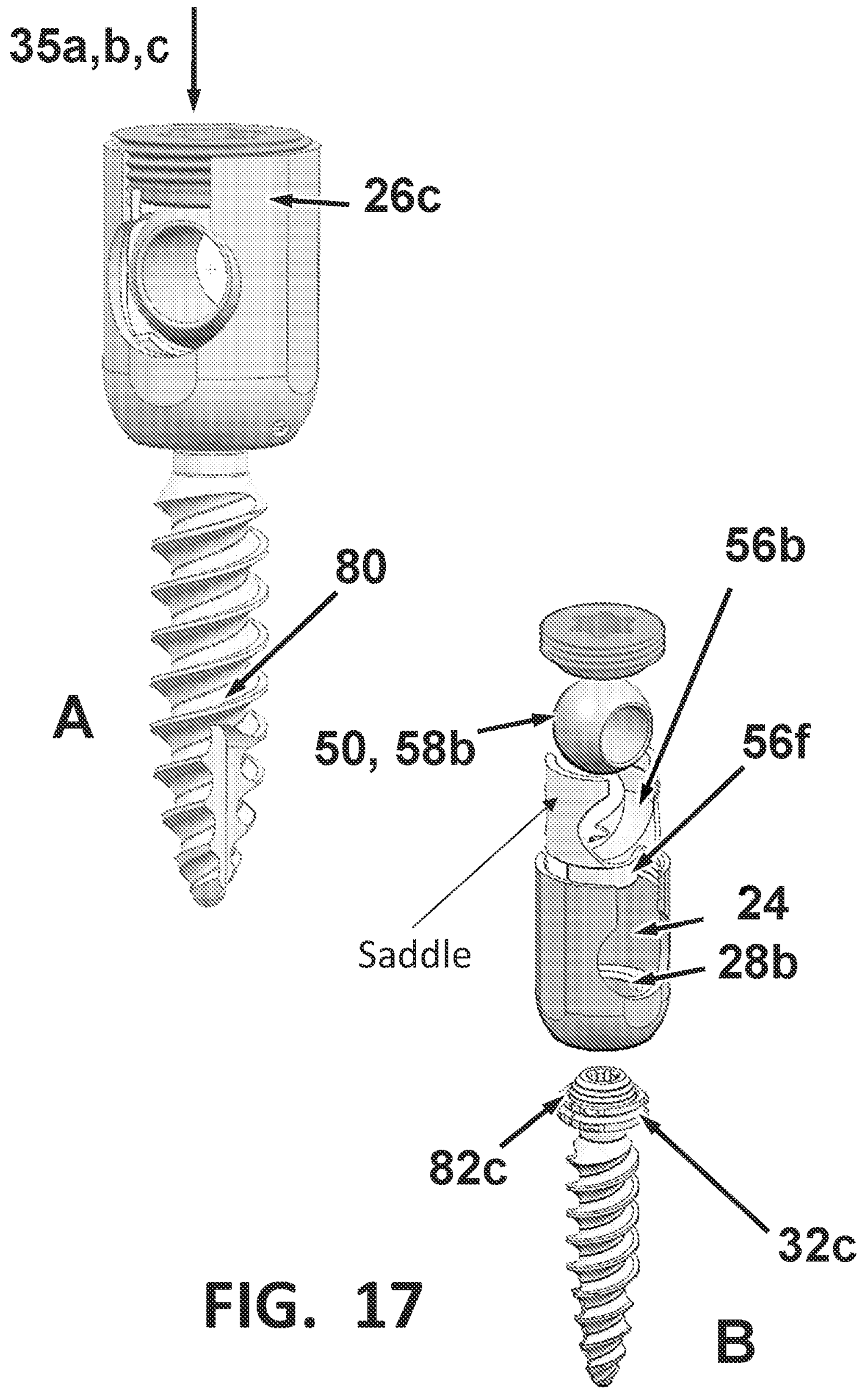
Figure 17:
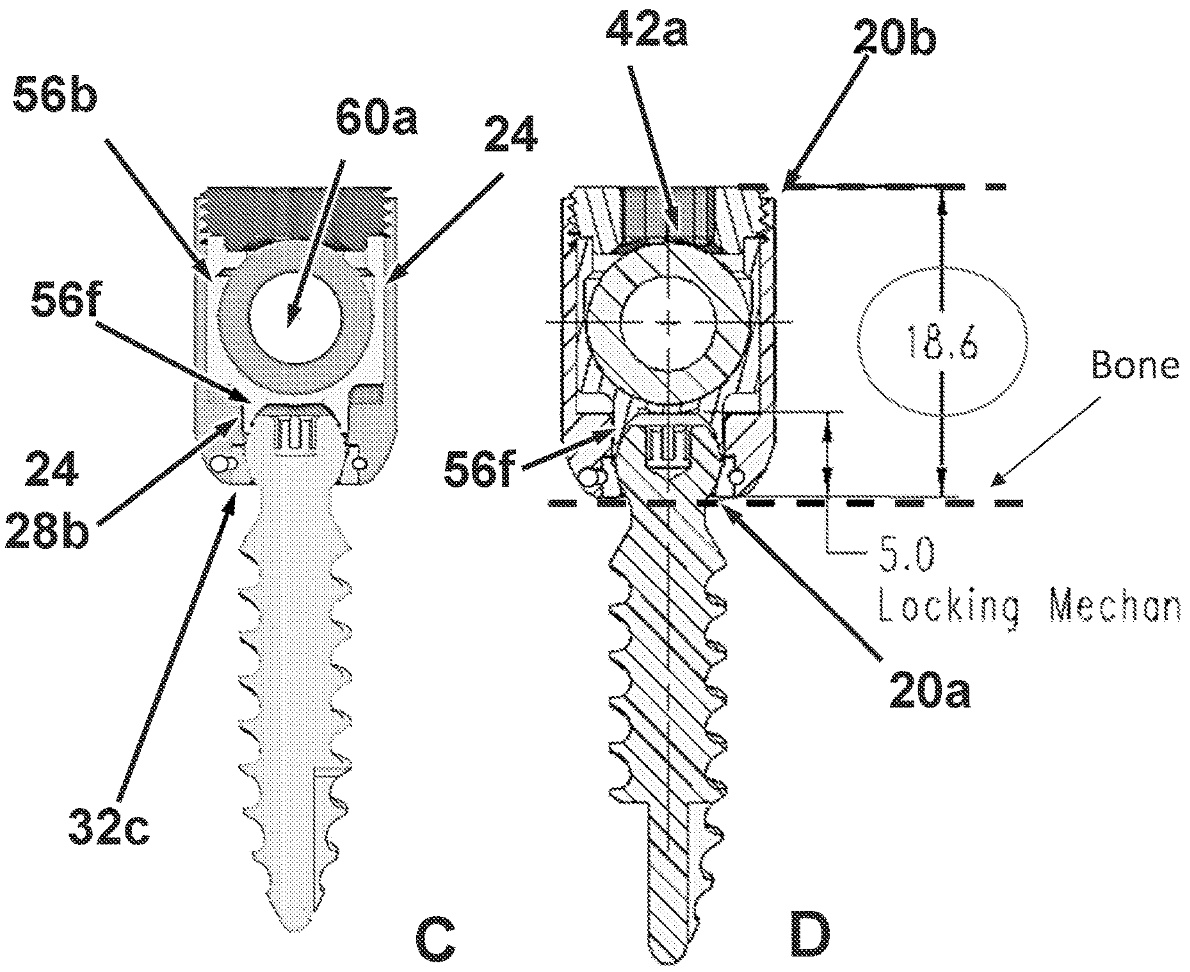

FIG. 17 shows assembled, exploded, and cutaway views of a guiding anchor 10. Anchor 10 includes a bushing container 56*b* arranged as a saddle which receives within it a bushing having spherical outer surface 58*b*. The opened, support arms 56*b* are received within a corresponding pair of arms 26*c* of head 20.

Referring to FIGS. 17B, 17C, and 17D, it can be seen that the saddle or bushing container 56*b* includes on its distal end an interface 56*f* with the head of supporting device 80. In one embodiment, the interface 56*f* includes a pair of short arms that extend downwardly and over a generally spherical device junction 82*c* and extending into the space between the spherical head and the pocket 28*c* of head 20.

Referring to FIG. 17C, it can be seen that the bushing container 56*d* is received within the cavity 24 of head 20. The bottom interface 56*f* is preferably in contact with the spherical head 82*c* of device 80. The pair of arms 56*b* extend out of cavity 24, and when set screw 42*a* is tightened, the top surfaces of arms 56*b* are in compressive contact with the underside of the set screw. Therefore, compressive loading from the set screw is transferred through container 56*b* through interface 56 and onto the interface between pocket 28*b* and junction 82*c*. This compressive force against this interface of the device 80 and head 20 results in a frictional locking of device 80 relative to head 20. It can also be seen in FIGS. 17C and 17D that the spherical junction 82*c* is constrained to remain within a distally located pocket of head 20 by a retention member 32*c* that is adapted and configured to restrain a locked spherical device junction.

Figure 18:
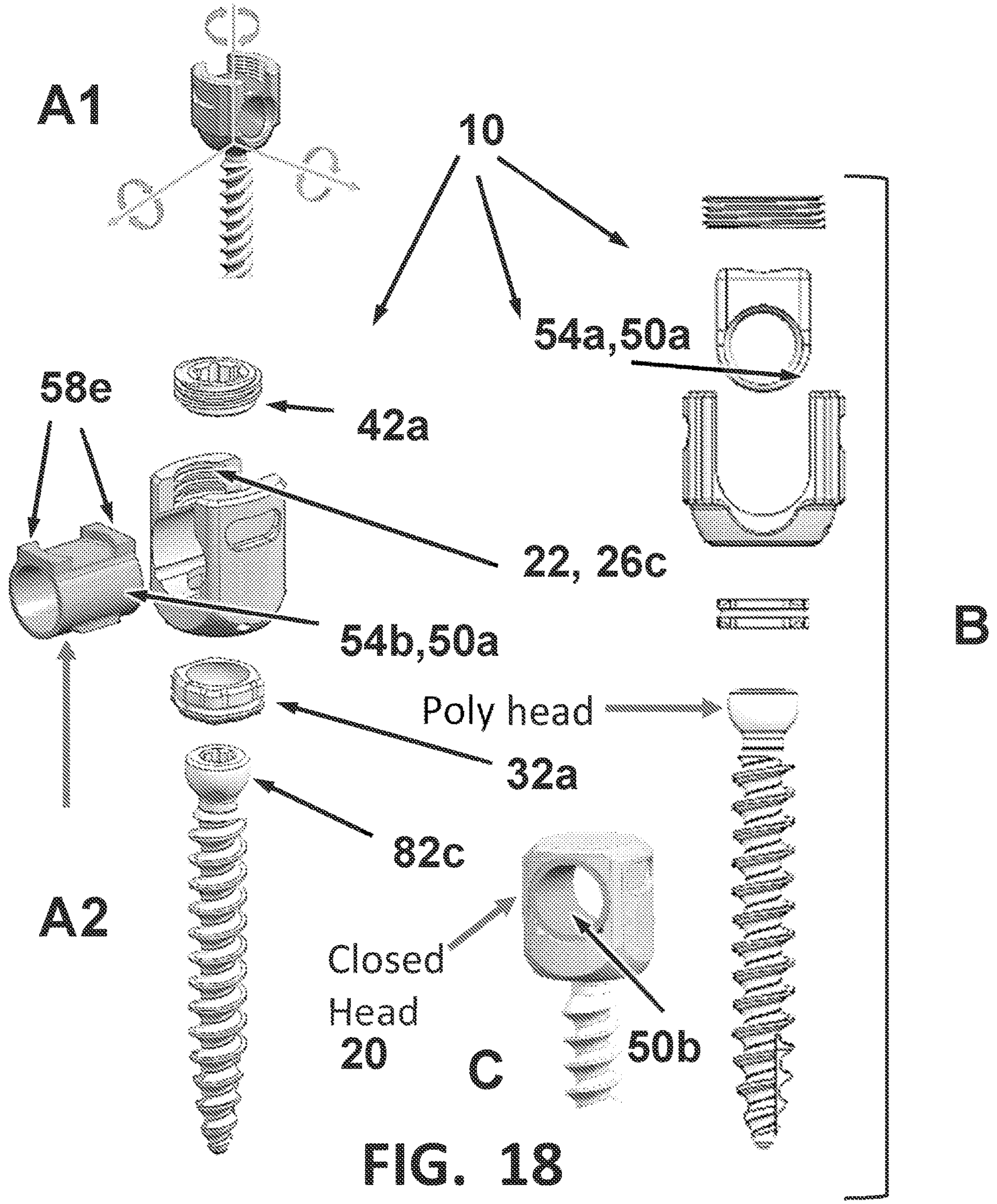
Figure 18:
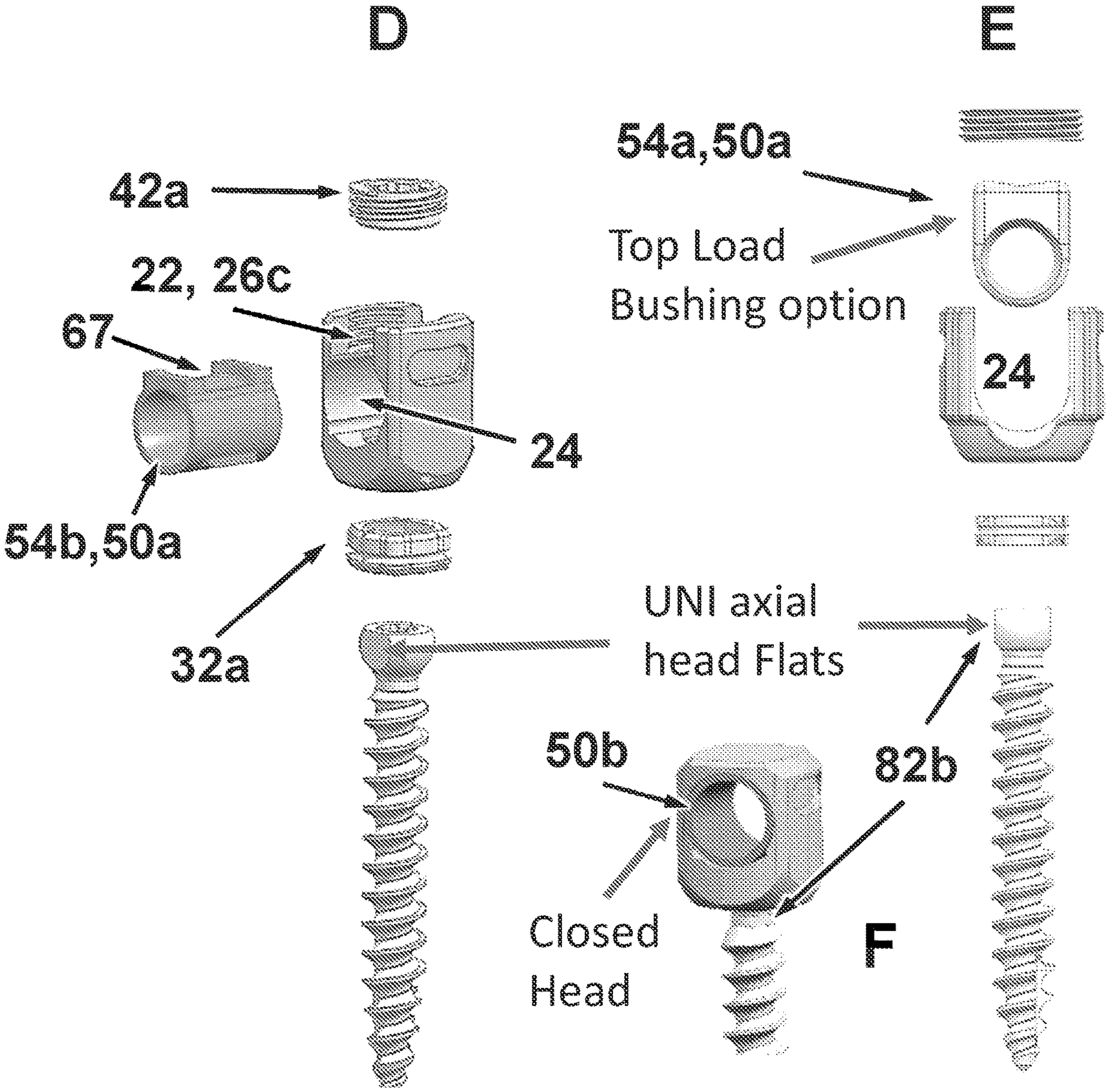

FIG. 18 depicts guiding anchors 10 showing embodiments having both spherical (polyaxial) device junctions 82*c* and circular (uniaxial) device junctions 82*b*. As one example, each of these heads 20 include side loaded separable bushings 50*a*, each having one or more retention ledges 58*e* that assist in securing the bushings within the heads, and further including a central interface 67 for a set screw. Also shown are closed heads that include molded bushings 50*b*.

FIG. 18 illustrates the versatility of the various embodiments shown herein. The anchors of FIGS. 18A1 and A2, 18B, and 18C each show various different heads 20 that are attached to corresponding devices 80 so as to be polyaxially pivotal. Each of the support devices 80 incorporate a device junction 82*c* that includes a preferably spherical surface. The various device junctions are retained within the corresponding heads 20 by a retention member 32*a* that forms an interface between an underside pocket of head 20 and the junction 82*c*, so as to permit polyaxial movement (i.e., pivotal in two orthogonal directions), while at the same time constraining the device to remain attached to the head.

Figure 2:
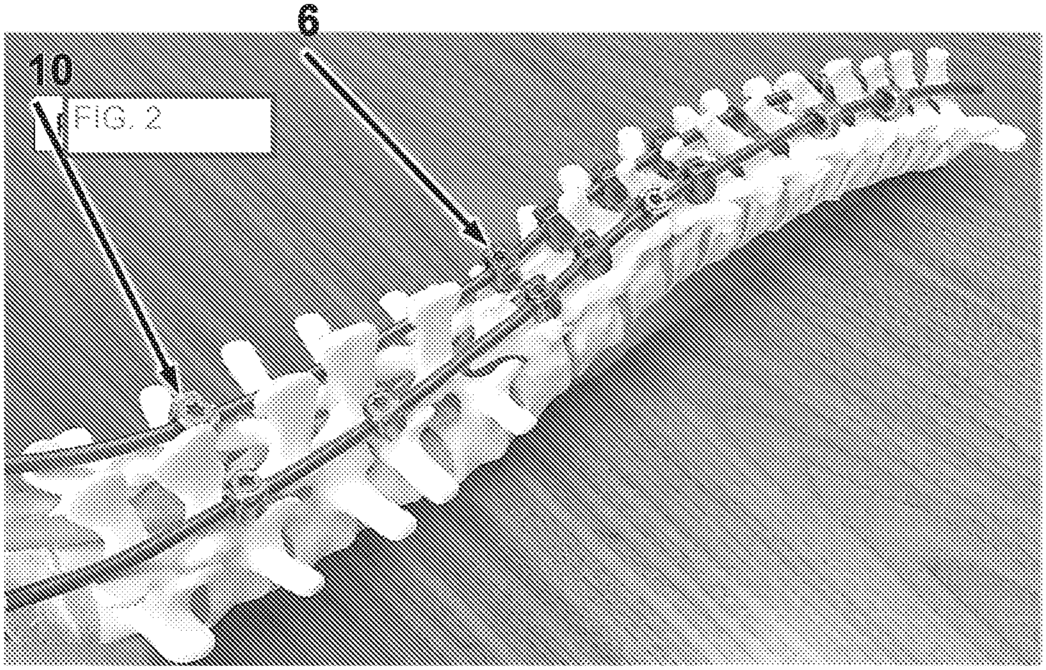
FIG. 2 is a top, perspective view of the apparatus of FIG. 1B from the other side.

In contrast, the anchors of FIGS. 18D, 18E, and 18F are adapted and configured to limit pivotal motion to a single axis. The various devices 80 are retained within the corresponding heads 20 by a retention member 32*a*. However, the outer surfaces of device junctions 82*b* are preferably flattened on opposing sides, with the other opposing sides being rounded and preferably cylindrical. Therefore, the pivotal motion of the anchors of FIGS. 18D, 18E, and 18F are limited to a pivotal motion about a single axis. In some embodiments, the flattened sides of head 82*b* are received within an internal slot of head 20 that is likewise flattened on opposing sides. Since these flattened surfaces of the head and device junction are adjacent to one another, pivotal motion about the axis of device 80 is constrained. In contrast, and as shown in FIG. 18A2, the heads 20 shown in those three figures are preferably rotatable in each of three orthogonal directions.

The various anchors shown in FIG. 18 also help illustrate a sample of bushings contemplated for various anchors. FIGS. 18A2 and 18D each show bushings that are loaded from the side, and preferably along the axis of the rod pathway, although side loading in a direction perpendicular to the cavity is also contemplated. These bushings are preferably restrained by set screws.

FIGS. 18B and 18E show heads in which the bushings are loaded from the top and received within the corresponding cavity 24 of the head 20. Bushings are preferably retained by set screws, although they can be retained in any manner.

The anchors shown in FIGS. 18C and 18F show closed heads 20 in which the bushing 50*b* is preferably molded into place. Although the six anchors of FIG. 18 depict various types of bushings, it is understood that these anchors are shown by way of example only. It will be understood from a review of other embodiments that many different anchors shown herein can be provided with polyaxial support devices or uniaxial support devices. Further, although not shown in FIGS. 18, these various anchors can also include provisions for being locked into a user-selected pivotal angle.

FIG. 19 shows exploded and assembled versions of a guiding anchor 10 in which a head 20 can be vertically placed on a device 80, with a sliding member 30 being used to interlock the head and the device. After sliding member 30 is pushed toward device junction 82*c*, one or more one-way spring latches 30*b* prevent backing out of sliding member 30. Additional views of the sliding locking member 30 and head 20 are provided on FIG. 32.

Figure 32:
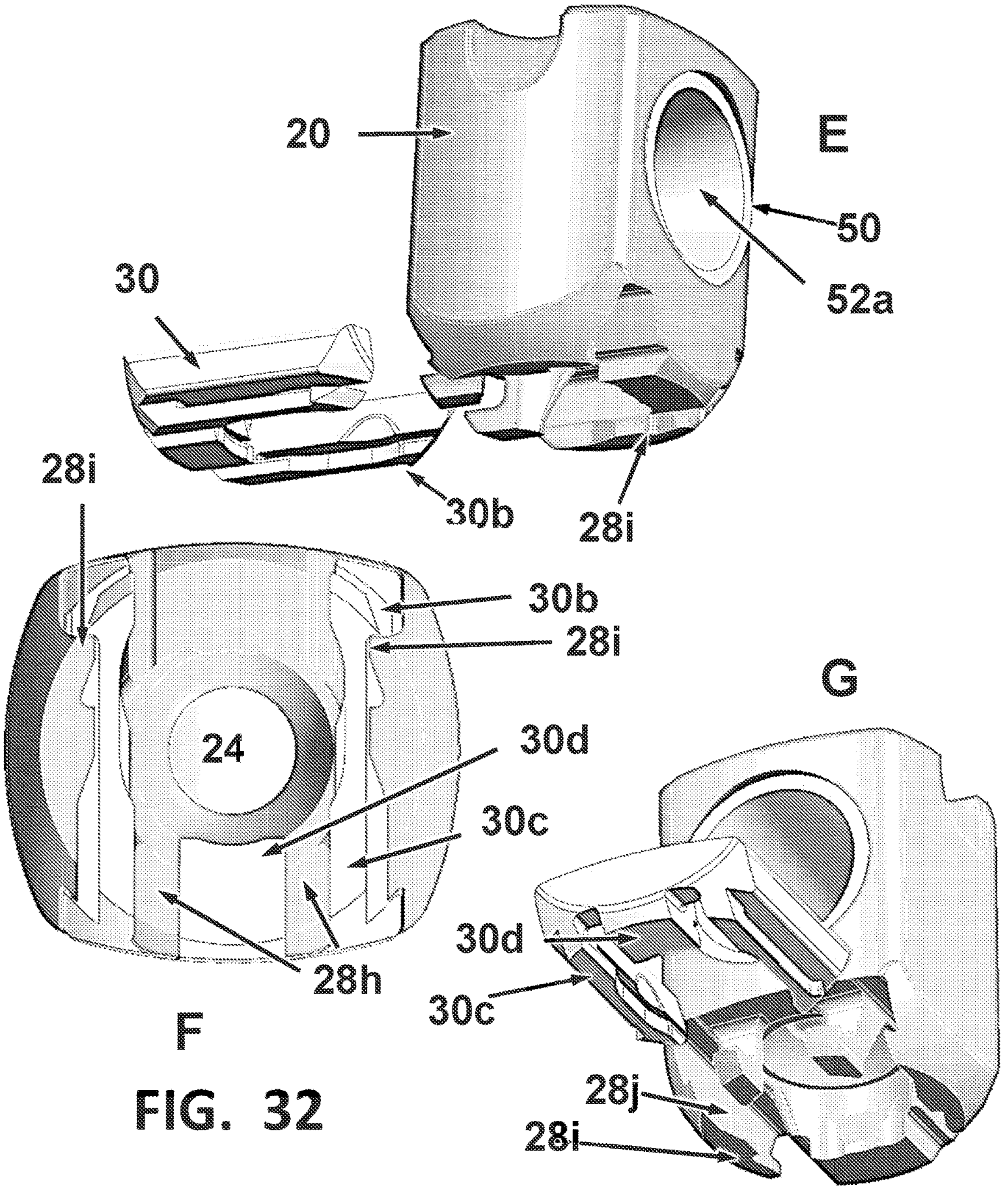
FIGS. 32E-32G represent additional views of the apparatus of FIGS. 19A-19D.

Anchor 10 of FIGS. 19 and 32 preferably includes a head 20 that receives within it a side-mounted polymer bushing 50*a*. However, yet other embodiments are not so limited and can include bushings that are molded in place or spray-coated in place, bushings inserted from above, and still further bushing/head configurations shown herein.

Head 20 is preferably attached to the spine by a support device 80 having a device junction 82 that includes a region 82*f* having a smaller width than the head 82*c* above it, or the threaded area 84*b* below it. Although the device junction in FIGS. 19A and 19B is shown as a spherical junction 82*c*, it is understood that any type of junction geometry can be used, such that the geometry is wider above the necked-down region 82*f*. As shown, 82*f* has a smaller outer diameter than the diameter of junction 82*c*, or the immediately adjacent diameter threaded area 84*b*.

Referring to FIG. 32F, this supporting device 80 extends through the bottom aperture that extends into cavity 24. When the sliding member 30 is full inserted (as shown in FIG. 32F), the latch 30*d* is located within the necked-down region 82*f*. Latch 80*d* extends toward the reduced width section 82*f*, such that fully inserted latch 30*d* interferes with any attempt to remove head 20 from support device 80.

Referring to FIGS. 32E, F, and G, it can be seen that sliding member 30 has a pair of cantilever 30*c* that are slidingly received on opposite sides of head guiding features 28*h*. Preferably, latch 30*d* is slidingly received between guiding features 28*h*. As the sliding member 30 is inserted into head 20, each of the ends of the cantilever arm are received within a corresponding slot 28*j*, the arms being guided by the slots toward notches 28*i* at the end of slots. Referring to FIG. 32*f*, it can be seen that as the arms 30*c* move within the slots 28*j* that the angled ends of the arms 30*c* pass over notches 28*i* and are elastically pushed inward by notches 28*i*. Once the ends of the cantilever arms are passed the notches, the arms spring back into place, such that they come into a locking arrangement with the notches as best seen in FIG. 32F. This locking arrangement permits removal of slide 30, and locks device 80 onto head 20.

Figure 20:
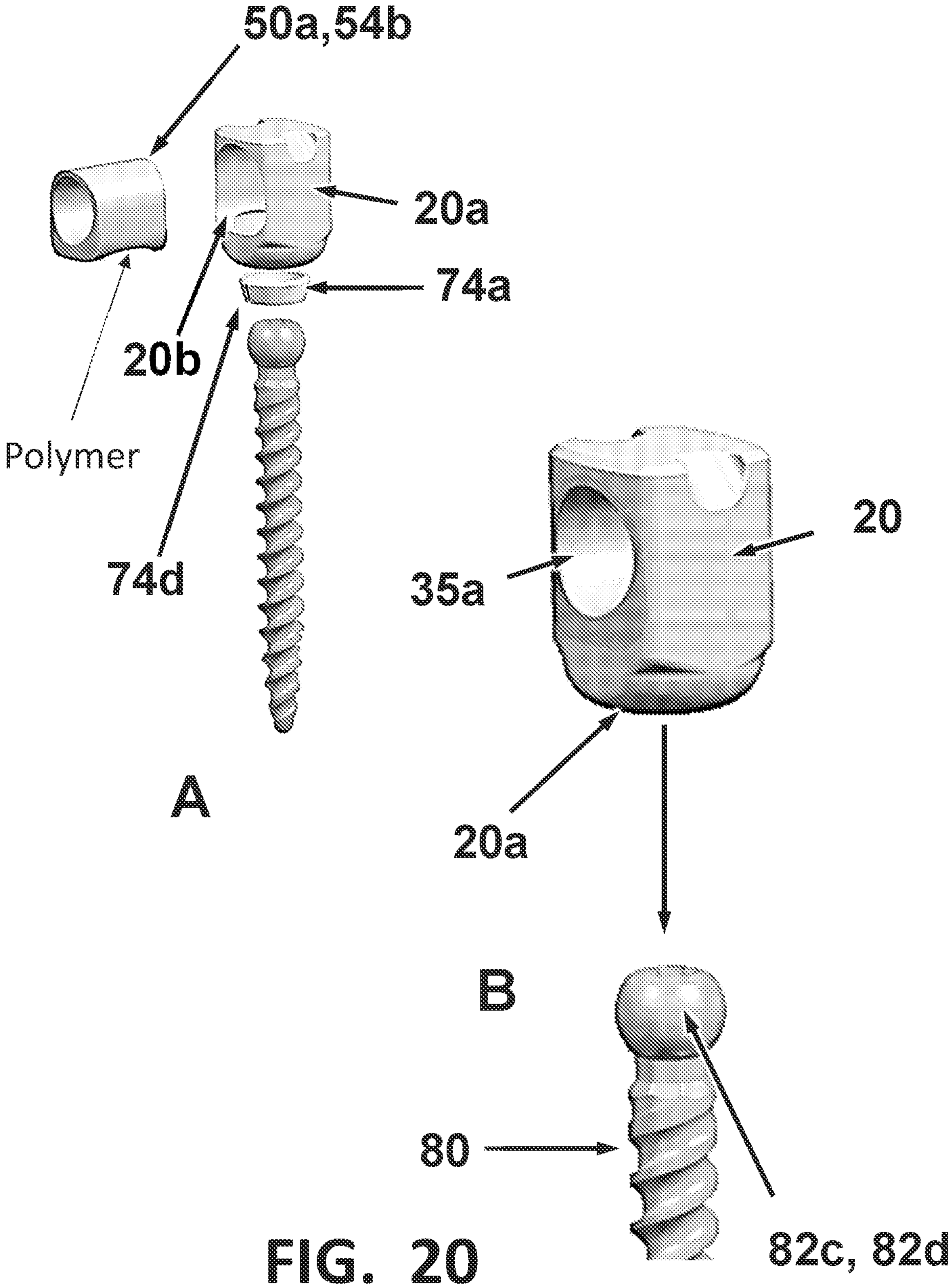
Figure 20:
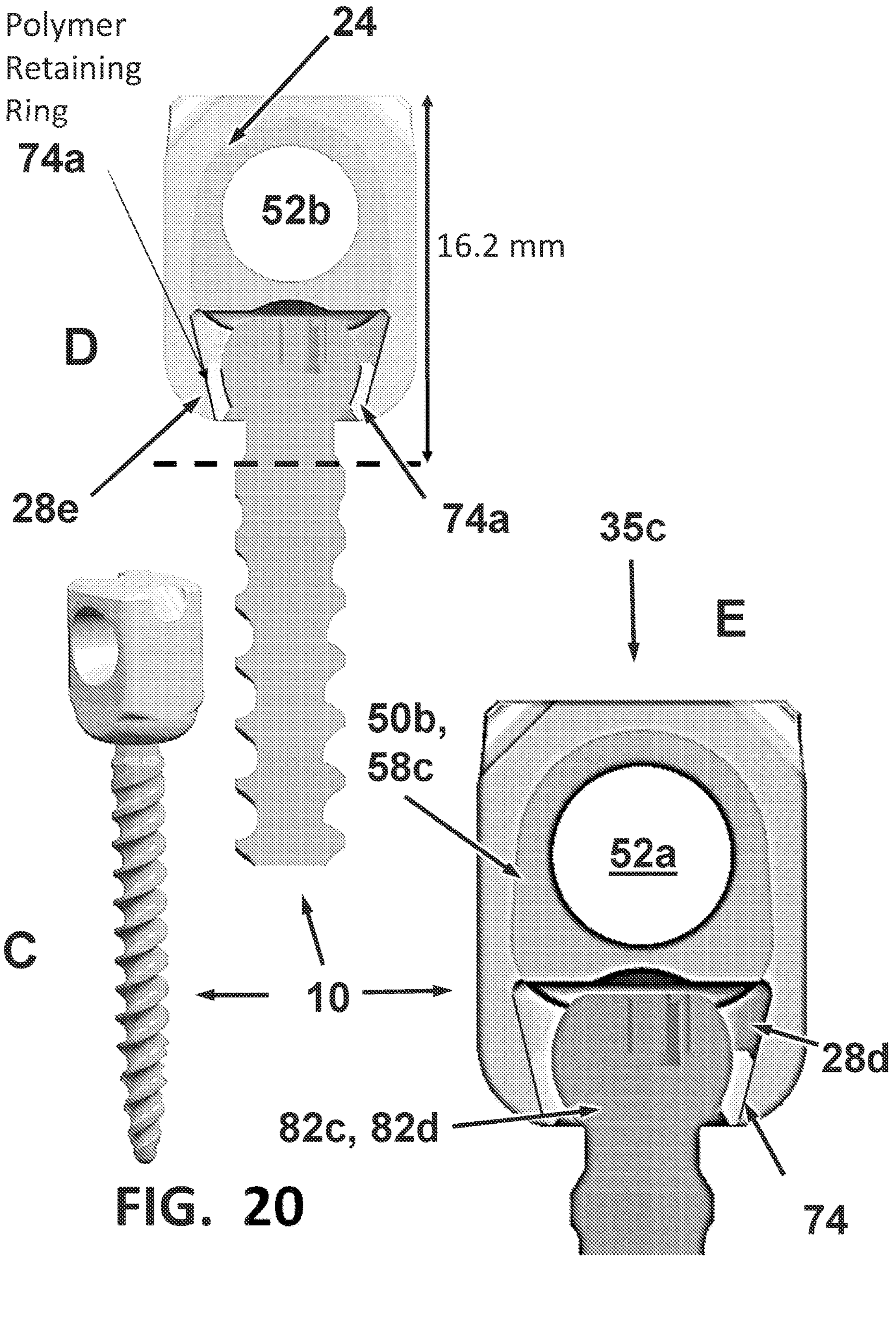

FIG. 20 depicts a guiding anchor 10 according to another embodiment of the present invention. Additional views of the anchor of FIG. 20 are shown in FIG. 33.

Figure 33:
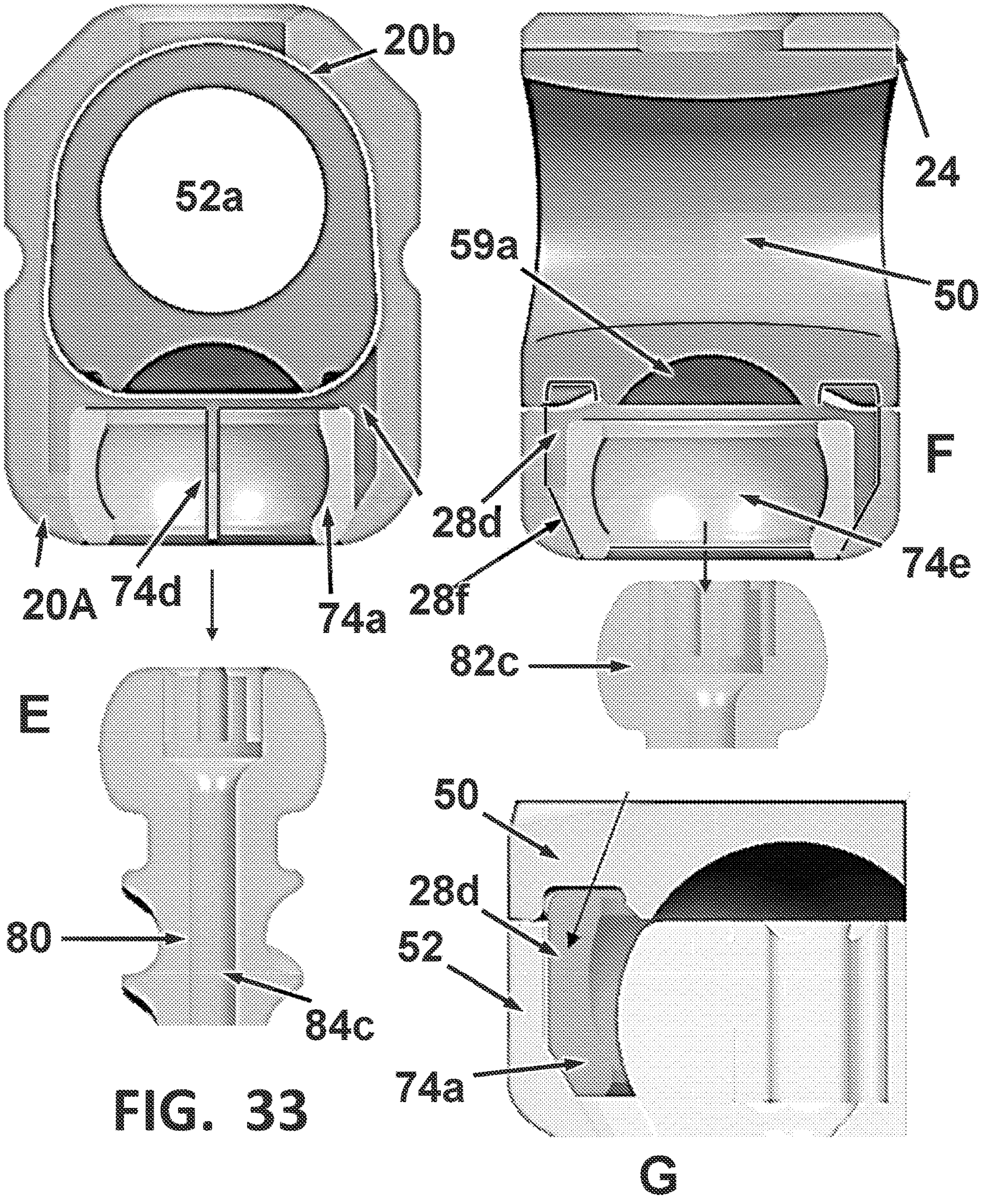
FIGS. 33E-33G show additional views of the apparatus of FIGS. 20A-20E, and including alternative bushing at the interface of the bone attachment device and the head.

The anchor of FIGS. 20, and 33E and 33F are "pop-in," closed tulip preassembled heads 20 that can be inserted as a subassembly onto an implanted anchor 80. In some embodiments, the preassembled, subassembly 20 includes a polymer bushing 50 located within a cavity 24. Head 20 further includes a distally-located tapered pocket 28*f* that includes within it a polymer retaining ring 74*a*. It is noted that various different shapes of polymer ring 74*a* are shown in FIG. 20 and FIG. 33. Preferably, each of them include a slit or fissure 74*d* that permits the retaining ring 74*a* to expand (because the hoop stiffness of the ring is compromised by the fissure) and further permits a reduction in the overall size of the retaining ring (i.e., to the extent of the width of the fissure). Fissure 74*d* is further shown in the enlarged view of FIG. 33E. It is noted that the pocket 28*f* includes a sidewall that is partly cylindrical, and partly tapered. It is further noted that immediately above the ring 74*a* is a pocket 59*a* in bushing 50 that provides clearance space for the device junction 82*c*.

FIGS. 33 and 20 each show a pop-on type of coupling between device 80 and head 20. FIG. 33F shows retention bushing 74*e* in an undeflected state. FIG. 33G shows the expanded state of bushing 74*e* after insertion of the head of the attachment device into the head 20. As the screw head is inserted into the tulip, bushing 74*e* is simultaneously pushed upwards and radially expanded (in embodiments such as that shown in FIG. 33E there can be a slit in the ring that facilitates expansion) until the screw head can pop through. FIG. 33G shows the moment right after pop-through, before the bushing 74*e* begins to contract back down to size. As it tries to return to its relaxed state (in the radial sense) it also "rides" the screw head to its lower position in the tulip. When the screw head is put under tension, the friction and contact angles at the interface keep it from expanding again.

Referring to FIG. 32*f*, it is noted that when head subassembly 20 is placed into contact with the implanted support device 80, that the top of the device junction 82 will push upward against the bottom of retainer ring 74*a*. This upward pressure will move ring 74*a* upward within the cavity 28*f*. In so doing, the pressure of the inner walls of the pocket against the ring is relieved, and ring 74 (because of the fissure 74*d*) is able to expand to a larger diameter, and therefore receive the junction 82*c* within the internal pocket 74*e* of bushing 74. Continued compression of junction 82*c* within head subassembly 20 thereafter results in a bottoming out (i.e., contact of the top of the device junction with the surfaces of pocket 59*a*). When the now-installed head subassembly 20 is pulled away from device 80, the shape of the junction 82*c* will pull ring 74*a* back into the tapered region (as shown in FIG. 32*f*), and thus close around the device junction 82*c*. In this manner, a subassembled head 20 is able to be popped onto an implanted supporting device 80, but is thereafter restrained from being removed.

FIG. 20E shows guiding anchor 10. A second polymeric bushing 74 is received within a pocket of head 20. The head, which includes integrally molded bushing 50*b*, can then be popped on and over the top of device 80. The compression of device junction 82 into the spherical inner surface of bushing 74 by way of a tool (not shown) will result in a pop-in, loose inner connection of device 80 and head 20.

Figure 21:
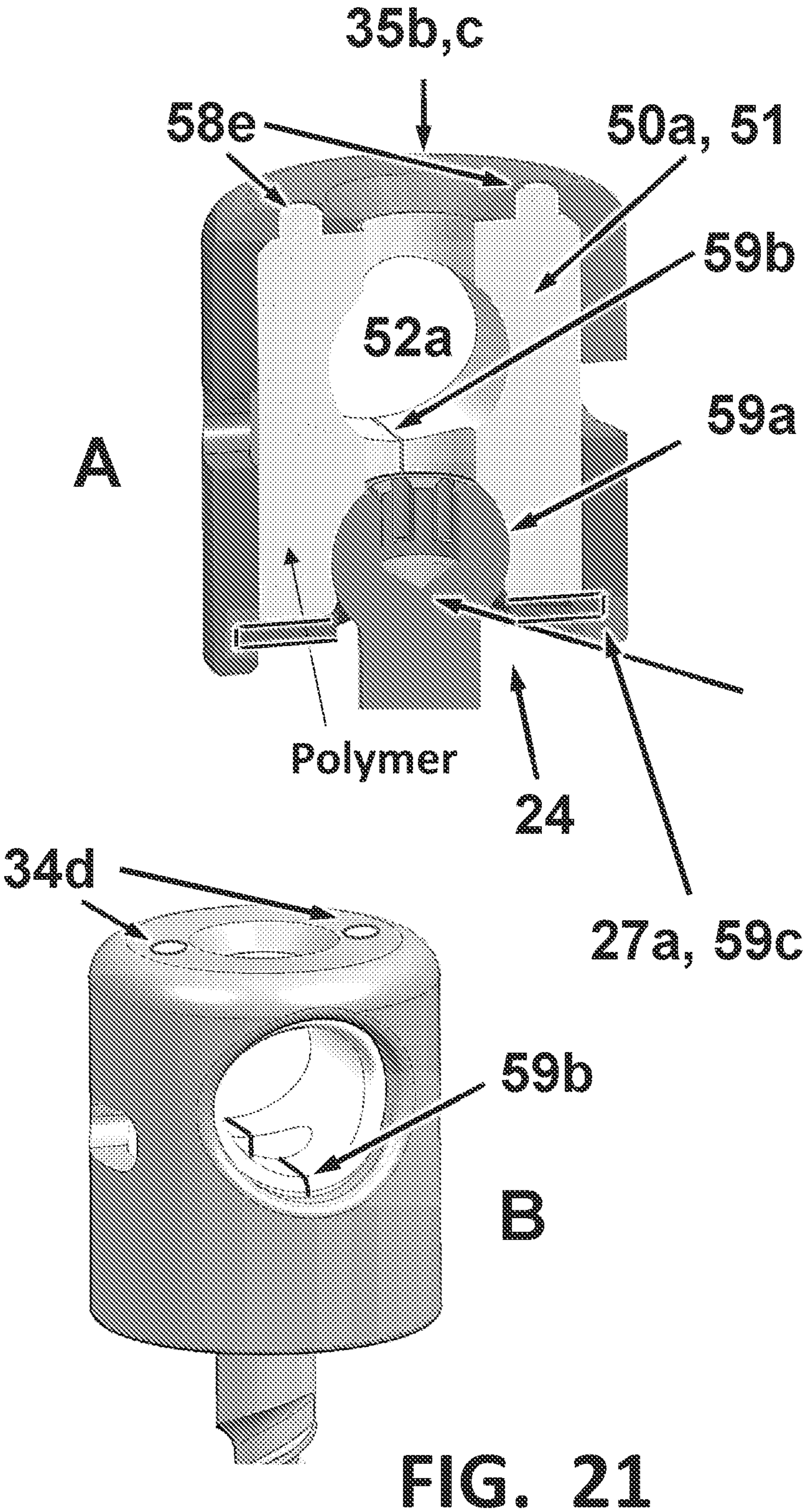

FIGS. 21A and B show a guiding anchor according to another embodiment of the present invention. FIG. 21A shows a split bushing 51 that includes a spherical pocket that accepts within it the spherical device junction 82*c*. This split bushing, with the rod inserted, can be placed vertically downward onto the supporting device 80. The head can be placed over the bushing and supporting device in a vertical direction, with one or more interface pins 58*e* being accepted into corresponding interface apertures 34*d* of head 20.

Anchor 20 of FIG. 21A includes a bushing 50 that incorporates a split or fissure 59*b* between the rod pathway 52*b* and the pocket 59*a* of bushing 50 in which the device junction 82*c* is received. As shown, as one example, device junction 82*c* is spherical, and the pocket 59*a*, although any manner of complementary shapes is contemplated. Because of the pliable nature of the material of bushing 50 and the split 59*b*, bushing 50 can be spread apart so that pocket 59*a* can be fit over top of device junction 82. Preferably, the fit of the device junction within the pocket is a close fit. This preassembly of bushing 50 and support device 80 can then be inserted into cavity 24 from the distal end of cavity 24. In some embodiments, the outer shape of bushing 50 is generally cylindrical, and fits within a generally cylindrical pocket 24. In some embodiments, bushing 50 is not rotationally constrained by head 20. However, as shown in FIG. 21A, a pair of projecting retention features 58*e* (which can be molded or inserted into bushing 50 separately) are received within corresponding apertures 34*d*. The interlocking of the projections and the apertures prevent relative rotation of bushing 50 relative to head 20.

FIG. 21A further shows that after the subassembly of bushing and support device are installed within the cavity, a retaining ring 59*c* (such as a C-clip) is inserted into a slit 27*b* of head 20. Ring 59*c* maintains its position within the slit, and thus prevents removal of bushing 50 (and support device 80) from head 20.

Figure 22:
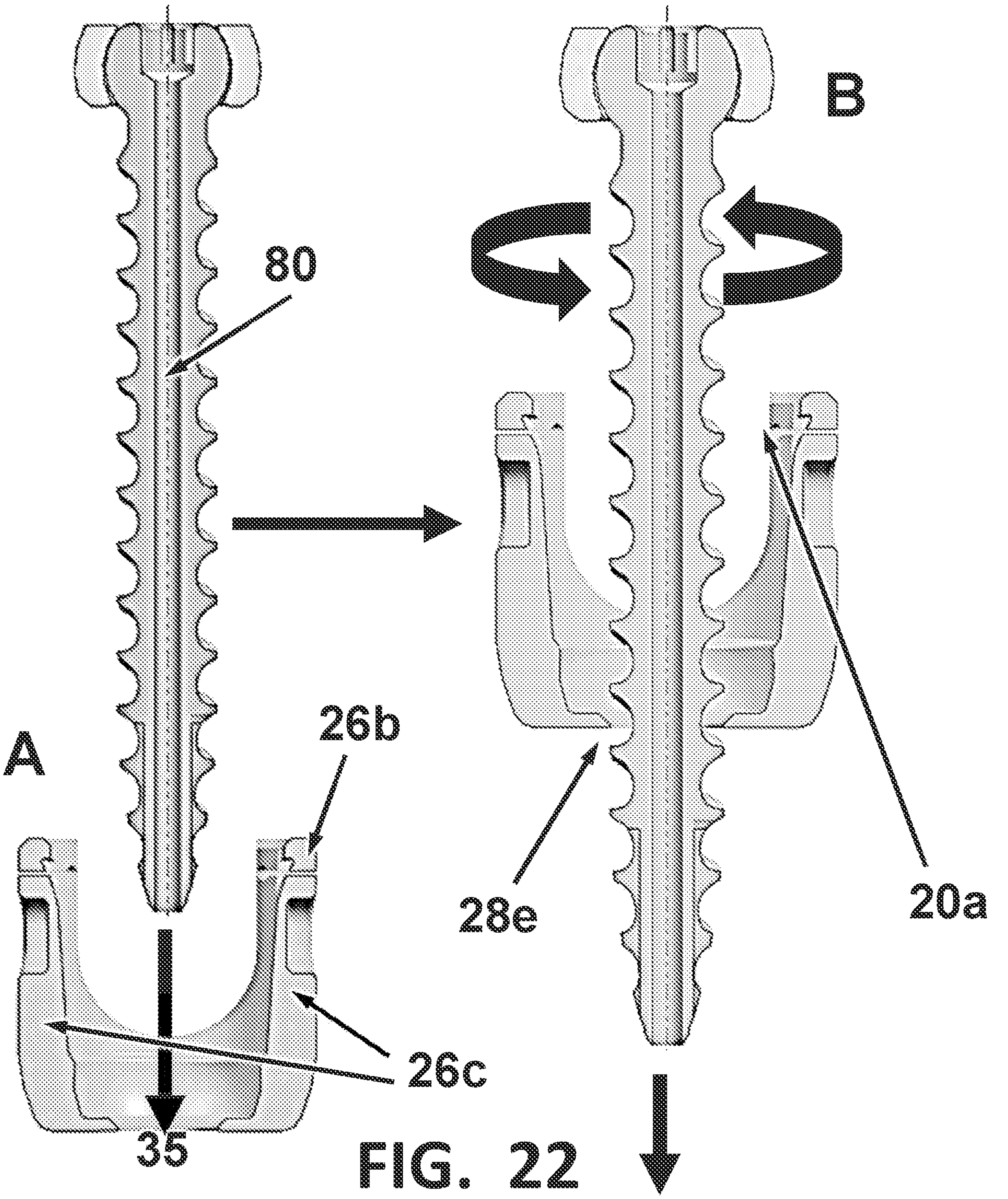
Figure 22:
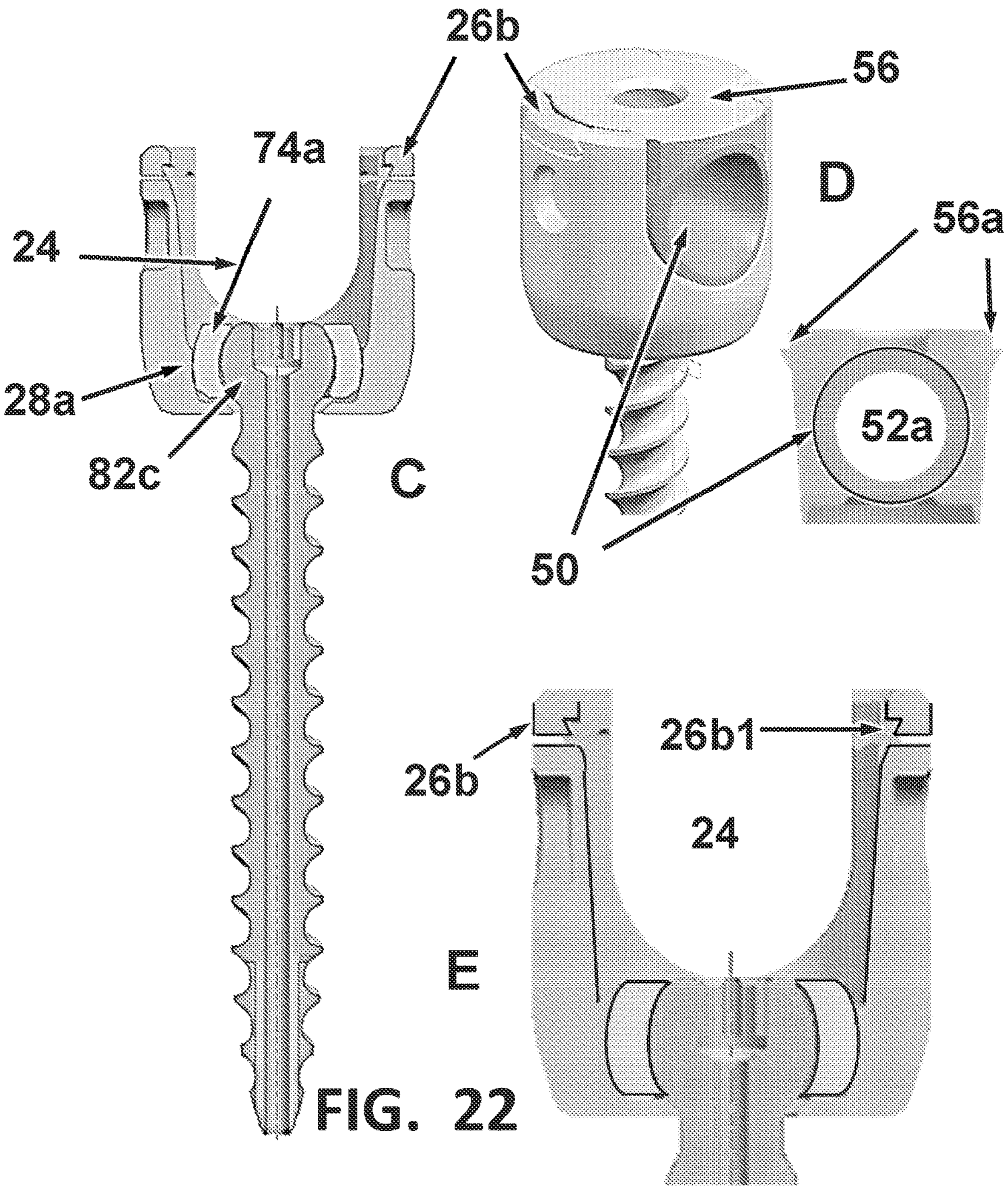

FIG. 22 shows various views of a guiding anchor 10 in which the threaded section 84*b* of a bone screw or other supporting device 80 is threadably received within an aperture 28*e* of a head 20. A second polymer bushing 74 is received around a preferably spherical device junction, and after full engagement into the head 20 the bushing 74 serves as an interface between the device junction 82 and a pocket 28*a* within head 20.

FIG. 22A shows a cannulated supporting device 80 having a distal end adapted and configured for insertion into a bone, and a proximal end having, in some embodiments, a spherical device junction 82*c*. A bearing or bushing 74*a* has been preloaded onto junction 82*c*. Also shown is a head 20 that in some embodiments includes a pair of opposing arms 26*c* defined between them a cavity 24. As shown in FIG. 22B, the assembly of the supporting device 80 and bearing 74*a* can be threaded through an aperture 28*e* of head 20. Preferably, aperture 28*e* has an inner diameter that is larger than the minor diameter of the screw threads, but smaller than the major diameter. In this manner, supporting device 80 can be readily threaded through aperture 28*a*, and loosely maintained by aperture 28.

Referring to FIG. 22*c*, it can be seen that the assembly of support device 80 and bearing 74 are received within a pocket 28 of head 20 that has an internal shape for receiving the outer surface of bearing 74*a* with minimal side play, and preferably permitting polyaxial rotation of support device 80 relative to head 20.

An enlargement of the assembly of head 20, support device 80, and bearing 74*a* is shown in FIG. 22D. In some embodiments, at least one of the opposing arms 26*c* includes a spring arm 26*b* that can be elastically cantilevered radially outward in order to fit around the head retention features 56*a* of bushing container 56. These cantilever spring loaded arms (connected to the head by live hinges) snap back into place once the corresponding retention feature 56*a* is received within the notch 26*b*1 indicated in FIG. 22D. Once the live hinge returns the arm 26*b* back to its normal state (as shown at the top of FIG. 22D), the placement of the retention feature 56*a* within groove 26*b*1 discourages any attempt to remove container 56 in a proximal (vertical) direction, unless a tool is used to radially and preferably elastically move the arms 26*b* out of contact. It is further appreciated from FIG. 22D that the underside of bushing container 56 is shaped so as to fit over the assembled junction and bearing within head 20, and thus not restrain pivotal motion by physical interference or rubbing.

Figure 23:
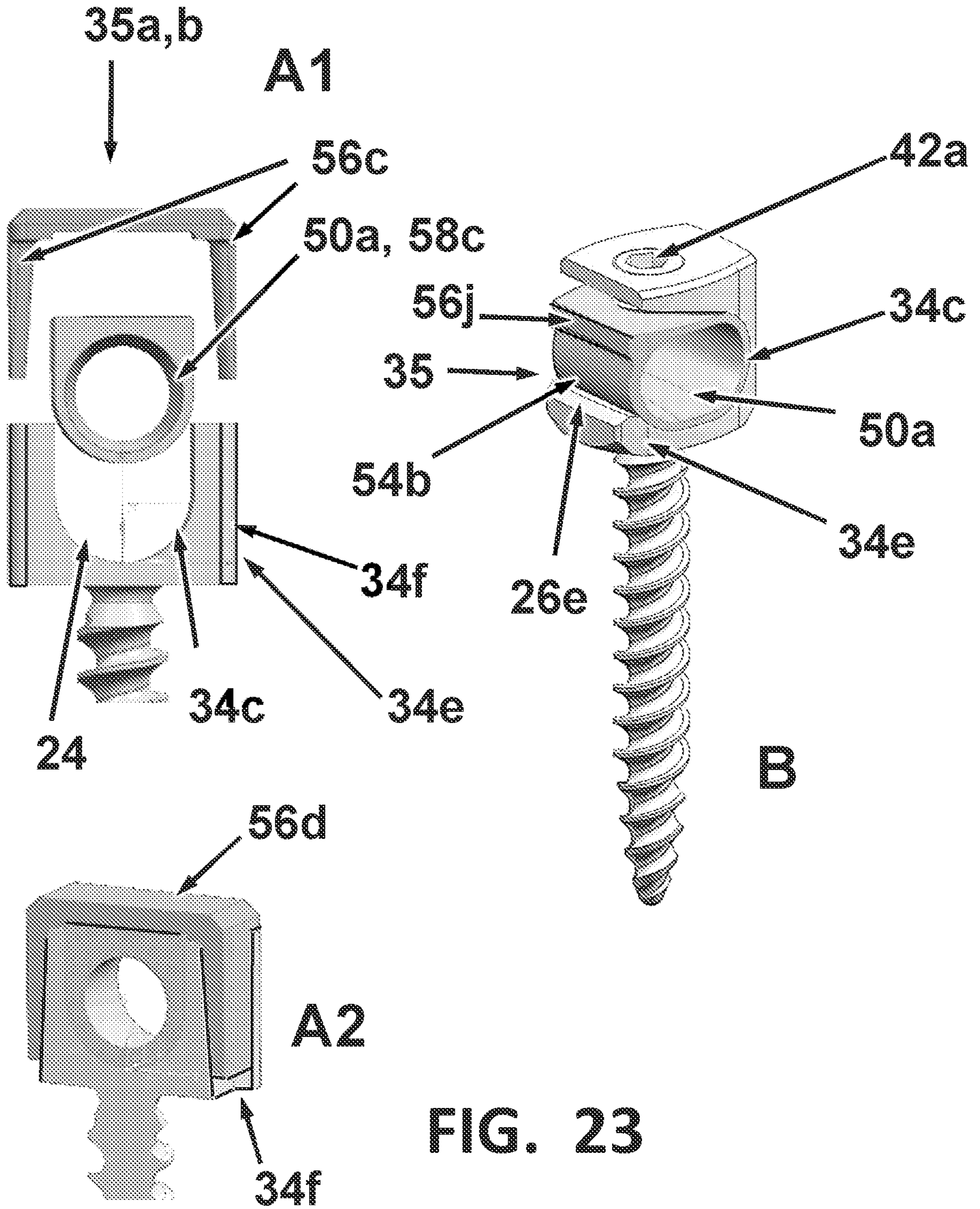

FIG. 23 shows various guiding anchors having different methods and apparatus for retaining a bushing such as a bushing comprising or coated with a polymeric, metallic, or ceramic material within a head 20. FIGS. 2431 and A2 show a separable polymeric bushing 50*a* received within a container having a pair of tapered locking arms 56*c*. Bushing 50 has an external shape 58*c* that is adapted and configured to fit within a correspondingly shaped bushing interface 34*c* of head 20. After insertion of the bushing into the head (preferably with the rod) the connector 56 can be pressed onto head 20, and snap into a retained position as the arms 56*c* spread out over a corresponding projection on the sides of the head. In FIGS. 234A1 and A2, the opposing arms 56*c* are each received within a corresponding groove or slot 34*f*, each located on opposing sides of head 20.

FIG. 24B shows a bushing 58 that is inserted along a slightly elevated angle (relative to horizontal), and then placed within the pocket 34*c*. A set screw 42 presses downward on the top of the bushing, and the bushing is captured in the head by the coaction of the set screw and the lip 34*e*.

Figure 24:
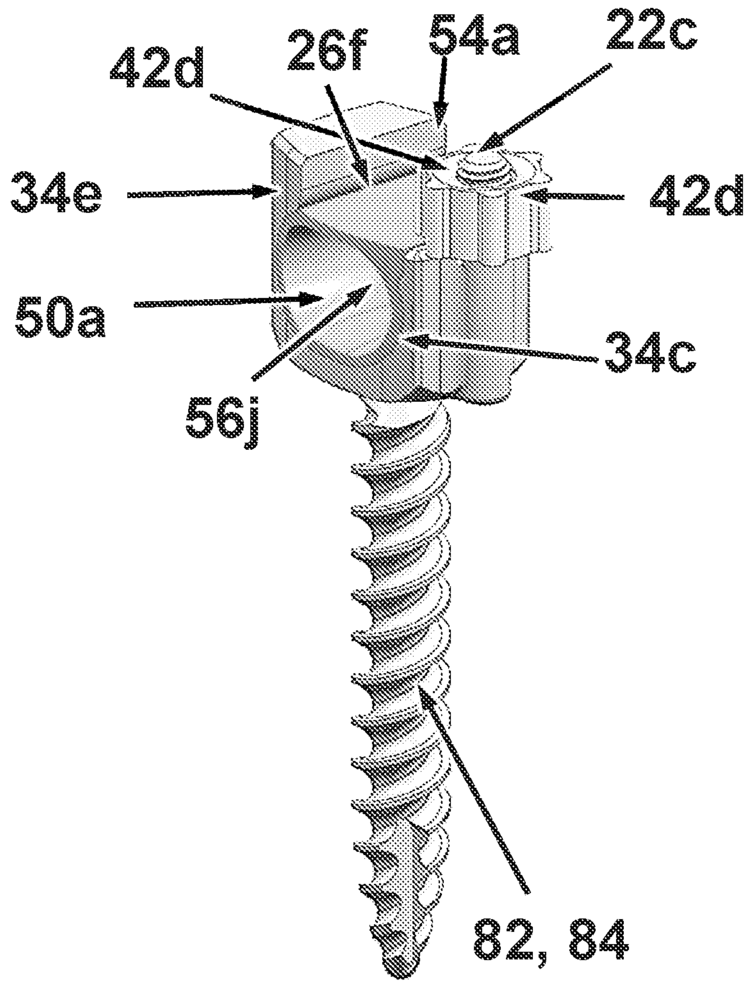
FIG. 24 shows a side elevational, perspective view of an assembled anchor according to another embodiment of the present invention, and using a set screw that is offset from the axis of the bone anchor.

FIG. 24 shows a head and bushing design similar to that of the column second from the left, except that the lip 34*e* is located along the top of the head, and the set screw is coupled to the head by internal threads 42*b*. The coaction of the top lip 34*e* and the overhanging set screw 42 combine to obstruct any attempt to remove bushing 50.

Referring to FIG. 23A1, an anchor 10 is shown having a head 20 that includes an oblong bushing interface 34*c* that is open at the top. A bushing 50*a* is received within cavity 24, and because of the flattened lateral sides of both the bushing and the cavity, bushing 50 can slide into cavity 20, but cannot rotate within cavity 20.

After being nested within cavity 20, a U-shape taper lock bushing container 56*c* is placed across the top and opposing sides of head 20. Container 56 includes a pair of downwardly (distally) depending arms 56*c*, each which are received within a corresponding lateral channel 34*f* of head 20. Referring to the bottom, assembled view, it can be seen that the channel 34*f* is open as to one corner of the received arm 56*c*, but wraps around the corner of the same outward face of the same arm. Because of this channeled, grasping feature of channel 34*f*, an arm 56*c* cannot be laterally pivoted away from head 20. In some embodiments, each arm 56 further includes a lip or edge 34*e*. In those embodiments, the tapered arms can include a complementary-shaped feature at the distal ends of the arms, such that downward motion of the container 56 onto channel 20 results in the arms 56*c* snapping over the retention features 34*e*. However, as shown in FIG. 2432, each opposing arm can further be constrained within a multi-sided channel by friction.

FIG. 23B shows an anchor 10 in which a bushing 50 is loaded in the direction 54*b* from the side through a side opening 26*e* in head 20. In some embodiments, and as shown in FIG. 23B, the opening 26*e* preferably includes an upwardly projecting lip or ledge 34*e*. Because of this ledge, the insertion of bushing 50 is both lateral and slightly angled downward, and once inserted, the bushing is retained from lateral movement by the inner surface of ledge 34*e*. Referring to the top under surface of the side opening 26*e*, it can be seen that this top surface is angled upward, in a direction so as to cooperate with the angled insertion of the bushing.

After insertion, a set screw 42*a* can be coupled to head 20, such that the bottom side of the set screw comes into obstruction with any attempt to angularly move the installed bushing upward, thus preventing inadvertent removal. Preferably, the bushing 50 includes a thickened area 56*j* (such as the top corner shown in FIG. 23B) which provides both increased strength for potential contact with set screw 42*a*, and also for grasping purposes during insertion. Although the coupling of heads 20 in FIGS. 23A, 23B, and 24, is shown as being fixed to support device 80, it is understood that any of the other head to device coupling geometries can also be incorporated.

FIG. 24 shows a variation of the concepts of FIG. 23B, except as rearranged for top loading. Head 20 preferably includes a top opening 26*f* through which a bushing 50*a* can be inserted. Preferably, there is a ledge 34*e* that extends part way over the top of bushing 50. As referred to with the anchor of FIG. 23B, this ledge 34*e* aids in the retention of a bushing 50*a* that has been inserted downward from the top, and further angled into cavity 24. In some embodiments, head 20 includes a threaded post 22*c* onto which a set nut 42*d* can be installed and tightened. Set nut 42*d* has an outermost width that is sufficiently large enough to extend over the edge of the top opening 26*f*, so as to impede any attempt to remove bushing 50 from cavity 24. Bushing 50 likewise incorporates a thickened portion 56*j* to aid in insertion and improve distribution of contact stresses.

Figure 25:
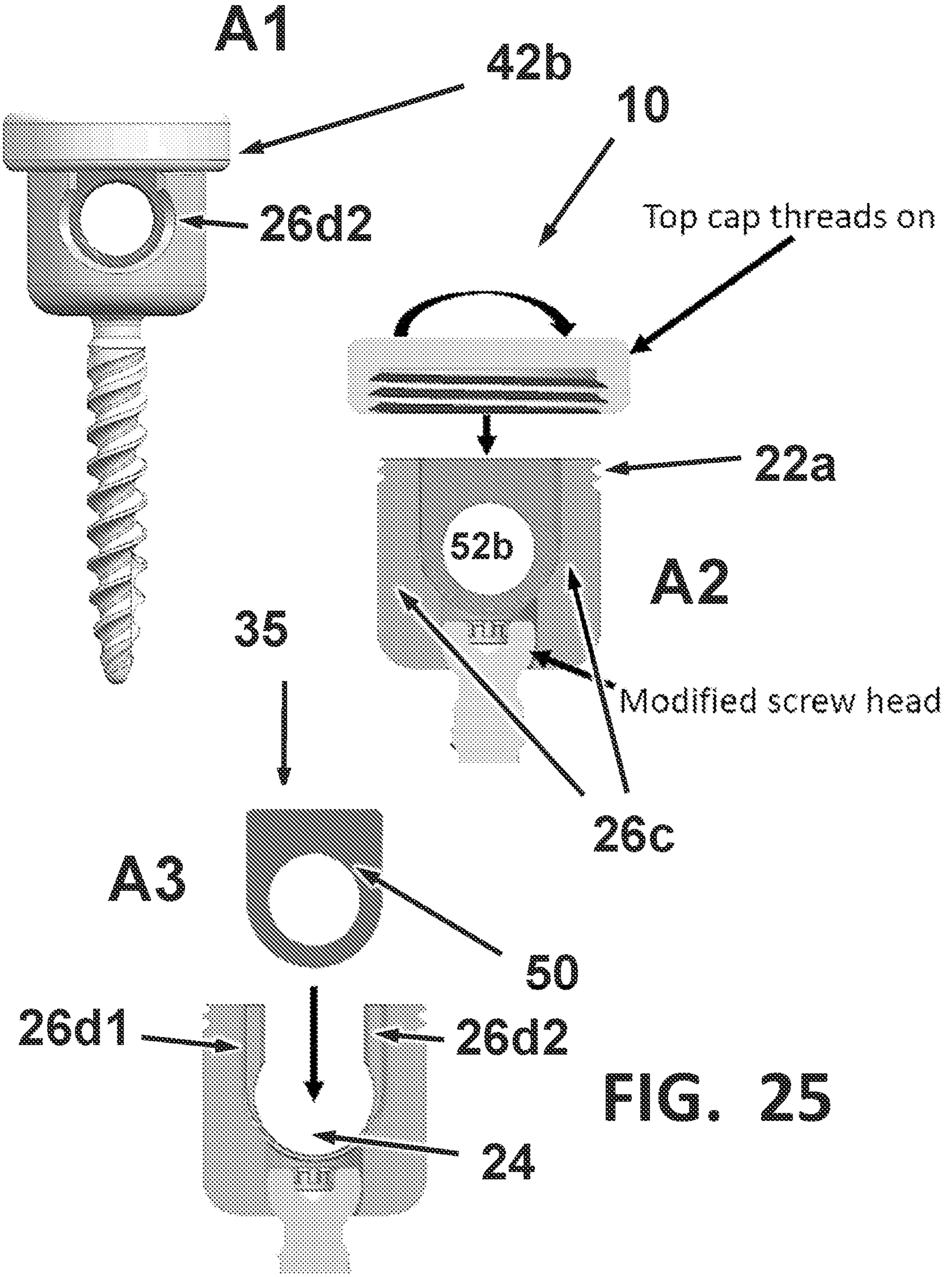
Figure 26:
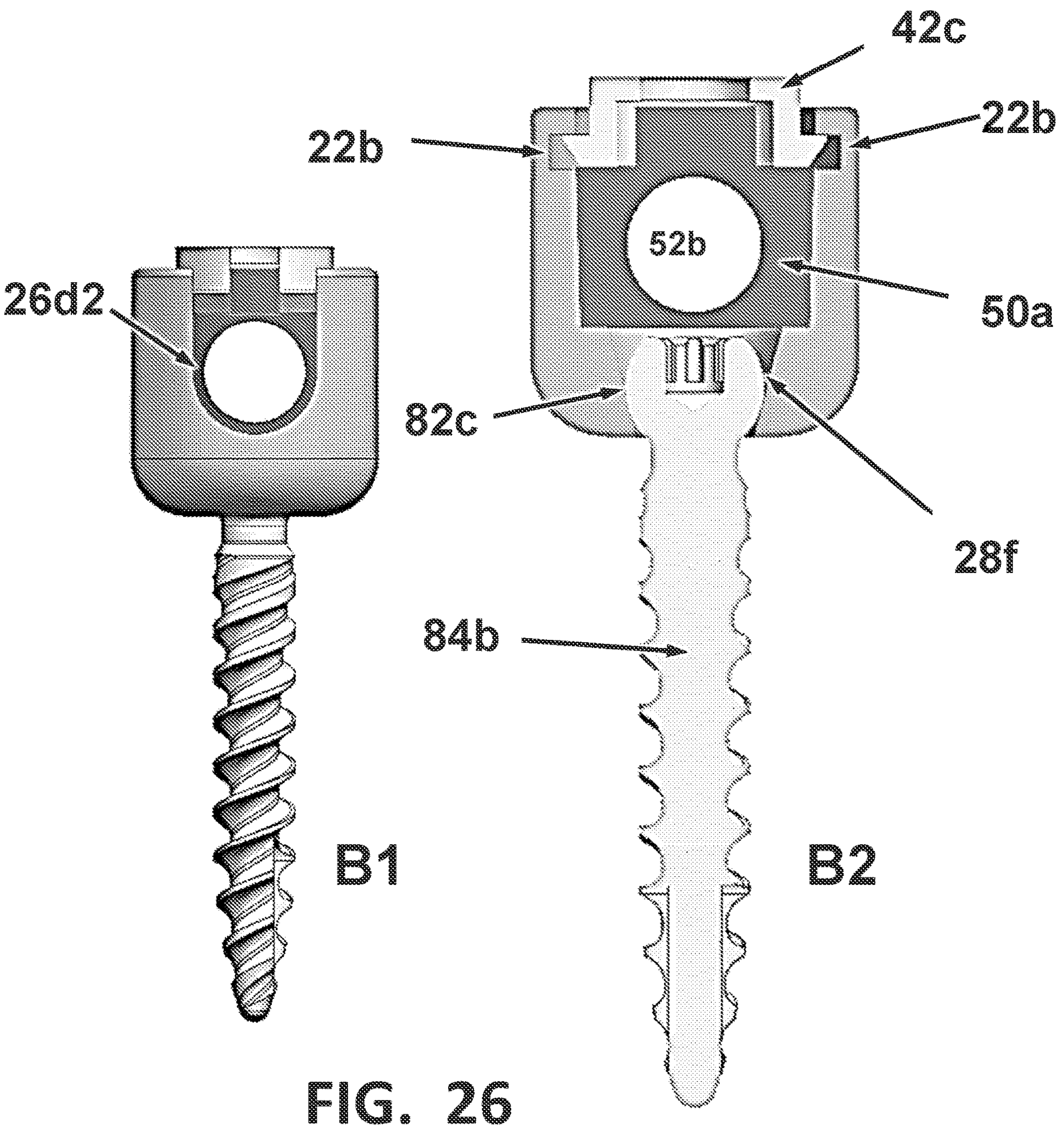
Figure 26:
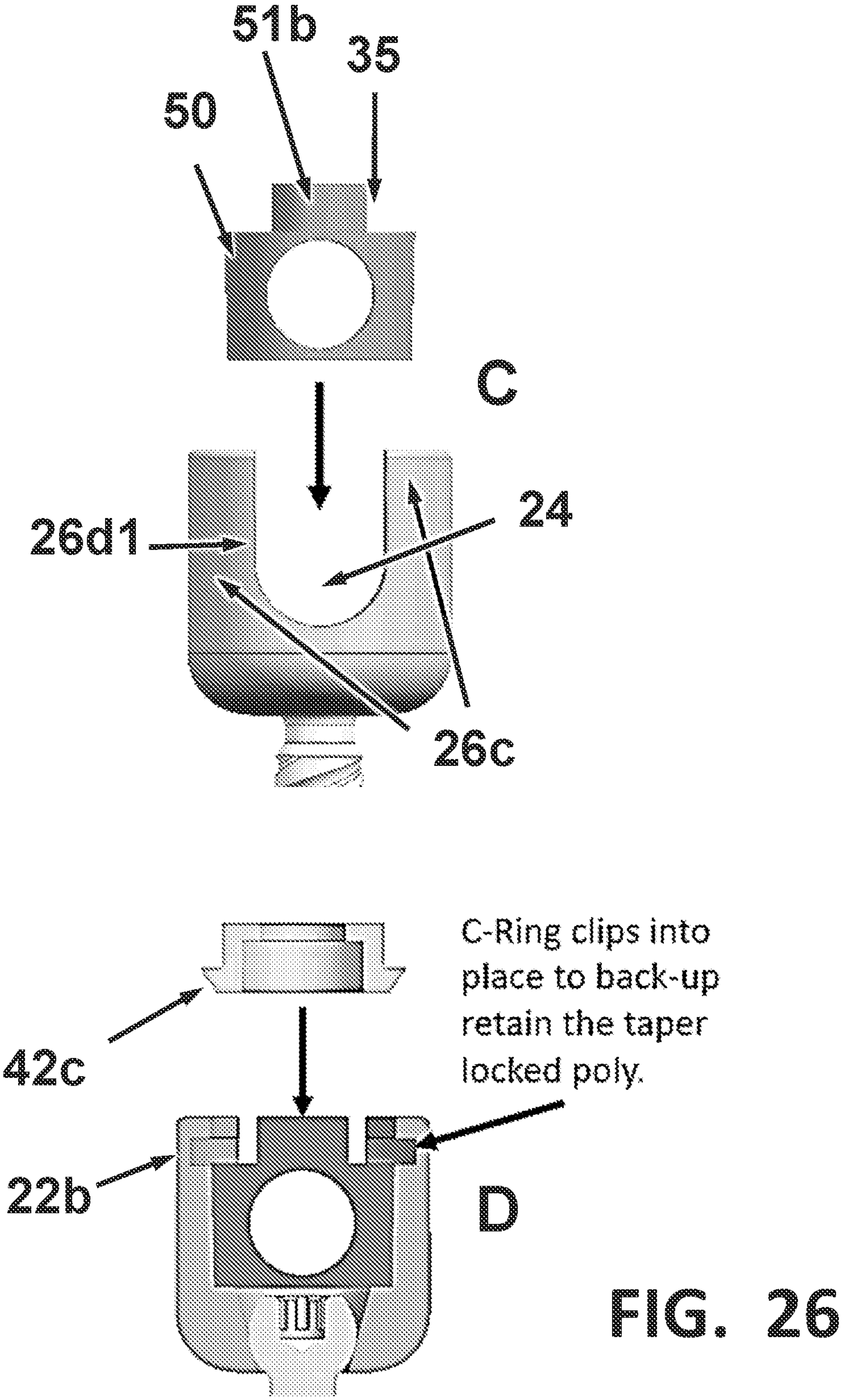

FIGS. 25 and 26 show a pair of guiding anchors according to different embodiments of the present invention. FIGS. 25A1, A2, and A3 show an anchor in which the bushing 50 (preferably with the rod inserted) can be inserted vertically into a pocket of the head 20. The bushing can be retained within the head by a set screw 42*b* having internal threads that threadably engage external threads 22*a* of head 20.

FIG. 25A shows an anchor head 20 including a pair of parallel arms 26*c* that define between them a cavity adapted and configured for receiving within it a bushing 50. Preferably, cavity 24 includes a bushing container interface 26*d*1 that is complementary in shape to a portion of the bushing 50. As can be seen in FIGS. 25A and 25B, this shape 26*d*1 includes generally flat, parallel sides. The complementary fit of bushing 50 within such a cavity 24 minimizes or eliminates any relative motion of the bushing relative to the head 20. After a bushing 50 has been inserted from the top into cavity 24, a cap 42*b* having internal threads is threadably coupled to external threads 22*a* on head 20. Once the cap is tightened, cavity 24 is closed and bushing 50 is contained within it. It is further noted with regards to the drawing at the bottom of FIG. 25A that the opposite sides of the cavity 24 include narrower bushing retention features 26*d*2 that surround the portions of the bushing around rod pathway 52*b*. Therefore, by having an internal cavity that is wider (between walls 26*d*1) at the center and narrower (between walls 26*d*2) at the end, bushing 50 cannot be removed along the rod axis.

The anchor 10 shown in FIGS. 26B1 and 26B2 also captures a bushing 50 within an internal cavity 24 having wider and narrower side walls 26*d*1 and 26*d*2, respectively, for receiving therein a bushing 50. In some embodiments, bushing 50 preferably includes a top projection or button 51*b* that is adapted and configured to be received with a retention mechanism 42. The anchor of FIG. 26 incorporates a C-clip 42*c* that fits within a slot or groove 22*b*, as best seen in figure of FIG. 26D. A middle figure of FIG. 26B2 shows a cross sectional view in which the C-clip is captured within groove 22*b* and surrounding the projection 51*b*. In some embodiments, portions of the clip 42*c* come into contact with a top annular surface of bushing 50. FIG. 26B2 shows a guiding anchor 10 in which the spherical device junction 82*c* is received within a tapered pocket 28*f* of head 20. A separable polymeric, metallic, or ceramic bushing (or coating) 50*a* is received within an internal pocket of head 20, and held in place by a c-clip retained within a groove 22*b*.

Figure 27:
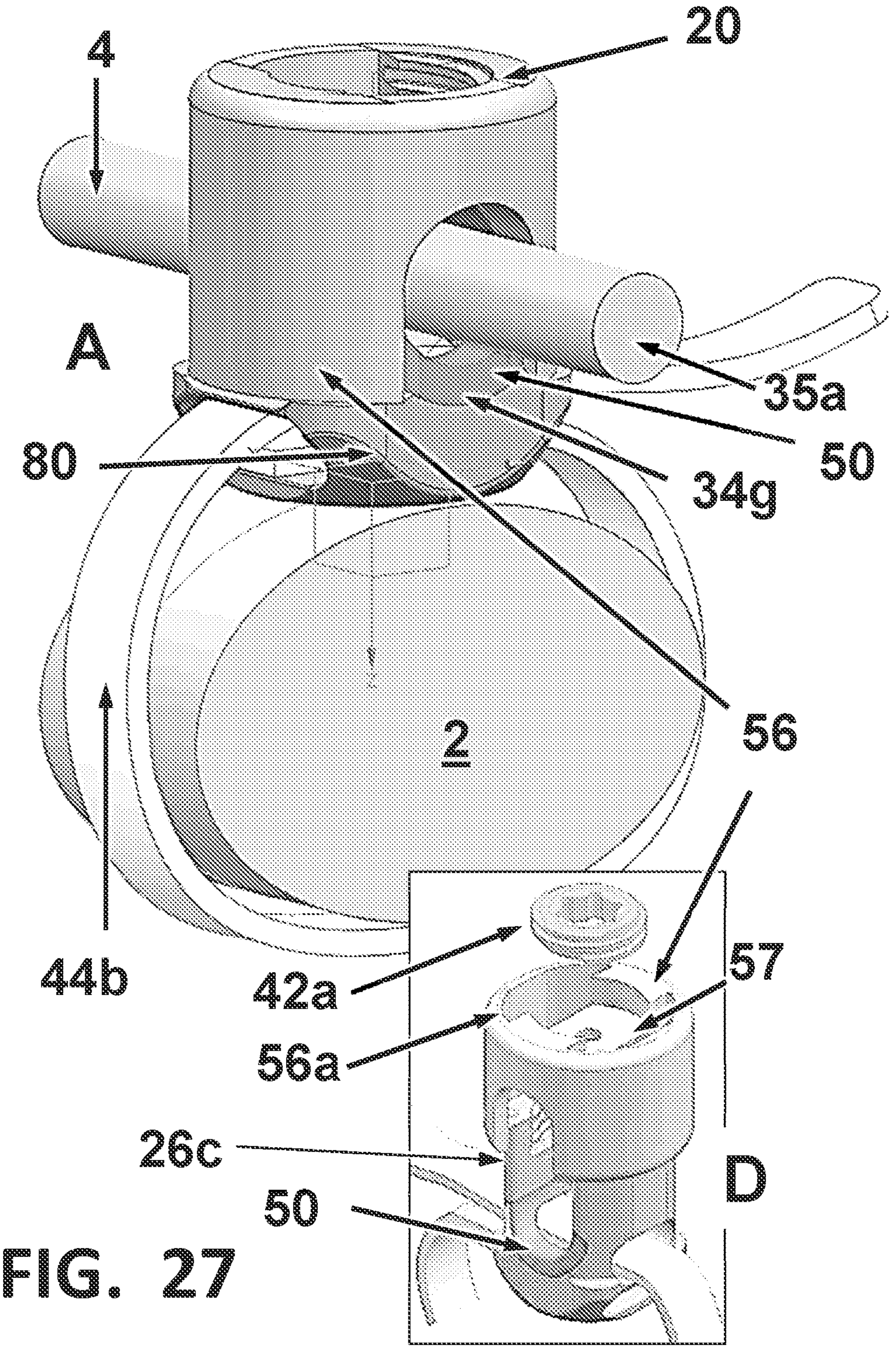
FIGS. 27 and 28 show an anchor assembly according to another embodiment of the present invention.
Figure 28:
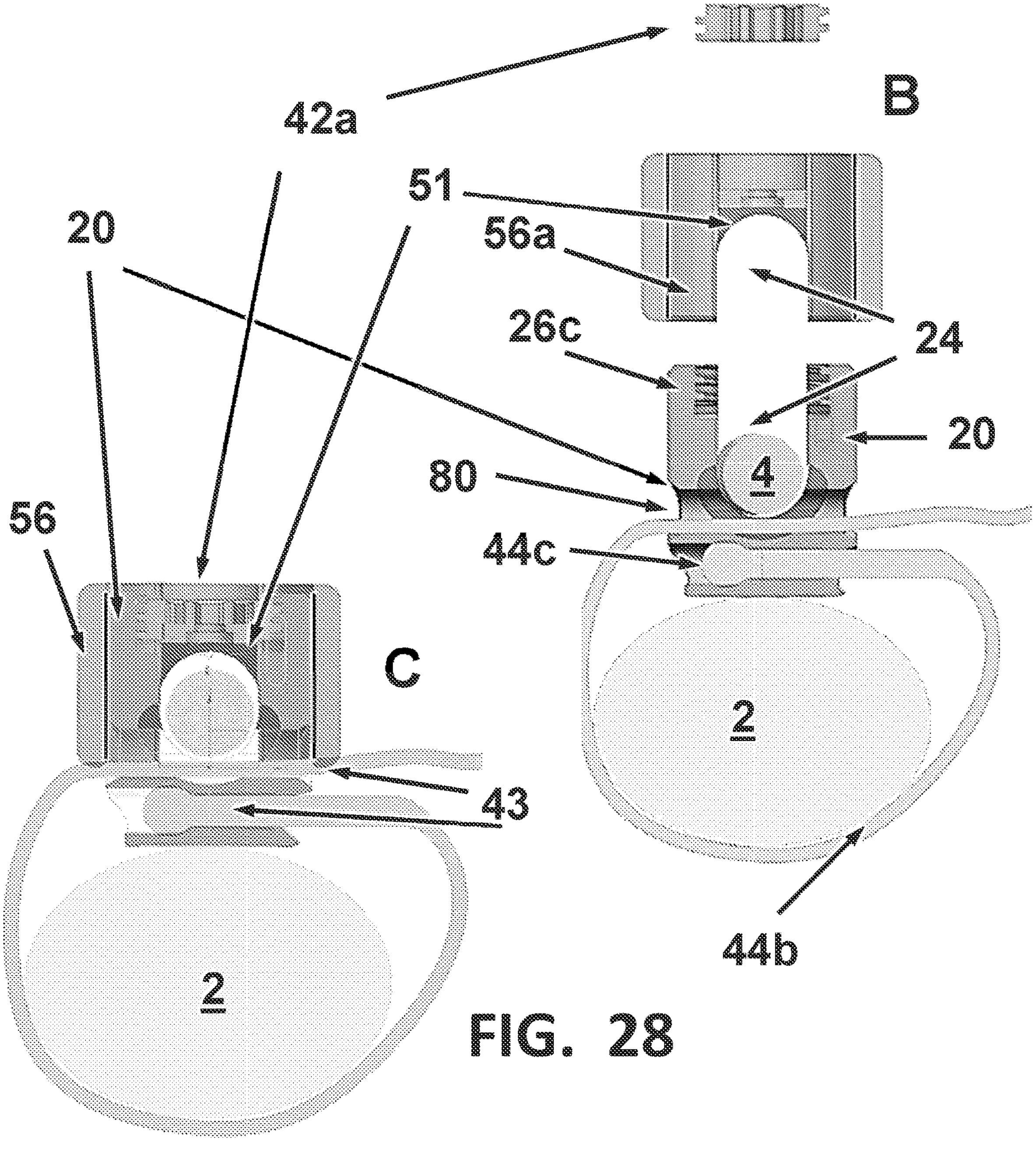

FIGS. 27 and 28 shows a guiding anchor 10 according to another embodiment of the present invention. Head 20 is constrained to a vertebra 4 by a loop 44*b* of a flexible connector, in a manner similar to the BandLoc (™, Ortho-Pediatrics Corporation) anchors. Head 20 includes a polymeric bushing 50 that provides a pathway 52 for a rod 4. The head 20 can be assembled onto the rod, and subsequently attached by connector 44 to the vertebra. After the loop 44*b* is sufficiently tight, a threaded cap 45 is installed to capture the bushing and compress the flexible connector.

FIGS. 27A, 28B, 28C and 27D show different views of an anchor 10 in which the support device 80 comprises a pair of slots 43 integrated into head 20, and coupled to a bone by a flexible loop 44*b* around a vertebrae in a manner similar to that shown in U.S. Pat. No. 9,173,685, issued Nov. 3, 2015, titled TETHER CLAMP & IMPLANTATION SYSTEM and U.S. Pat. No. 10,595,904, issued Mar. 24, 2020, titled TENSIONING INSTRUMENT & BAND CLAMP TENSIONING SYSTEM, incorporated herein with regards to description of the manner of using a flexible container for retention around a bone, and except as inconsistent with the description provided herein.

FIG. 27A shows a head 20 located at least in part internally within a bushing container 56. Bushing container 56 includes a first segment 51 of a polymeric bushing, and adapted and configured to be installed in the top of cavity 24. It is noted that cavity 24 is partly incorporated in container 56, and partly incorporated in head 20. In the bottom of cavity 24 (within head 20) is a bushing 50 located within a groove 34*f* of head 20.

Preferably, head 20 includes a pair of threaded opposing arms 26*c* that wrap around the bottom portion of cavity 24. Referring to FIG. 28B, it can be seen that these opposing arms are received within corresponding head retention features 56*a*. In some embodiments, these retention features 56*a* have a shape that is complementary to the shape of the arm 26*c*, as best seen in FIG. 27D. In some embodiments, as these arms 26*c* are fully received within slots 56*a*, as best seen in FIGS. 27A and 28C, the top surfaces are generally flush.

Referring to FIGS. 28B and 27D, it can be seen that a set screw 42*a* can be threadably received by the arms 26*c*, and when fully tightened received within a topmost chamber 57 of container 56. As the set screw is tightened, the bottom of the set screw pushes against the upper surface of the pocket 57, and locking together the head 20 and container 56. The interface between head 20 and container 56 is adapted and configured such that a portion of the bottom of container 56 presses against the flexible connector 44 within the topmost slot 43, and as shown in FIG. 28C. This compression of connector 44 places sufficient friction on connector 44 so as to discourage any relative movement of connector 44 relative to head 20, in a manner similar to that discussed with the anchors of FIGS. 15 and 16. Further consistent with those figures, preferably an end of the connector passing through the bottom slot includes a connector retention device, such as an enlarged head that can be received within the entrance to the bottom slot 43, but which is too large to pass through the slot 43 itself.

Figure 29:
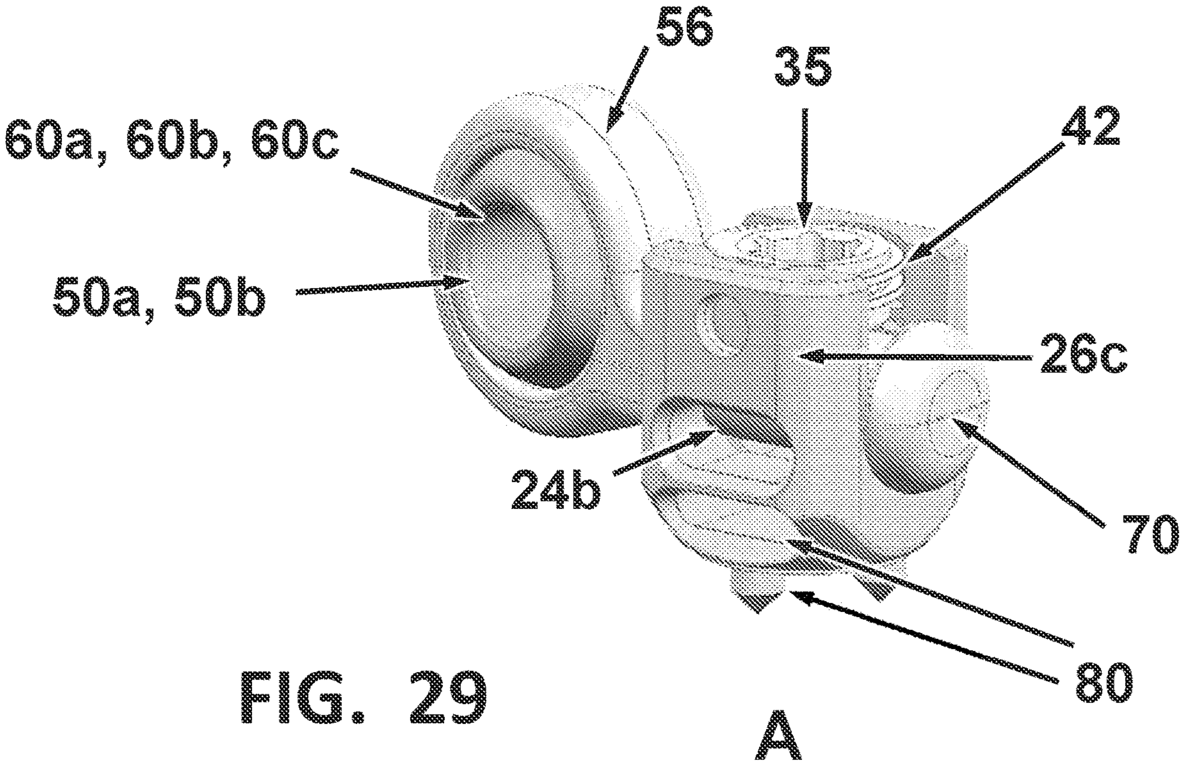
FIGS. 29A-29C show various views of an anchor assembly according to another embodiment of the present invention.
Figure 29:
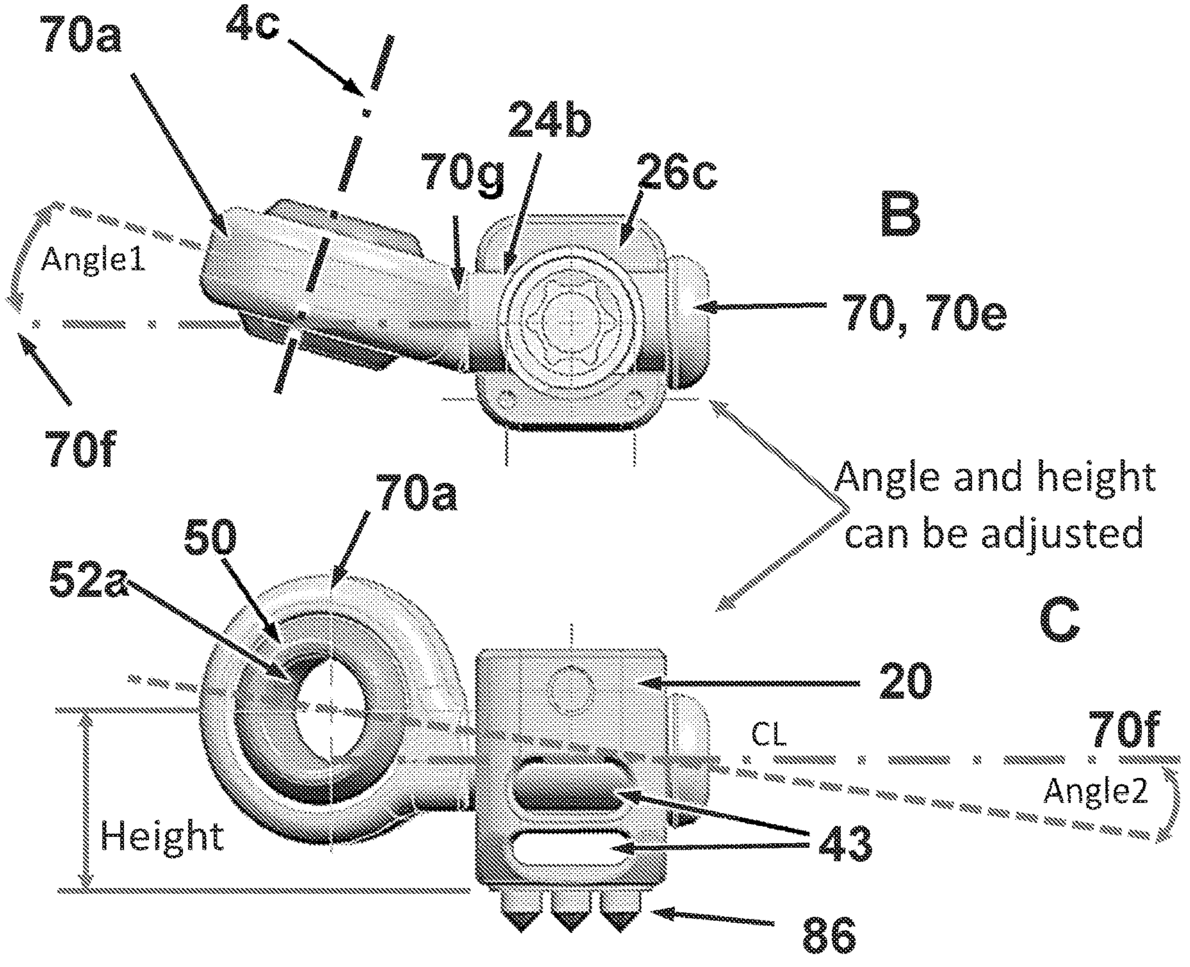

FIG. 29 shows one embodiment of a guiding anchor 10 according to another embodiment of the present invention, and the same as previously discussed with regards to FIG. 13C2. It can be seen that in some embodiments the first ring 70*a* of support arm 70 is set at an angle relative to the portion of the support arm that is received within a pocket of head 20.

FIG. 29 shows an anchor 10 according to another embodiment of the present invention, and as previously shown and discussed with regards to FIG. 13. Anchor 10 includes a bushing container 56 comprising a ring 70*a* supported from a rigid arm 70*g*. Referring to FIG. 29B, it can be seen that the rigid arm extends through a cavity 24*b* within a head 20. One end of the support arm 70 includes an enlarged head 70*e* that has a width greater than the width of the opening between the arms 26*c*. Rod 70 is inserted within cavity 24*b* in a direction 35 from above. A set screw or other device coacts with the arms 26*c* to enclose the cavity and constrain support arm 70 therein. In some embodiments, set screw 42 is locked into the threaded interface with head 20, but bearing only minimally on arm 70 and not preventing rotation of the arm within the cavity. In still other embodiments, the set screw 42 is locked in the threads and maintains the roll angle of arm 70 relative to head 20.

Ring 70*a* of container 56 supports a bushing 50 that can have any type of rod interface, such as, by way of example, a rod to bushing interface that is cylindrical 60*a*, semi-spherical 60*b*, non-cylindrical or oblong 60*c*, including rod pathways that are offset from the centerline of the bushing outer diameter.

The arm 70 is further adapted and configured to provide various angular and translational offsets of the rod 4 (not shown) relative to head 20. Referring to FIG. 29B, it can be seen that the ring 70*a* supports a pathway 52*a* for a rod that is laterally (i.e., in yaw) offset from the axis 70*f* of arm 70 as established by cavity 24 by an Angle1. Referring to FIG. 29C, support arm 70 can further be established at a pitch Angle2 relative to centerline 70*f*. This angular offset Angle2 can further change the Height of the rod pathway above the implantation site. Further, FIG. 29C shows that this Height can be adjusted as arm 70 is rotated within cavity 24. In some embodiments of the present invention, a support arm 70 can be offset as indicated by Angle1, or by Angle2, or by a combination of both. In some embodiments, it is contemplated that there are kits in which a plurality of arm assemblies 70 are provided, each with a different relationship of Angle1 and/or Angle 2.

Referring to FIG. 29C, it can be seen that there are a pair of slots 43 between cavity 24 and one or more implantation spikes 86 (the latter aiding in maintaining the position of anchor 10 on a bone). In some embodiments, slots 43 provide a means for attaching anchor 10 to a spine by a flexible connector 44, as discussed previously with regards to FIGS. 28, 15, and 16. However, yet other embodiments contemplate any manner of support device 80 shown herein.

Figure 30:
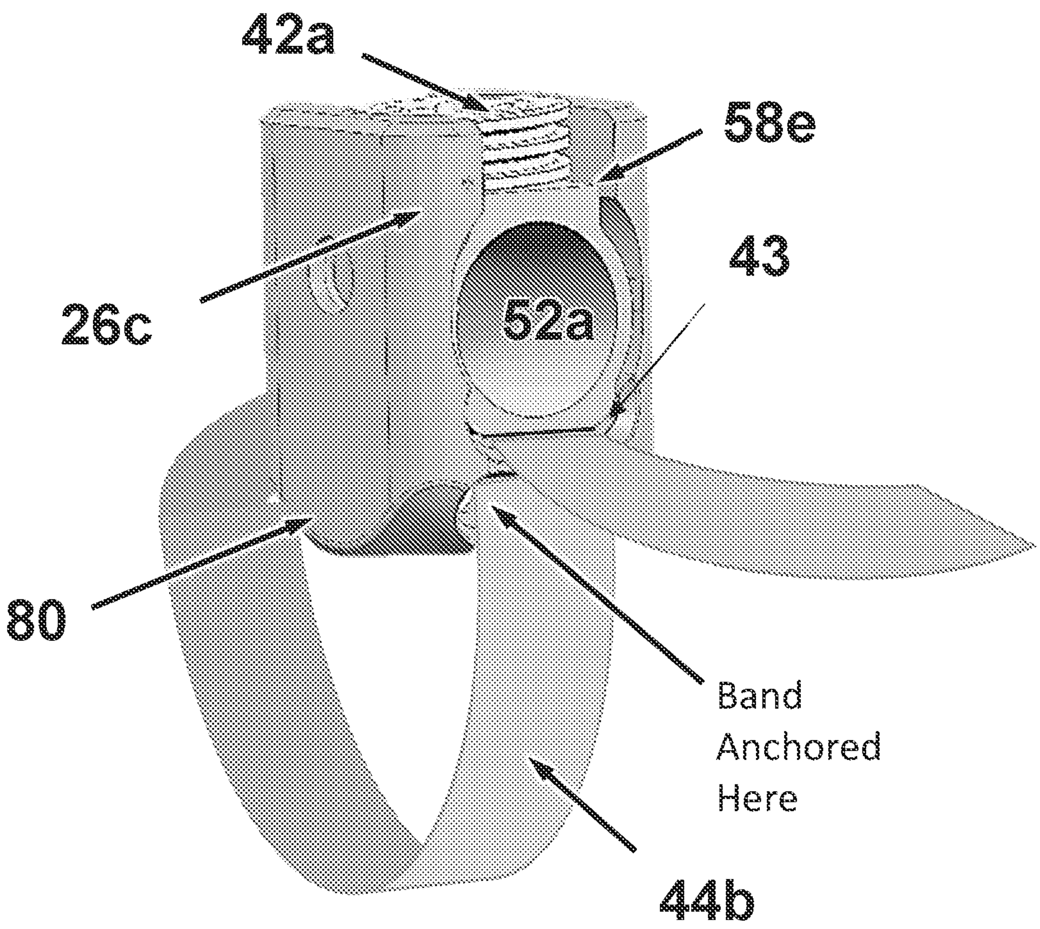
FIGS. 30 and 31 show an anchor according to another embodiment of the present invention.
Figure 31:
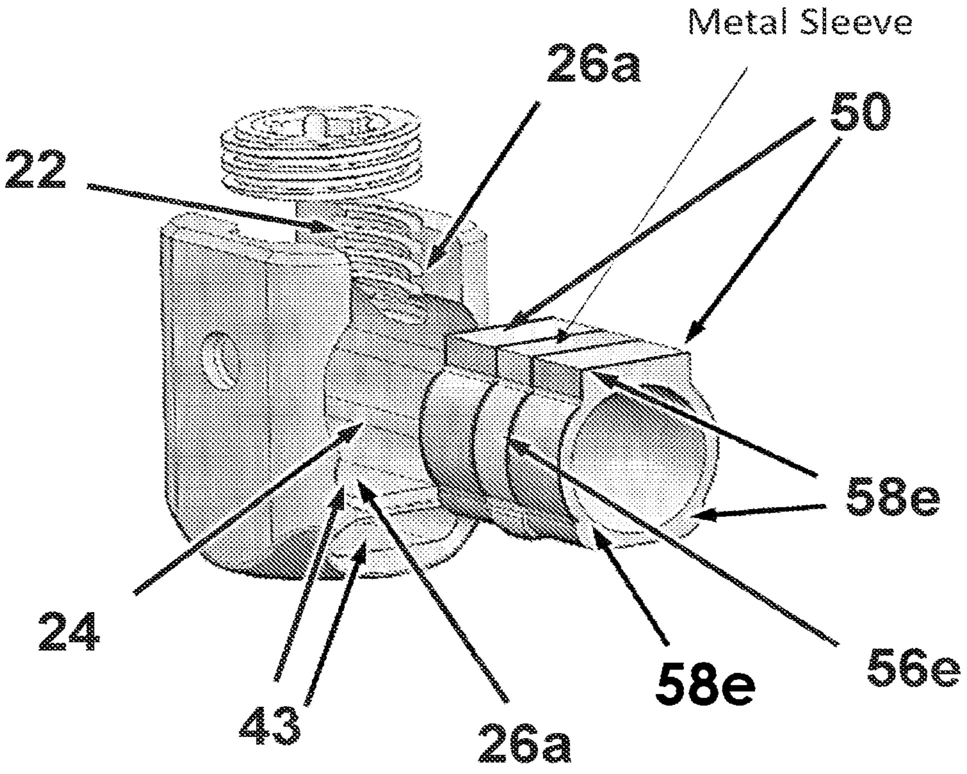

FIGS. 30 and 31 show a guiding anchor 10 according to another embodiment of the present invention, and similar to the guiding anchor of FIGS. 9A and 18A and 18D, except that in FIG. 30 the head 20 is anchored to a vertebra by a loop 44*b* of flexible connector, as discussed with regards to FIG. 29.

The anchor 10 of FIGS. 30 and 31 includes a bearing container 56*e* that supports the midsection of a bushing 50. As best seen in the exploded view of FIG. 30B, an assembly of a bearing container 56*e* and bushing 50 have an external shape that is generally complementary to the internal shape of a cavity 24 of head 20. In some embodiments, the bushing container includes retention features 58 shown as squared-off top and lower ledges. These ledges are further carried into each of the sides of the bushing 50 (as shown), although it is understood that in yet other embodiments the squared-off ledges (or other retention features) are present only on the central container 56*e*.

Preferably, container 56*e* is a ring that has molded onto it a bushing 50 on either side. In yet other embodiments the bushing 50 may be a unitary body, with a ring 56*e* placed around a central portion.

The bushing container assembly is preferably inserted in a direction along the rod pathway 52*a*. After it is in place within cavity 24, a set screw or other retaining device 42*a* can be attached to head 20 and tightened so as to apply a compressive, frictional force onto sleeve 56 (and in some embodiments, also on to one or more of the bushing portions 50).

Head 20 preferably includes a pair of slots 43, one of which extends between head 20 and the bottom of the bushing assembly, and the other of which extends within an additional slot underneath this first slot (in a manner similar to that shown in FIG. 28). In a manner similar to that shown in FIG. 28C, the compression of the bushing retainer 42 onto bushing container 56*e* results in a frictional, compressive locking force onto the portion of the flexible connector extending between head 20 and the underside of bushing 56*e*. Preferably, a connector retention device 44*c* is located on the end of the flexible connector that extends through the bottommost slot.

Although what has been shown and described is the connection of anchor 10 by way of a support device comprising a flexible connector, it is understood that head 20 can alternately incorporate any of the support devices 80 shown herein. In some embodiments, anchor 10 further includes an orientation of slots 43 that provide for tension of the flexible connector 44 in a direction generally parallel to rod pathway 42*a*. In contrast, it is noted that the slots 43 shown in the anchor of FIG. 28 are oriented so as to be placed in tension by application of a force that is generally orthogonal to the direction of the rod pathway.

Figure 34:
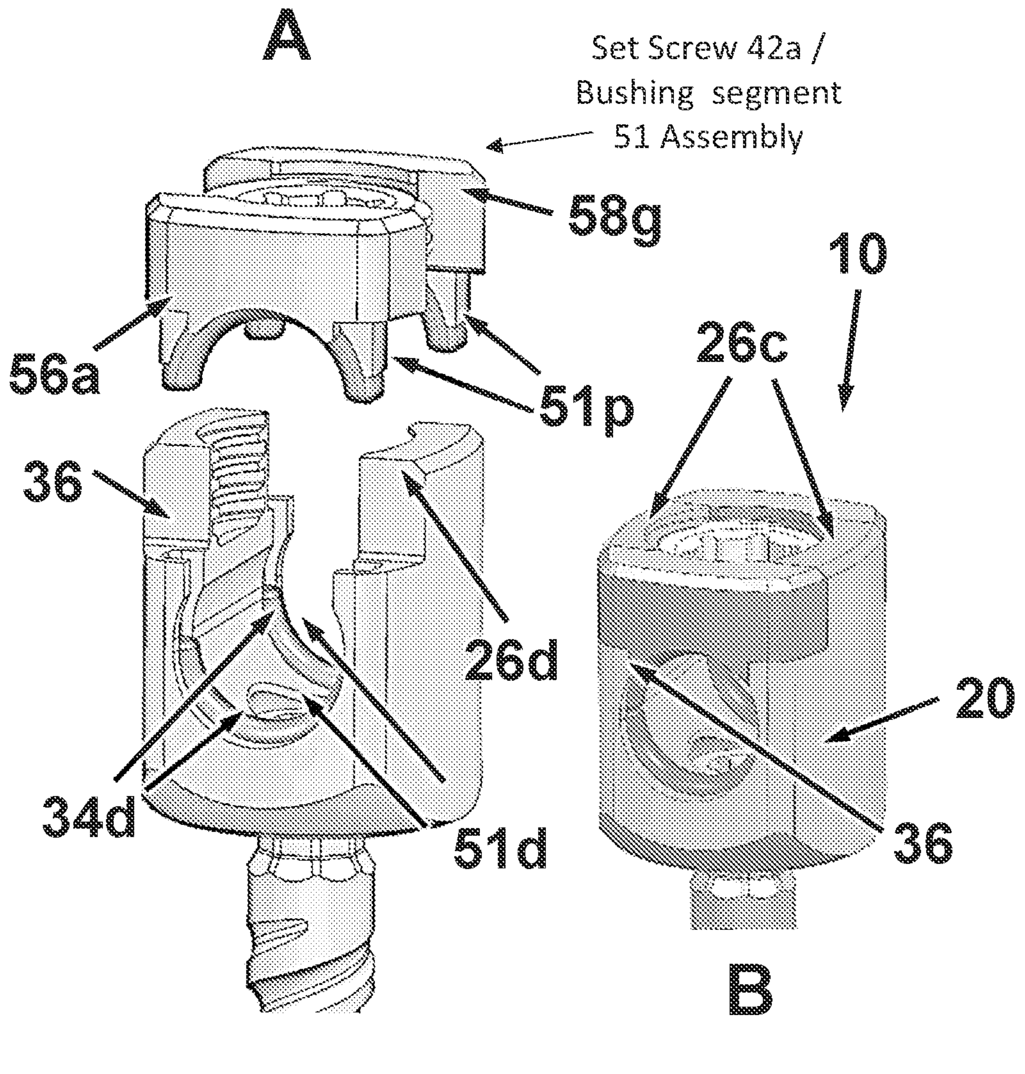
FIGS. 34A-34D present various views of an anchor according to another embodiment of the present invention.
Figure 34:
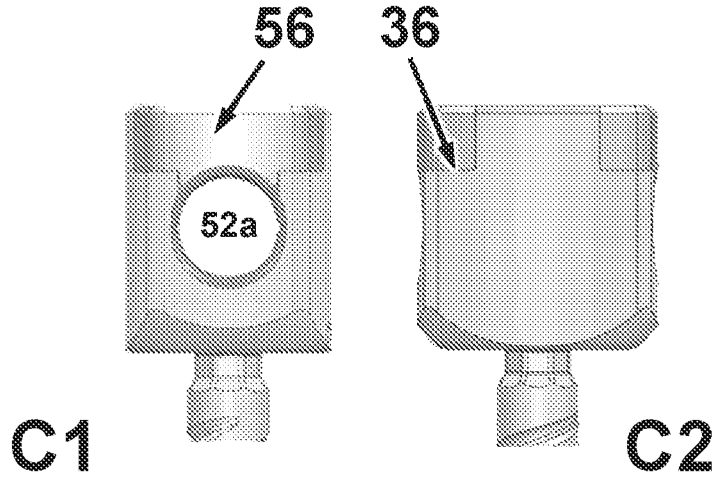
Figure 34:
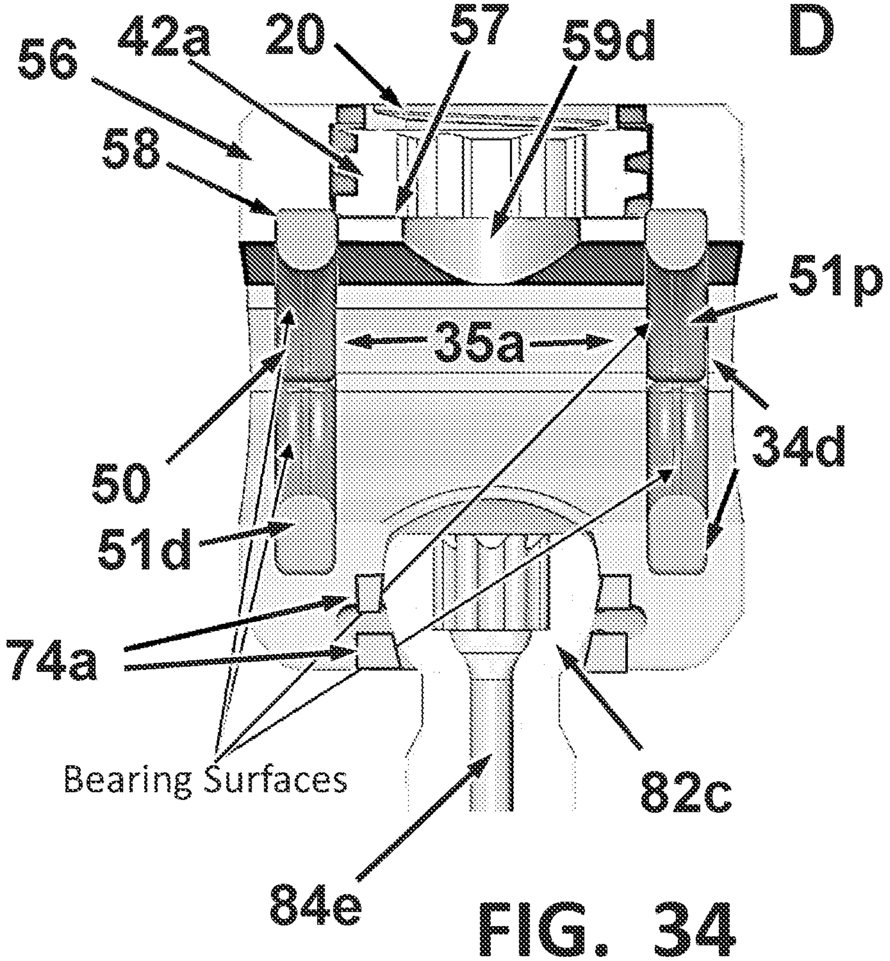

FIG. 34 shows various views of an anchor according to another embodiment of the present invention; FIG. 34A shows a perspective, partly exploded view; FIG. 34B shows a fully assembled, perspective view; FIGS. 34C1 and C2 show front and side views, respectively, of the assembled anchor; and FIG. 34D shows a cross section of the assembled anchor, taken along the axis of the rod pathway.

FIG. 34 show various views of an anchor 10 that includes a split polymeric bushing that supports both sides of a rod. FIG. 34A shows an exploded view, having a bushing container 56 that includes within it a pair of proximally-located bushing segments 51*p*. Further shown is a head 20 having a pair of opposing, internally threaded arms 26*c* that includes a pair of distally-located bushing segments 51*d*, each arranged in a corresponding groove 34*d*. In some embodiments, each of the proximal segments 51*p* and the distal segments 51*d* provide, when fully assembled, three hundred and sixty degrees of interface with a rod within pathway 52*a*. However, the present invention also contemplates those embodiments in which any of the bushing segments can be of lesser arcs, such that there can be a gap in the surrounding of the rod. Referring to FIG. 34D, it can be seen that the distal segments 51*d* are each retained within a corresponding groove 34*d*. The bushing segments 51*p* are likewise each received within corresponding grooves or pockets 58. In some embodiments, the bushing segments are separate, whereas in other embodiments the bushing segments are integrally molded with the corresponding head or bushing container.

Bushing container 56 further includes head retention features 56*a* that are adapted and configured to be received within corresponding bushing container retention features 36 placed within head 20. As best seen in FIGS. 34A and 34B, the bushing container features 56*a* each downwardly depend from the bottom of container 56, preferably defining a portion of the groove 58, and are slidably received within slots 36. The mating of extensions of 56*a* and slots 36 assists in providing accurate line-up of the ends of the bushings 51*p* within the top portion of grooves 34*d* (as best seen in FIG. 34D). These downwardly depending ends of segments 51*p* thus overlap, being contained in both a groove within the bushing container, and when assembled also within a groove of the head. Referring to FIG. 34D, it can be seen that the split line between the head and bushing container is preferably located above (proximal) to the centerline of the assembled rod.

Anchor 10 of FIG. 34 includes still further features that locate container 56 relative to head 20. Referring to FIG. 34A, it can be seen that head 20 includes a generally flat surface 26*d* that abuts against a corresponding flattened head interface 58*g*. Referring to FIGS. 34B and 34C1 and C2, it can be seen that the abutment of each bushing container interface 26*d* with each head interface surface 58*g* provides for an interlocking or clocking of container 56 onto head 20. Referring to FIG. 34D, it can be seen that the bushing container further includes a through aperture 59*d* through which a support device 80 can be manipulated.

Figure 35:
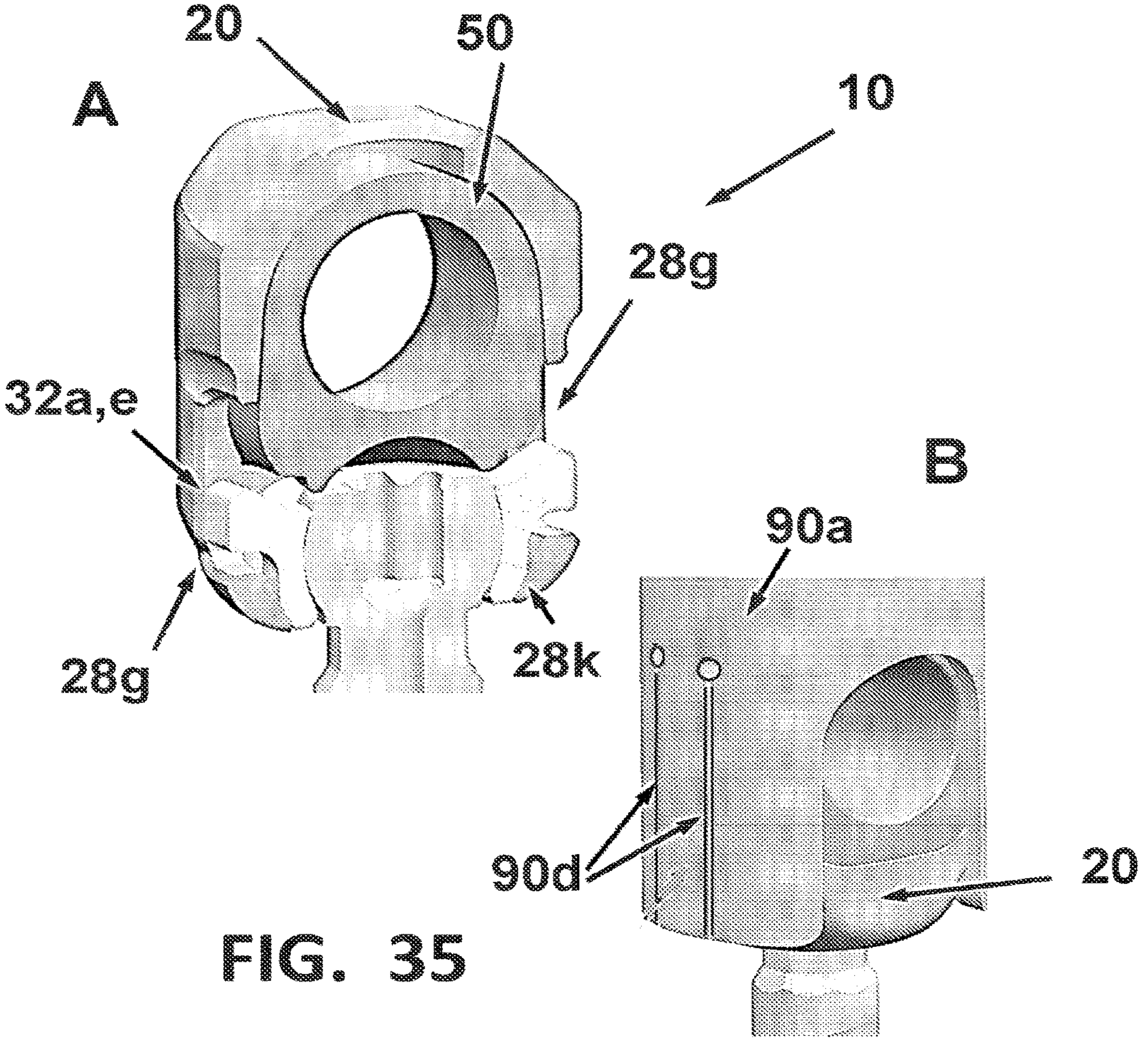
FIG. 35 show various views of an anchor according to another embodiment of the present invention along with instrumentation for removal of the anchor.
Figure 35:
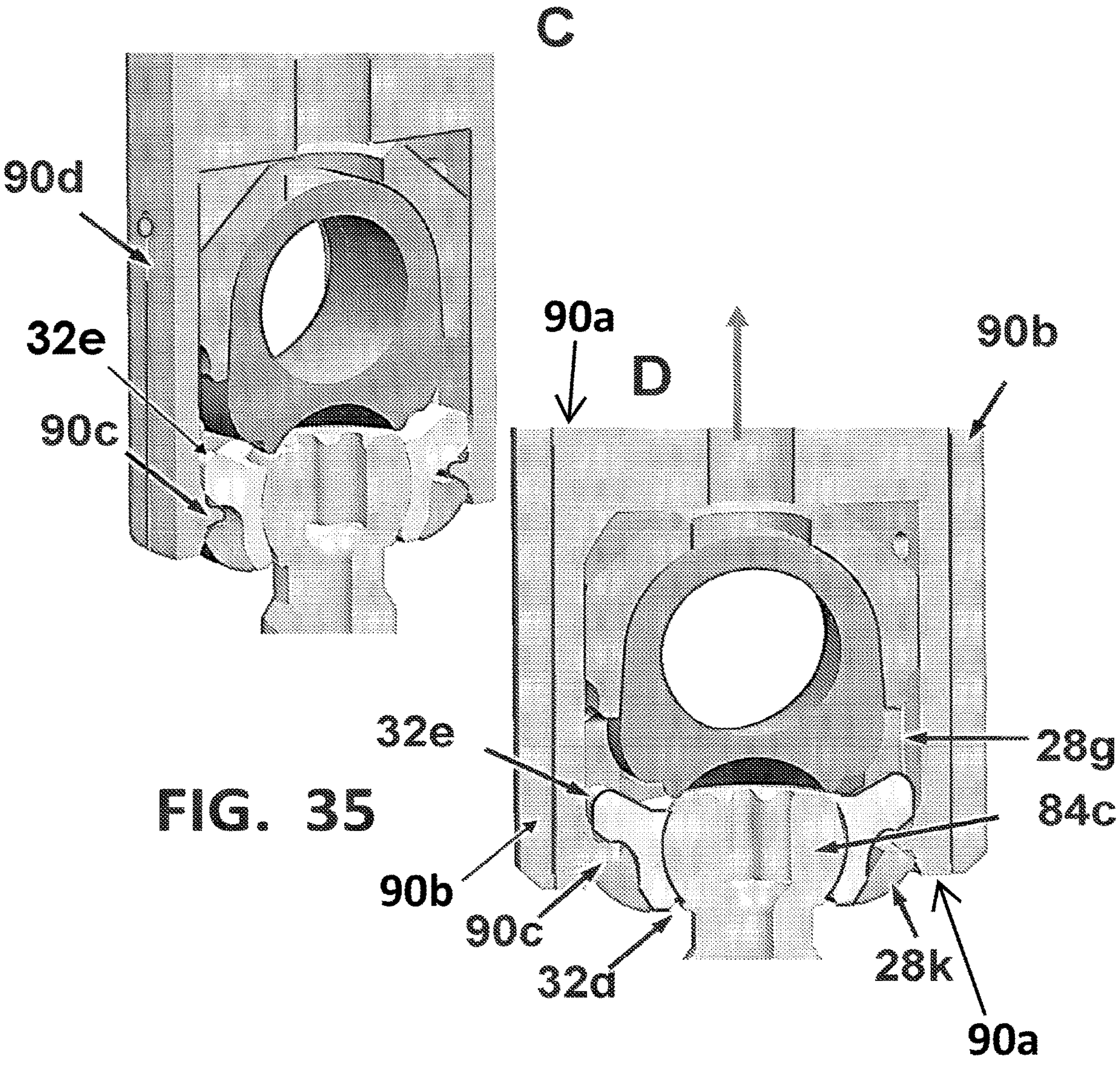

FIG. 35 show various views of a portion of an instrument being used to remove the head of an anchor; FIG. 35A shows a cross sectional view of the assembled and implanted anchor; FIG. 35B shows the implanted anchor with a portion of a first instrument placed over the head; FIG. 35C is a cross sectional representation of the apparatus of FIG. 35B; and FIG. 35D is a cross sectional representation of a second instrument being placed over the apparatus of FIG. 35C.

FIG. 35 show a version of a pop-in retained anchor 10, similar to that shown in FIGS. 18, 20, 21C, and 26, but with a modified pop-in retaining ring to facilitate removal of the head 20 from the support device 80.

Referring to FIG. 35A, anchor 10 preferably includes a support device retention ring 32*a*, which preferably includes a spherical pocket to support therein a spherical support device junction 82*c* so as to permit polyaxial movement of head 20 relative to anchor 80. Preferably, retention member 32*a* permits a pop-on assembly of a preassembled head 20 (including a bushing 50) onto a previously implanted support device 80. The head to support device member 32 of anchor 10 preferably includes a pair of outwardly extending projections or wings 32*e* the ends of which are externally accessible through windows or cutouts 28*g* on opposite sides of head 20.

FIGS. 35B and 35C show the assembled anchor of FIG. 35A over which a first inner sleeve 90*a* of an instrument has been placed by a surgeon. Sleeve 90*a* includes a flexible portion preferably defined between a pair of slits 90*d*, with flexible sections being presented on opposite sides of sleeve 90*a*, and in general alignment with wings or tabs 32*e*. As best seen in FIG. 35C, each of the flexible portions of sleeve 90*a* include a ledge or projection or tooth 90*c* that slides in place and is received on the underneath (distal) side of each wing 32*e*. These teeth 90*c*, being integral with the flexible portion 90*c*, bend outwardly out of the way when sleeve 90*a* is installed, but elastically spring back into location after passing over the outward ends of wings 32*e*.

FIG. 35D shows a subsequent act of removal, which is to insert a second, outer sleeve 90*b* over the inner sleeve 90*a*. Preferably, the inner diameter of outer sleeve 90*b* is a close sliding fit with the outer diameter of inner sleeve 90*a*, as shown in FIG. 35D. The placement of sleeve 90*b* over sleeve 90*a* prevents flexible portion 90*d* from expanding outward. Therefore, when the two sleeves 90*a* and 90*b* are pulled upward (in a proximal direction) the teeth 90*c* remain engaged with the underside of the corresponding wing 32*e* (because the teeth 90*c* can no longer expand outward).

Therefore, upward movement causes an inward compressing of wings 32*d*, which will result in an enlargement of the distal aperture 32*d* that surrounds the underside of spherical junction 84*c*. As this aperture opens, the assembled head (with bushing and retaining member 32*a*) can be pulled over the spherical head 84*c*, and removed from the support device 80. In the embodiment shown in FIGS. 35A and 35D, the head 20 can include a further extension 28*k* that generally surrounds the distalmost portion of member 32*a*, and proximate to aperture 32*d*. In such embodiments, the upward movement of the instrument assembly, and therefore of the wings 32*e*, results in a movement of the annular material surrounding aperture 32*d* through a conical annular area between the inside of extension 28*k* and the outside of head 84*c*. In this manner, as aperture 32*d* opens it further slides up (and generally maintains close contact) with the spherical head 84*c*. These extensions 28*k* assist in preventing the unwanted expansion of aperture 32*d*, as could be a result of relative motion among the polyaxial head 20, supporting device 80, and surrounding tissue.

Figure 36:
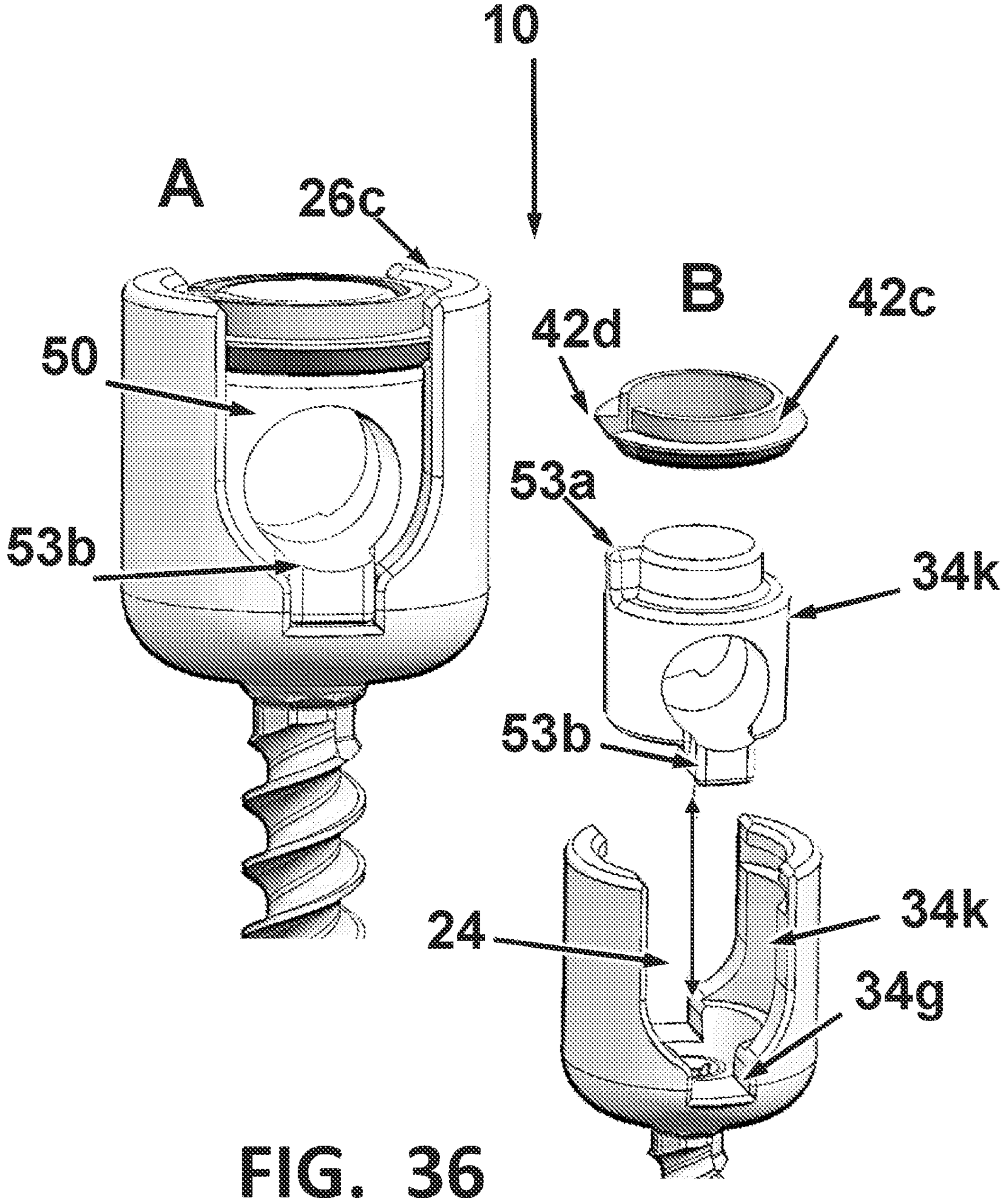
FIG. 36 show various views of an anchor according to another embodiment of the present invention.
Figure 36:
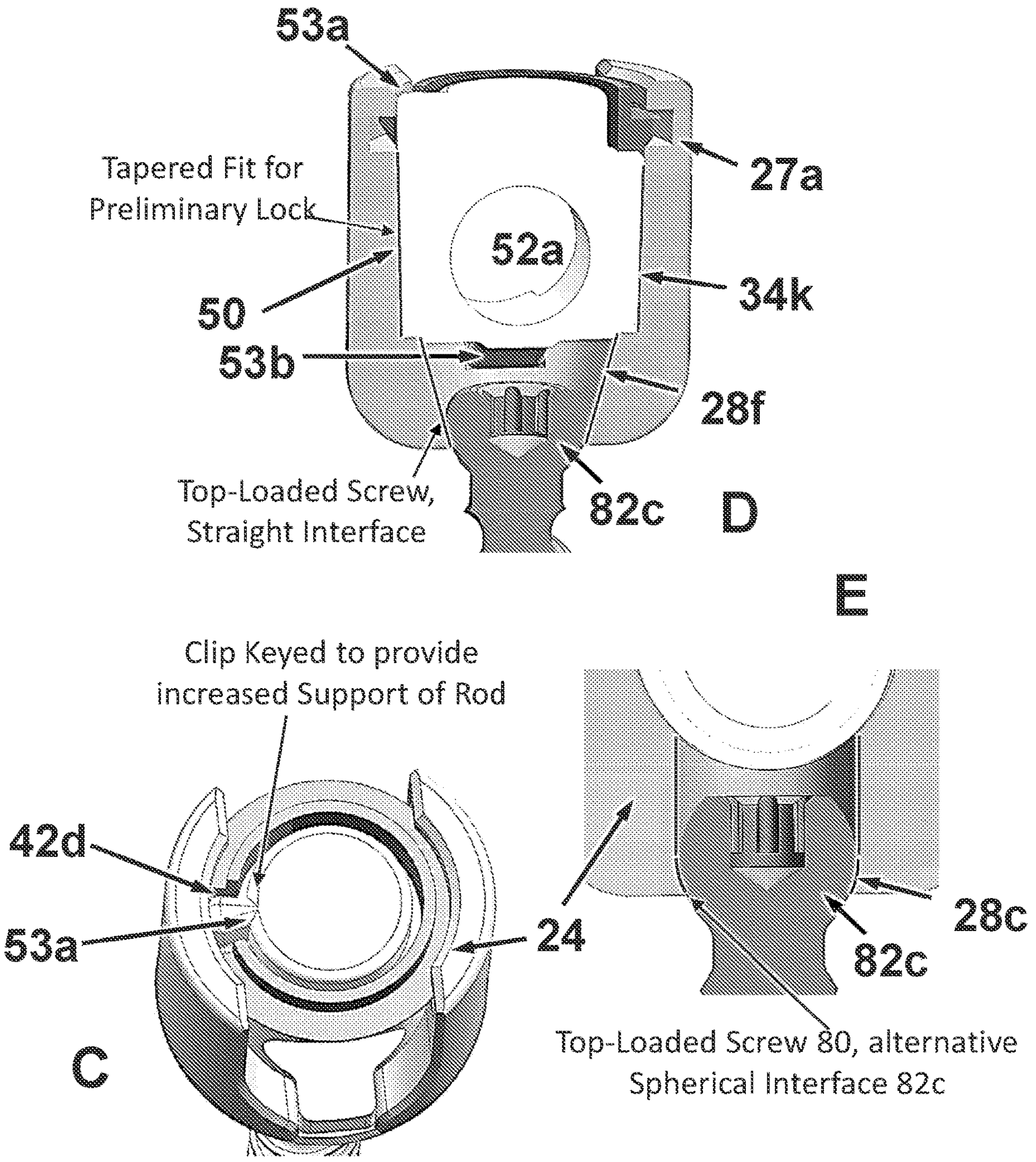

FIG. 36 show various views of an anchor according another embodiment of the present invention; FIG. 36A is a perspective view of a portion of an assembled anchor; FIG. 36B is an exploded view of the anchor of FIG. 36A; FIG. 36C is a top perspective view of the anchor of FIG. 36A; FIG. 36D is a cross sectional view taken perpendicular to the rod pathway of FIG. 36A; FIG. 36E is a partial cutaway of the apparatus of FIG. 36D.

FIG. 36 show various views of an anchor 10 including a tapered-fit bushing contained within an anchor head 20 by means of a tapered fit, and being connected to a support device by a spherical interface for polyaxial movement. Referring to FIG. 36B, a bushing 50 having a central cylindrical rod pathway (by way of example only) and including a top bushing extension 53*a* and a bottom bushing extension 53*b* is received within a cavity 24 of a head 20. The bottom bushing extensions 53*b* of bushing 50 are placed on generally opposite sides of the bushing centerline, and each is received within a corresponding interface groove 34*g*. Referring to FIG. 36D, it can be seen that each bottom extension 53*b* extends outwardly from a central underneath surface, and extending laterally and oppositely into rectangular cross sections that fit within one of the grooves 34*g*. The placement of bushing extensions 53*b* within grooves of the attachment head 20 minimizes any tendency for rotation of the bushing with the cavity 24. In some embodiments, the bottom extension 53*b* extends vertically from the bottom of slot 34*g* up to the rod pathway 52*a*. In this manner, the extensions 53*b* provide support and clearance of rod 4 relative to head 20 so as to prevent contact with head 20.

Preferably, the bushing 50 and head 20 interface with one another by a tapered sidewall 34*k* that extends on either side of rod pathway 52*a*. Preferably, bushing 50 and anchor 20 have complementary-shaped conically tapered abutting surfaces. However, it is further understood that the conical angle of the exterior of bushing 50 does not have to be the same as the conical inner diameter of cavity 24. Therefore, the interface 34*k* between the bushing and the head is preferably parallel, but is not so constrained in other embodiments, and could be slight diverging or slightly converging (with reference to the proximal to distal axial direction). Preferably, bushing 50 is a snug fit in cavity 24, and as a result forms a reliable preliminary lock between head 20 and bushing 50 as the anchor is assembled onto the implantation site.

After a subassembly of the rod, bushing, head, and support device has been achieved, a C-clip 42*c* is placed within a groove 27*a* of head 20. Clip 42*c* includes a split 42*d* that is adapted and configured to contain within it the top bushing extension or projection 53*a*. FIG. 36D shows the assembly of clip 42*c* into groove 27*a*. Clip 42*c* preferably prevents vertical pull-out of bushing 50, prevents rotation of bushing 50 within cavity 24, and further provides added rigidity to bushing 50 by ensuring that there is support over the rod by the bottom surface of the C-clip. FIG. 36E shows a support device 80 having a spherical interface 82*c* that is received with a spherically shaped pocked of head 20. However, it is understood that nay of the support devices and methods shown herein can be adapted into the anchor of FIG. 36.

In one embodiment, the device of FIG. 36 are implanted in the following manner: (1) insert screw and tulip head into bone; (2) place the bushing onto the rod; (3) reduce the bushing into the tulip; and (4) use the clip to lock the assembly together.

Figure 37:
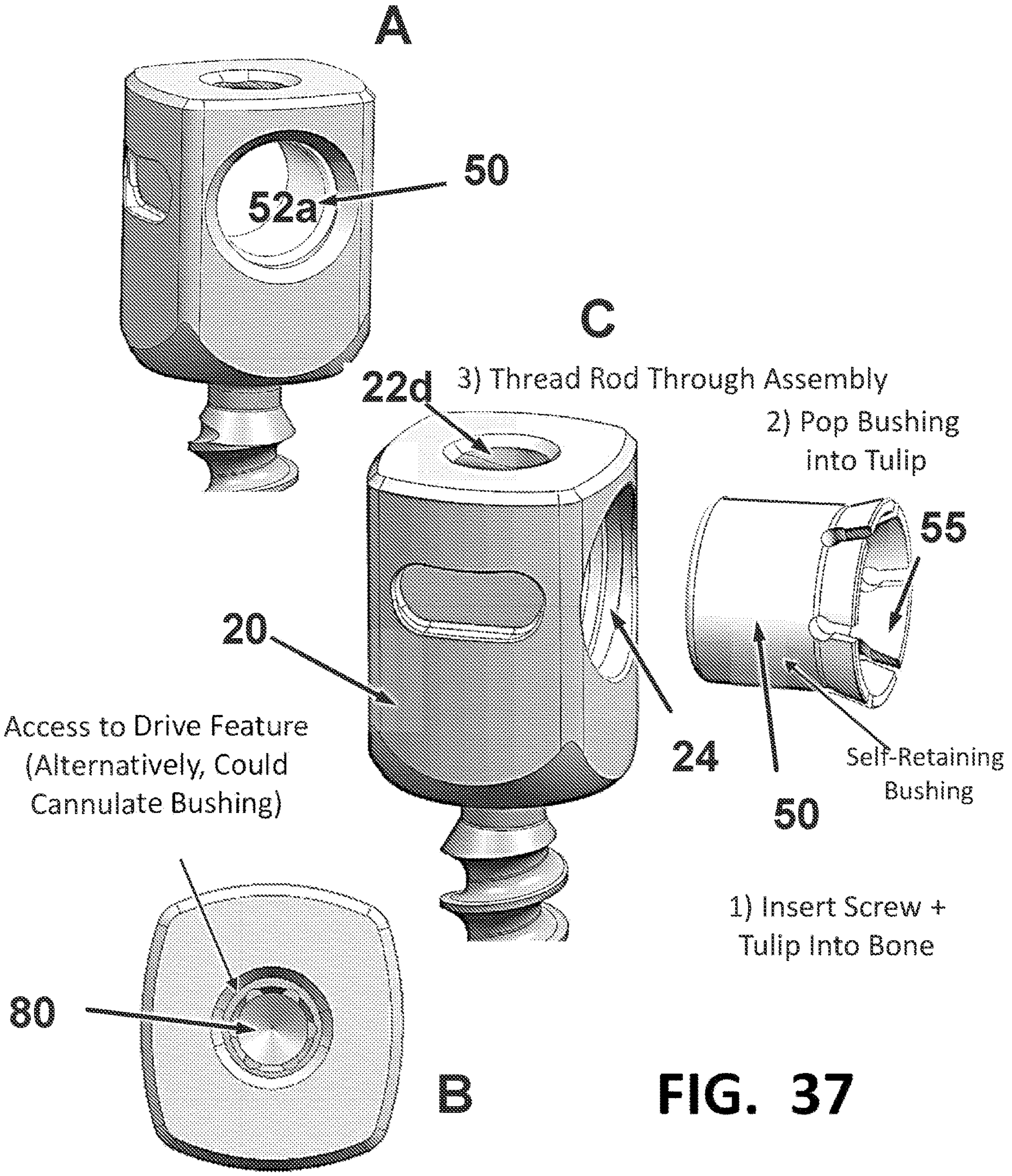
FIG. 37 show various views of an anchor according to another embodiment of the present invention.
Figure 37:
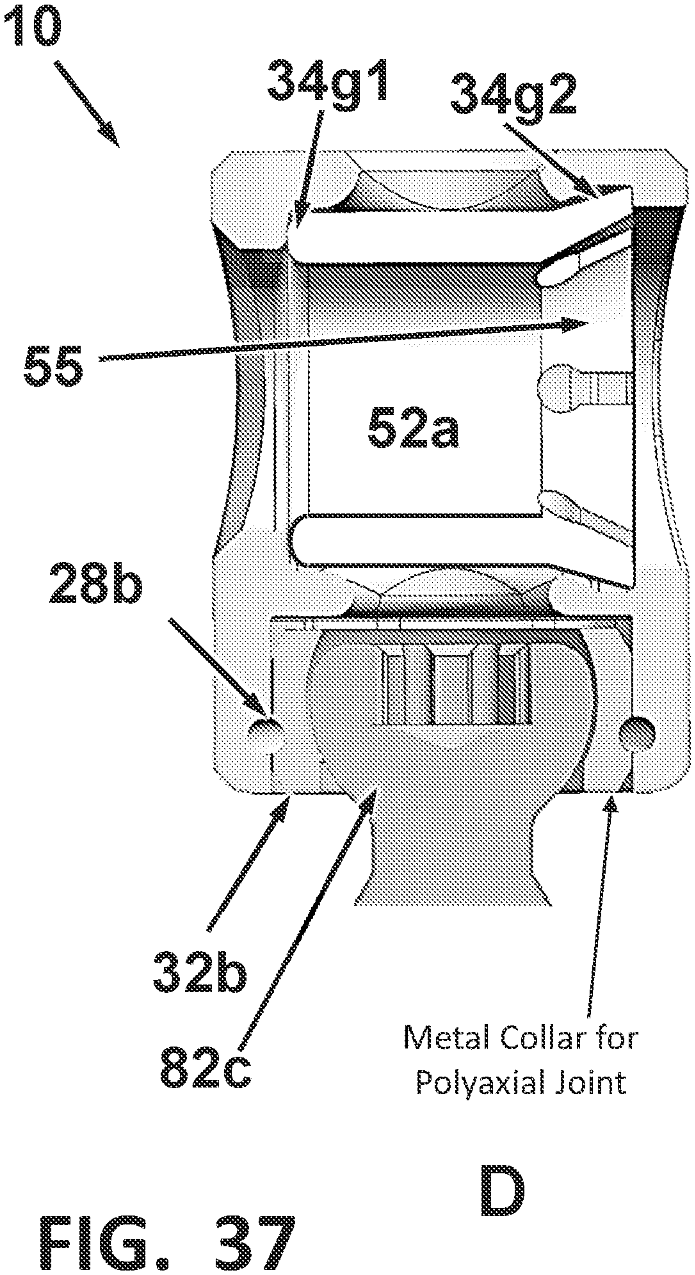

FIG. 37 depict various views of an anchor 10 according to another embodiment of the present invention; FIG. 37A shows a side, perspective view of a portion of the assembly; FIG. 37B shows a top planar view of a portion of the assembly; FIG. 37C shows a partly exploded, side, perspective view of a portion of the assembly; and FIG. 37D shows a side cross sectional view of a portion of the assembly.

FIG. 37 depict an anchor 10 according to one embodiment of the present invention that includes a bushing 50 that can be assembled into a head 20 such that it is self-retained within the cavity 24 of head 20. In some embodiments, this assembly can be done prior to implantation, or during implantation.

FIG. 37D shows a cross sectional view of the assembled anchor 10. A polymer bushing 50 with a preferably cylindrical section is shown, along with a plurality of outwardly expanding tabs 55, each connected to the cylindrical portion by a living hinge. Bushing 50 is inserted into the cavity 24 in the direction of rod pathway 52*a*. Referring to FIG. 37C, the bushing 50 can be seen prior to insertion, and aligned with one end of cavity 24. The cylindrical section of bushing 50 is first inserted, and after being fully inserted, will rest within a preferably cylindrical groove or ledge 34*g*1. Ledge 34*g*1 prevents bushing 50 from being pushed completely through head 20. As the opposite end of bushing 50 (with the hinged tabs 55) enters cavity 24, each tab is bent inward slightly (as permitted by the slits or cutouts between adjacent tabs), so as to pass underneath the entrance to cavity 24. After passing through the entrance, and when fully inserted, the tabs 55 spring back into a groove 34*g*2 that has an inner diameter larger than the inner diameter of the inlet to cavity 24. Once fully nested within cavity 24, the opposing grooves or ledges 34*g*1 and 34*g*2 prevent bushing 50 from being axially removed from head 20.

Referring again to FIG. 37D, it can be seen that the head 20 includes a generally cylindrical pocket 28*b* that receives within it an interface member 32*b*. Device member 32*b* includes an internal pocket that preferably has a shape complementary to that of the external shape of the device junction 82. As shown, the device junction is generally spherical, permitting rotation of head 20 in three directions relative to support device 80. Referring to FIGS. 37B and 37C, it is shown that head 22 includes a top through aperture 22*d* through which the surgeon can access the driving portion of support device 80.

Figure 38A:
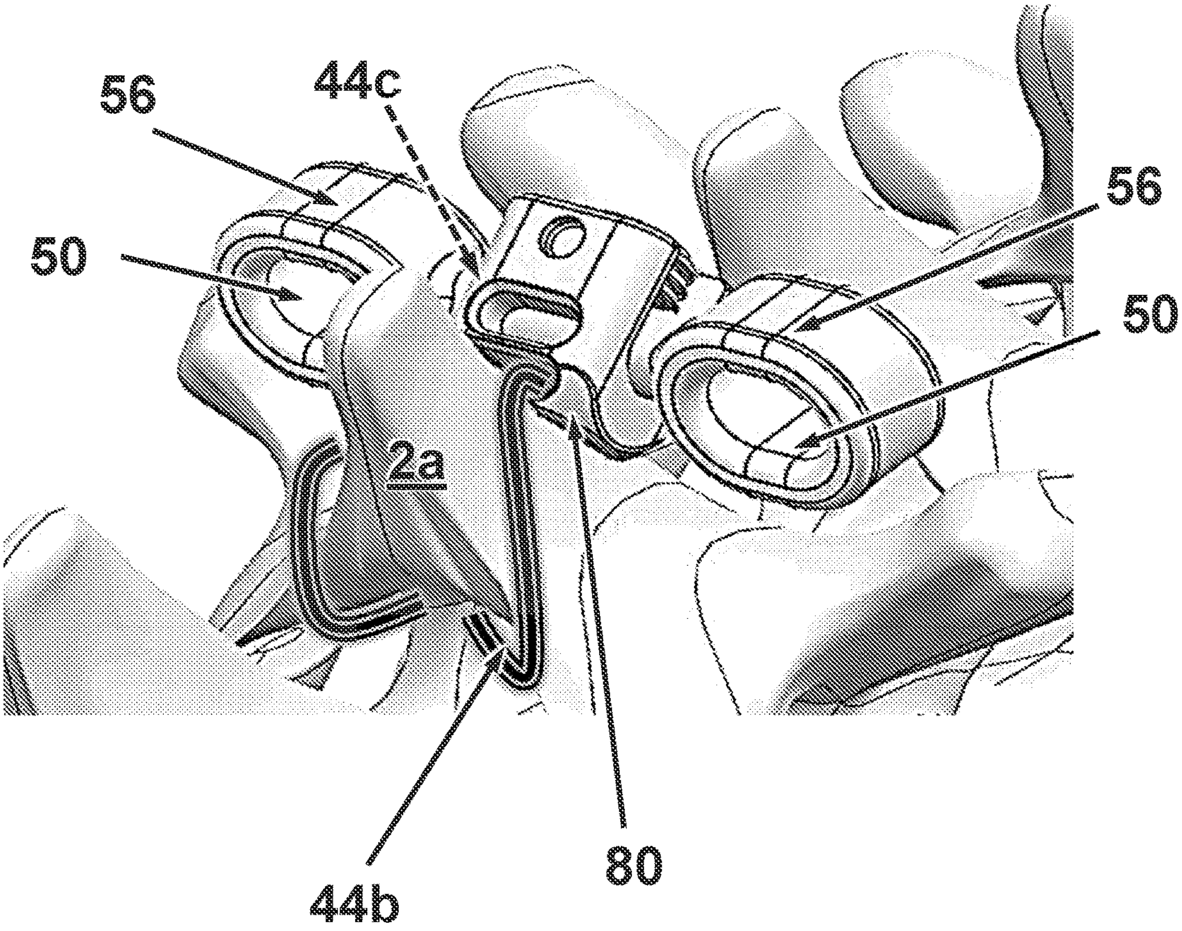
FIGS. 38A and 38B present CAD-rendered perspective views of yet another embodiment, showing (A) implanted and (B) not implanted depictions, respectively.
Figure 38B:
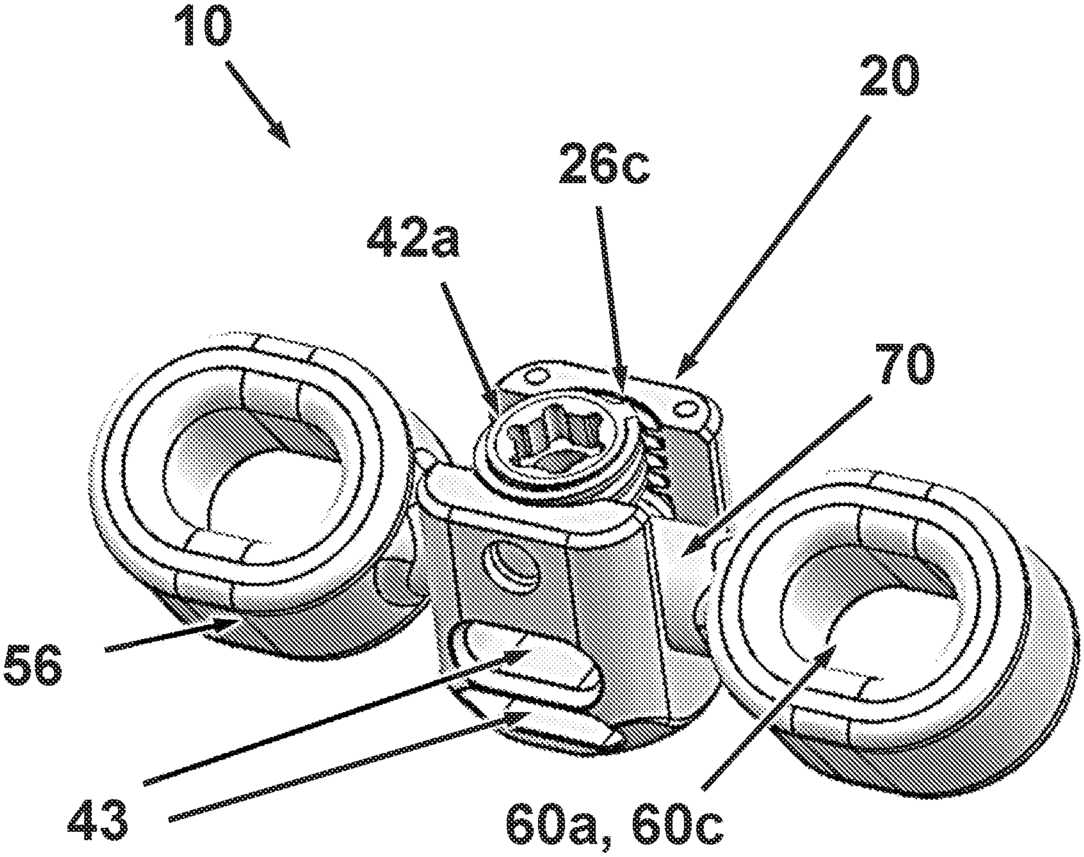

FIGS. 38A and 38B depict an anchor assembly 10 according to another embodiment of the present invention. FIGS. 38A and 38B show implanted and non-implanted perspective depictions of an assembled guiding anchor 10 that includes, in some embodiments, a pair of laterally, spaced-apart bushings 50 that are supported by a head 20.

In one embodiment, head 20 is coupled to a spinous process 2*a* (see FIG. 38A) by a flexible connector. A loop of the flexible connector extends from a first slot 43, wraps around the spinous process 2*a*P, and is received within a second slot 43 (not shown) in a manner similar to that shown in FIG. 28. One end of the flexible connector includes a connector retention device 44*c* which includes an enlarged end that is incapable of passing through slot 43. The other, free end of the flexible connector extends through the topmost slot 43, where it can be held in compression between a support arm 70 and an inner surface of head 20.

FIG. 38B shows a non-implanted depiction of anchor 10. Anchor 10 includes a readily separable component that includes a central support arm 70 and the laterally extending bushing supports 56. The arm 70 is adapted and configured to fit within an internal passageway of head 20, in a manner similar to the internal support of rod 4 as shown in FIG. 28B. Referring again to FIG. 38B, as set screw 42*a* is tightened within the threads of the opposing tulip arms 26*c*, friction between connector 44 and central support 70 (above) and a surface of head 20 (below) in frictional compression.

Support arm 70 includes on opposing ends a preferably integral bushing container 56. Each container 56 includes within it a bushing 50 that is adapted and configured to slidingly receive within it a rod (not shown). The bushings 50 include rod interface, internal shapes 60 which are shown to be noncylindrical, or oblong, or oval-shaped. It is further understood that the interior shape of the bushing can be of any type that limits or constrains certain movements (rotation or translation in one or more directions), while permitting axial sliding of the rod, and further permitting sideways or lateral clearance to accommodate rod centerlines that do not necessarily pass through the center of the bushing.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

The invention claimed is:

1. An implantable spinal anchor for supporting a rod, comprising:

a head having a cavity adapted and configured to support an implantable rod;

a device adapted and configured for supporting said head from a vertebra;

a bushing supported by the head and within the cavity and having two open ends and defining a pathway for receiving the rod that extends from one open end to the other open end, said bushing being at least one of formed in an organic material or coated with an organic material, said bushing being adapted and configured to limit motions of the rod in all directions perpendicular to a longitudinal axis of the rod and facilitate sliding motion of the rod along the axis within the pathway; and a threaded member, wherein said device includes a bone screw having a device junction, a tip, and a threaded portion therebetween, said device junction having a rounded external shape, said head including a junction pocket having a rounded internal shape adapted and configured to receive therein the device junction and permit rotation of said device relative to said head in at least one direction, wherein said junction pocket and said device junction are adapted and configured to permit polyaxial movement of said device junction within said junction pocket, wherein said head defines a threaded channel, said threaded member extends from the threaded channel into abutment with said bushing without obstructing said pathway, and said threaded member cooperates with said head to fixedly position said bushing relative to said cavity, and wherein said bushing includes a tubular sidewall extending between said open ends, said bushing further includes a pair of ridges protruding from said sidewall, said ridges are adapted and configured to receive said threaded member therebetween, and said bushing and said cavity are adapted and configured for said cavity to receive said bushing into said cavity in a direction substantially parallel to the axis of the rod.

2. The spinal anchor of claim 1 wherein said pair of ridges includes a first ridge having a first curved surface, said pair of ridges further includes a second ridge having a second curved surface, and said first curved surface and said second curved surface are adapted and configured to receive said threaded member therebetween.

3. The spinal anchor of claim 2 wherein said bottom of said cavity includes a slot parallel to the axis of the rod, said slot having a cross-sectional shape, said bushing includes a surface having a shape complementary to said cross-sectional shape of said slot, and said cross sectional shape and said bushing surface are adapted and configured to cooperate to limit rotation of said bushing within said cavity about the axis of the rod.

4. The spinal anchor of claim 3 wherein said bushing is a one-piece bushing unit separable from said head.

5. The spinal anchor of claim 2 wherein said bushing is a one-piece bushing unit separable from said head.

6. The spinal anchor of claim 1 wherein said bottom of said cavity includes a slot parallel to the axis of the rod, said slot having a cross-sectional shape, said bushing includes a surface having a shape complementary to said cross-sectional shape of said slot, and said cross sectional shape and said bushing surface are adapted and configured to cooperate to limit rotation of said bushing within said cavity about the axis of the rod.

7. The spinal anchor of claim 6 wherein said bushing is a one-piece bushing unit separable from said head.

8. The spinal anchor of claim 1 wherein said bushing is a one-piece bushing unit separable from said head.

* * * * *